US007981072B2

(12) United States Patent
Uesugi et al.

(10) Patent No.: US 7,981,072 B2
(45) Date of Patent: Jul. 19, 2011

(54) METHOD AND APPARATUS FOR SUPPLYING PREDETERMINED GAS INTO BODY CAVITIES OF A PATIENT

(75) Inventors: Takefumi Uesugi, Tokyo (JP); Masashi Umemura, Tokyo (JP); Daisuke Sano, Tokyo (JP); Kenji Noda, Tokyo (JP); Atsuhiko Kasahi, Tokyo (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 12/650,861

(22) Filed: Dec. 31, 2009

(65) Prior Publication Data
US 2010/0106080 A1 Apr. 29, 2010

Related U.S. Application Data

(63) Continuation of application No. 11/265,687, filed on Nov. 2, 2005, now abandoned.

(30) Foreign Application Priority Data

Nov. 2, 2004 (JP) ................................. 2004-319747
Nov. 5, 2004 (JP) ................................. 2004-322640

(51) Int. Cl.
*A61M 37/00* (2006.01)
(52) U.S. Cl. ............... 604/23; 604/24; 604/25; 604/26; 604/28; 604/30; 604/31; 600/560
(58) Field of Classification Search ................ 600/560; 604/23–26, 28, 30, 31
See application file for complete search history.

(56) References Cited

U.S. PATENT DOCUMENTS

| | | | | |
|---|---|---|---|---|
| 3,858,572 A | * | 1/1975 | Binard et al. | 600/560 |
| 4,595,004 A | * | 6/1986 | Czech | 128/204.21 |
| 4,657,160 A | * | 4/1987 | Woods et al. | 222/94 |
| 4,735,603 A | * | 4/1988 | Goodson et al. | 604/21 |
| 4,795,424 A | * | 1/1989 | Burner | 604/30 |
| 5,011,469 A | * | 4/1991 | Buckberg et al. | 604/6.11 |
| 5,013,294 A | * | 5/1991 | Baier | 604/26 |
| 5,035,865 A | * | 7/1991 | Inaba et al. | 422/99 |
| 5,152,745 A | * | 10/1992 | Steiner et al. | 604/26 |
| 5,246,419 A | * | 9/1993 | Absten | 604/26 |
| 5,328,458 A | * | 7/1994 | Sekino et al. | 604/23 |
| 5,342,298 A | * | 8/1994 | Michaels et al. | 604/65 |
| 5,590,684 A | * | 1/1997 | Alberts et al. | 137/489 |
| 5,676,650 A | * | 10/1997 | Grieshaber et al. | 604/28 |
| 5,830,176 A | * | 11/1998 | Mackool | 604/22 |
| 5,979,488 A | * | 11/1999 | Smith et al. | 137/312 |
| 6,126,610 A | * | 10/2000 | Rich et al. | 600/529 |
| 6,206,878 B1 | * | 3/2001 | Bishop et al. | 606/49 |
| 6,299,592 B1 | * | 10/2001 | Zander | 604/26 |
| 2001/0000262 A1 | * | 4/2001 | McEwen et al. | 601/11 |
| 2006/0116630 A1 | * | 6/2006 | Garabet | 604/65 |

* cited by examiner

*Primary Examiner* — Nicholas D Lucchesi
*Assistant Examiner* — Scott Medway
(74) *Attorney, Agent, or Firm* — Ostrolenk Faber LLP

(57) ABSTRACT

A gas supply apparatus measures a first pressure inside a first body cavity of a patient and a second pressure inside a second body cavity of the patient. The gas supply apparatus regulates a pressure of a predetermined gas based on the measured first and second pressures inside the first and second body cavities.

5 Claims, 33 Drawing Sheets

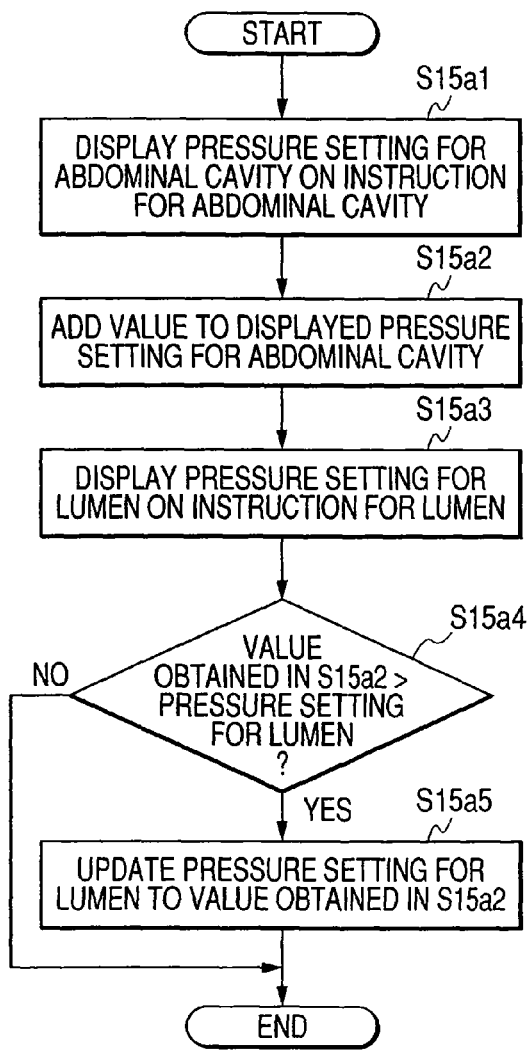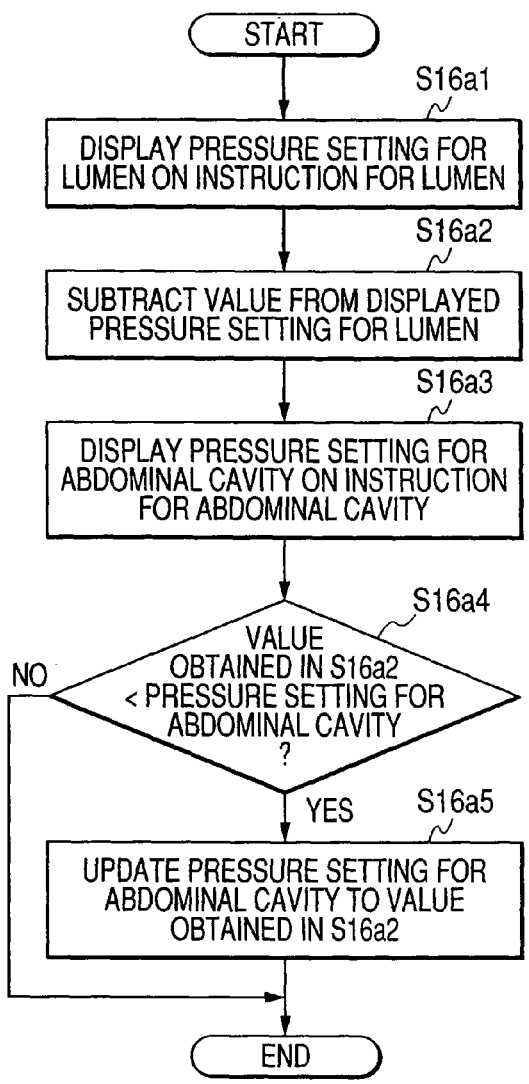

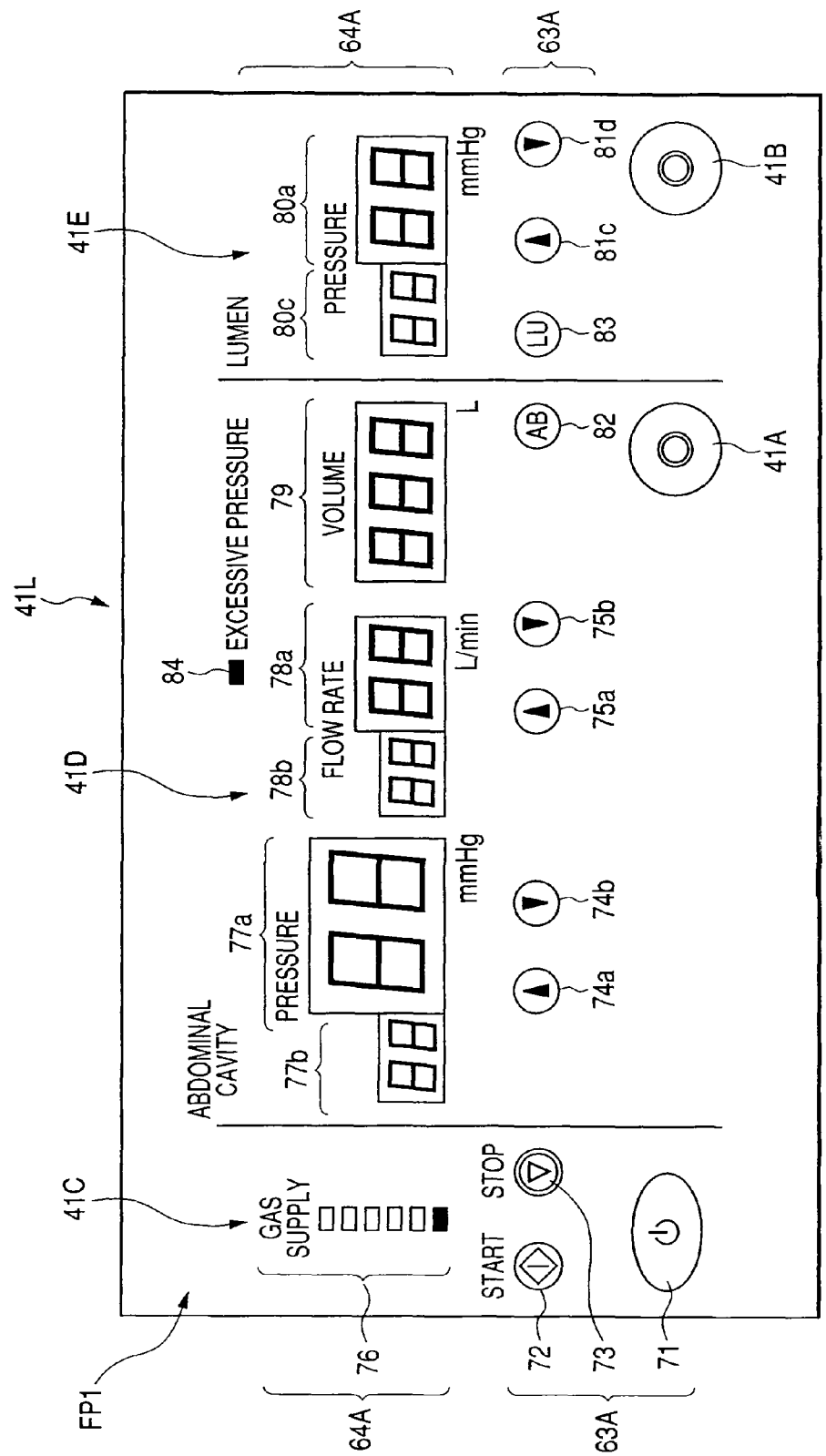

METHOD AND APPARATUS FOR SUPPLYING PREDETERMINED GAS INTO BODY CAVITIES OF A PATIENT

CROSS REFERENCE TO RELATED APPLICATIONS

This application is a Continuation of U.S. application Ser. No. 11/265,687, filed Nov. 2, 2005, which is a Continuation-In-Part (CIP) of U.S. application Ser. No. 11/093,389, filed Mar. 30, 2005, the descriptions of which are all incorporated herein by reference.

In addition, this application is based upon the prior Japanese Patent Applications 2004-108364, 2004-319747 and 2004-322640, which are filed on Mar. 31, 2004, Nov. 2, 2004 and Nov. 5, 2004, respectively, and claims the benefit of priority therefrom so that the descriptions of which are all incorporated herein by reference.

FIELD OF THE INVENTION

The present invention relates to methods and systems for supplying predetermined gas into body cavities of a patient.

DESCRIPTION OF THE RELATED ART

In recent years, laparoscopic surgery has been practiced extensively. The laparoscopic surgery is executed for treating a patient with minimally invasive capability.

Specifically, in the laparoscopic surgery, for example, a first trocar for introducing a rigid endoscope, referred to as "rigidscope", for observation to a body cavity of a patient is inserted thereinto. In addition, a second trocar for introducing a treatment tool to a site to be treated is inserted thereinto.

In such laparoscopic surgery, an insufflator has been used for supplying carbon dioxide gas (hereinafter also referred to as $CO_2$) as insufflating gas into an abdominal cavity of the patient to ensure the rigidscope field and a space to manipulate the treatment tool.

Conventionally, some types of insufflators for supplying carbon dioxide gas into one of body cavities, such as an abdominal cavity of the patient, have been prepared.

For example, Japanese Unexamined Patent Publication No. 2000-139830 discloses a gas supplying apparatus designed to feed a control signal to a pressure-regulating valve when gas flow volume does not reach a predetermined value. The control signal causes the pressure-regulating valve to increase the pressure of the output gas to control the amount thereof, thereby keeping an internal pressure of a living body at the predetermined value.

Moreover, Japanese Unexamined Patent Publication No. 8-256972 discloses an insufflator having a plurality of electromagnetic valves for controlling a state of gas flowing through a gas delivery channel extending from a gas supply source to an insufflation tool. Specifically, the insufflator is designed such that the plurality of electromagnetic values is integrated with a manifold valve, allowing the gas-flow state controlling section to become compact.

Furthermore, Japanese Unexamined Patent Publication No. 2000-139823 discloses an insufflation system for insufflating air into a lumen to keep constant the pressure inside thereof.

In the meanwhile, when diagnosing and treating a lumen, such as the stomach, the large intestine, and the like of a patient as the body cavities thereof, a flexible endoscope, referred to as "flexiblescope", and a treatment tool therefor have been used. The flexiblescope has one thin and flexible end portion to be used as an access site into the lumen. The treatment tool for the flexiblescope is designed so that its forceps channel is inserted into the flexiblescope to project through an opening formed in the head of the one end portion of the flexiblescope.

When executing curative intervention, such as diagnosis and treatment of a lumen, for example, the stomach, the large intestine or the like of a patient, under such monitored conditions with the flexiblescope, in some cases, gas for lumens is injected into the lumen. The injection of gas aims at securing the flexiblescope field and a space to manipulate the treatment tool.

In these cases, the gas to be supplied into the lumen can be transferred with a gas supply pump through the flexible scope. As the gas for lumens, air has been generally applied, but the carbon dioxide gas can also be used Recently, as a new attempt, in the laparoscopic surgery, the rigidscope is inserted into an abdominal cavity of a patient with the flexiblescope inserted into a lumen of the patient. This allows identification of a site to be treated in the patient based on an image of the inside of the abdominal cavity, which is obtained by the rigidscope, and that of the inside of the lumen, which is obtained by the flexiblescope.

Under such monitored conditions with both the rigidscope and flexiblescope, in some cases, air as gas for lumens is injected through the flexiblescope into the lumen to inflate the lumen.

When air is supplied into the lumen, it is difficult for the air to be absorbed into the living body. This may cause the lumen to remain inflated.

For this reason, when inserting the rigidscope into an abdominal cavity of a patient while inserting the flexiblescope into a lumen thereof, using an endoscope $CO_2$ regulator (hereinafter referred to as ECR) has been considered to supply, into the lumen, carbon dioxide gas ($CO_2$), which is absorbed easily into the living body.

SUMMARY OF THE INVENTION

The present invention has been made on the background.

According to one aspect of the present invention, there is provided a gas supply apparatus for supplying predetermined gas into a first body cavity of a patient through a first delivery member and into a second body cavity of the patient through a second delivery member. The gas supply apparatus includes a pressure regulator coupled to the first and second delivery members and configured to regulate a pressure of the predetermined gas. The gas supply apparatus includes a pressure measuring unit configured to individually measure a first pressure inside the first body cavity and a second pressure inside the second body cavity. The gas supply apparatus includes a controller electrically connected to the pressure regulator and the pressure measuring unit and operative to control the pressure regulator based on the measured first and second pressures inside the first and second body cavities.

According to another aspect of the present invention, there is provided a gas supply apparatus including a plurality of delivery members communicatively coupled to a supply source of predetermined gas and configured to supply the predetermined gas into a plurality of body cavities of a patient. The gas supply apparatus includes a pressure measuring unit configured to individually measure pressures inside the plurality of body cavities, and a pressure regulator configured to regulate a pressure of the predetermined gas supplied from the supply source. The gas supply apparatus includes a controller electrically connected to the pressure regulator and the pressure measuring unit and operative to control the pressure regulator based on the measured pressures inside the plurality of body cavities to insufflate the predetermined gas into the plurality of delivery members in a predetermined order while regulating the pressure of the predetermined gas with respect to each delivery member.

According to a further aspect of the present invention, there is provided a gas insufflating apparatus for insufflating predetermined gas into a first body cavity of a patient through a first delivery member and into a second body cavity of the patient through a second delivery member. The gas insufflating apparatus includes means for measuring a first pressure inside the first body cavity and a second pressure inside the second body cavity, and means for regulating a pressure of the predetermined gas based on the measured first and second pressures inside the first and second body cavities.

According to a still further aspect of the present invention, there is provided a gas insufflating apparatus for insufflating predetermined gas supplied form a supply source into a plurality of body cavities of a patient through a plurality of delivery members. The gas insufflating apparatus includes means for individually measuring pressures inside the plurality of body cavities, and means for insufflating the predetermined gas into the plurality of delivery members in a predetermined order while regulating the pressure of the predetermined gas with respect to each delivery member based on the measured pressures inside the plurality of body cavities.

According to a still further aspect of the present invention, there is provided an observation system including a gas supply apparatus for supplying predetermined gas into a first body cavity of a patient through a first delivery member and into a second body cavity of the patient through a second delivery member. The gas supply apparatus includes a pressure regulator coupled to the first and second delivery members and configured to regulate a pressure of the predetermined gas, and a pressure measuring unit configured to measure a first pressure inside the first body cavity and a second pressure inside the second body cavity. The gas supply apparatus includes a controller electrically connected to the pressure regulator and the pressure measuring unit and operative to control the pressure regulator based on the measured first and second pressures inside the first and second body cavities. The observation system includes an observation device integrated with a gas delivery channel and configured to be inserted into the second body cavity of the patient to observe an inside of the second body cavity. The gas delivery channel serves as part of the second delivery member.

According to a still further aspect of the present invention, there is provided an observation system including a gas supply apparatus. The gas supply apparatus includes a plurality of delivery members communicatively coupled to a supply source of predetermined gas and configured to supply the predetermined gas into a plurality of body cavities of a patient. The gas supply apparatus includes a pressure measuring unit configured to individually measure pressures inside the plurality of body cavities, and a pressure regulator configured to regulate a pressure of the predetermined gas supplied from the supply source. The gas supply apparatus includes a controller electrically connected to the pressure regulator and the pressure measuring unit and operative to control the pressure regulator based on the measured pressures inside the plurality of body cavities to insufflate the predetermined gas into the plurality of delivery members in a predetermined order while regulating the pressure of the predetermined gas with respect to each delivery member. The observation system includes an observation device integrated with a gas delivery channel and configured to be inserted into at least one of the plurality of body cavities of the patient to observe an inside of at least one of the plurality of body cavities. The gas delivery channel serves as part of at least one of the plurality of delivery members corresponding to at least one of the plurality of body cavities.

According to a still further aspect of the present invention, there is provided a method of insufflating predetermined gas to a first body cavity of a patient through a first delivery member and to a second body cavity of the patient through a second delivery member. The method includes measuring a first pressure inside the first body cavity and a second pressure inside the second body cavity, and regulating a pressure of the predetermined gas based on the measured first and second pressures inside the first and second body cavities so that the first and second pressures reach predetermined first and second pressure settings, respectively.

According to a still further aspect of the present invention, there is provided a method of insufflating predetermined gas supplied form a supply source into a plurality of body cavities of a patient through a plurality of delivery members. The method includes individually measuring pressures inside the plurality of body cavities, and insufflating the predetermined gas into the plurality of delivery members in a predetermined order while regulating the pressure of the predetermined gas with respect to each delivery member based on the measured pressures inside the plurality of body cavities.

BRIEF DESCRIPTION OF THE DRAWINGS

Various aspects of the present invention will be more particularly described with reference to the accompanying drawings in which:

FIG. 13A is a flowchart schematically illustrating an example of control operations of a controller illustrated in FIG. 11;

FIG. 13B is a flowchart schematically illustrating another example of control operations of a controller illustrated in FIG. 11;

FIG. 14 is a view schematically illustrating a configuration example of a manually operable setting section and a display section provided on a front panel of a gas supply apparatus according to a third embodiment of the present invention;

DETAILED DESCRIPTION OF EMBODIMENTS OF THE INVENTION

Embodiments of the present invention will be described hereinafter with reference to the accompanying drawings.

First Embodiment

Figure 1:
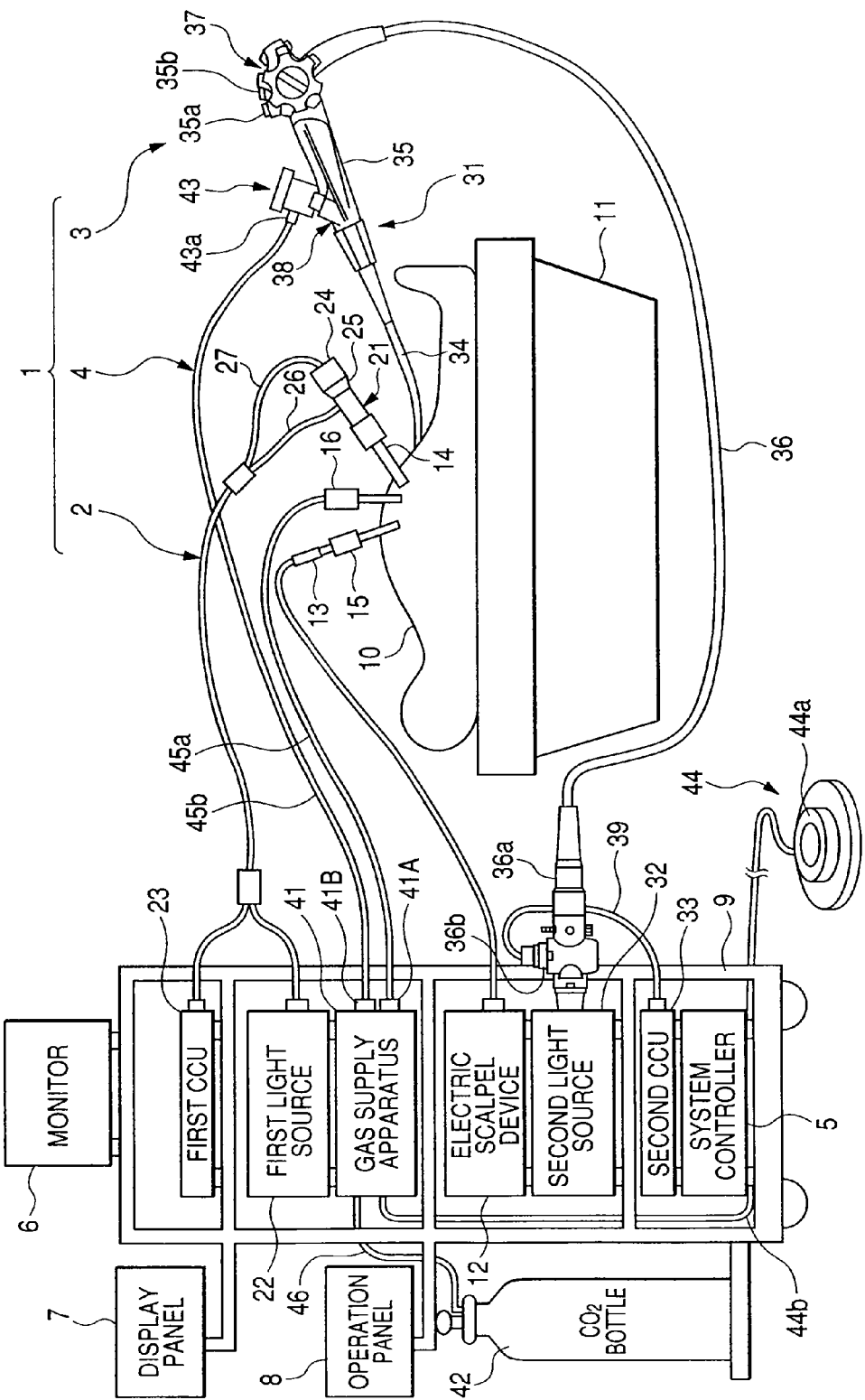
FIG. 1 is an overall structural view schematically illustrating the structure of an endoscopic surgical system equipped with a gas supply apparatus according to a first embodiment of the present invention.

As shown in FIG. 1, a laparoscopic surgery system, referred to as a surgical system hereinafter, 1 has a first endoscope system 2, a second endoscope system 3, and a gas supply system 4 according to a first embodiment of the present invention.

The surgical system 1 has a system controller 5, a monitor 6 as a display device, a center display panel 7, a center operation panel 8, and a movable cart (trolley) 9.

Reference numeral 10 designates a patient, and reference numeral 11 designates an operation table that allows the patient 11 to lie thereon. Reference numeral 12 designates an electric scalpel device as an example of operation devices, which is mounted on the cart 9. The surgical system 1 has an electric scalpel 13 serving as an operation tool. The electric scalpel 13 is electrically connected to the electric scalpel device 12.

Reference numerals 14, 15, and 16 designate first, second, and third trocars, such as medical tubes, which are inserted into, for example, an abdominal portion of the patient 10, respectively.

Specifically, the first trocar 14 allows an endoscope, described hereinafter, of the first endoscope system 2 to be guided into a body cavity, such as an abdominal cavity AC (see FIG. 2) of the patient 10. The abdominal cavity AC, which means a cavity separated by the diaphragm from the thoracic cavity above and by the plane of the pelvic inlet from the pelvic cavity below.

The second trocar 15 permits guide of a treatment tool into the abdominal cavity AC. The treatment tool, such as the electric scalpel 13, is operative to remove and/or treat a tissue corresponding to at least one site to be treated in the abdominal cavity AC.

The third trocar 16 allows predetermined gas for the abdominal cavity, such as carbon dioxide gas, to be introduced into the abdominal cavity AC. The carbon dioxide gas, referred to as "$CO_2$" can be easily absorbed into a living body, such as the patient 10, which is supplied from the gas supply system 4. The carbon dioxide gas can be introduced into the inside of the abdominal cavity AC through at least one of the trocars 14 and 15.

The first endoscope system 2 includes a rigid endoscope 21 as a first endoscope with, for example, a rigid insert portion at one end thereof. The rigid endoscope 21 is referred to as "rigidscope" hereinafter. The first endoscope system 2 includes a first light source 22, a first camera control unit 23, referred to as "first CCU" hereinafter, and a camera (TV camera) 24 for endoscopes.

One end portion of the insertion portion (not shown) of the rigidscope 21, for example, is configured to be inserted in part into the first trocar 14. The rigidscope 21 is provided with an illumination optics (not shown) and an observation optics (not shown), which are installed in the one end portion of the insertion portion. The illumination optics is composed of, for example, a light guide and the like, and configured to illuminate light onto a target, such as the site to be treated, of the inside of the patient 10. For example, the observation optics is composed of relay lenses and the like. The observation optics is configured to optically deliver an optical image of the target illuminated by the light.

The rigidscope 21 is provided at the other end side of the insertion portion with an eyepiece 25 that allows an operator to observe the optical image delivered by the observation optics. The camera 24 is detachably installed in the eyepiece 25. The camera 24 is integrated with an image pickup device, such as a CCD (Charge Coupled Device) or the like, having a light sensitive pixel area, wherein the optical image delivered by the observation optics is focused on the light sensitive pixel area thereof. The optical image of the target focused on the light sensitive pixel area of the image pickup device is photoelectrically converted into an electric signal as a first image signal, by the image pickup device.

The first endoscope system 2 is provided with a light guide cable 26 extending from one side of the other end of the rigidscope 21. The light guide cable 26 is optically coupled to the first light source 22, allowing optical coupling between the rigidscope 21 and the first light source 22. The first endoscope system 2 is provided with an image pickup cable 27 electrically connecting between the first CCU 23 and the camera 24.

The first light source 22 has a function of supplying illumination light to the illumination optics of the rigidscope 21 via the light guide cable 26. The first CCU 23 is operative to execute electrical drive control of the image pickup device of the camera 24. When the first image signal corresponding to the optical image of the target, which is picked up by the image pickup device, is sent to the first CCU 23, the first CCU 23 is operative to receive the first image signal to subject the received first image signal to image processing of necessity. The first CCU 23 is operative to output the image-processed first image signal to at least one of the monitor 6 and the center display panel 7.

These operations allow at least one of the monitor 6 and the center display panel 7 to display a first image of the target thereon based on the first image signal. That is, the first image is an endoscopic image corresponding to the first image signal picked up by the rigidscope 21.

The second endoscope system 3 includes a flexible endoscope 31 as a second endoscope with, for example, a flexible insert portion 34 at one end thereof. The flexible insert portion is so flexible that it can be inserted into a lumen BC as a body cavity of the patient. In the specification, the lumen is defined as the cavity of an organ in a patient (living body), such as the cavity of the stomach, the cavity of the large intestine, the cavity of a blood vessel, or the like in the patient. The flexible endoscope 31 is referred to as "flexiblescope" hereinafter. The second endoscope system 3 includes a second light source 32, and a second CCU 33.

The flexiblescope 31 has a substantially hollow-rod (tubular) shape, which is narrow in diameter and flexible. The flexiblescope 31 is internally formed with a gas delivery channel SC (see FIG. 5).

Specifically, the flexiblescope 31 is provided at its one end with the insert portion 34 to be inserted at its one end into the interior of the lumen BC, and a manipulator 35 whose one end is joined to the other end of the insert portion 34. The manipulator 35 allows, for example, an operator to manipulate the flexiblescope 31. The flexiblescope 31 is provided with a universal cord 36 whose one end is joined to the other end of the manipulator 35.

The manipulator 35 is provided with a gas and water supply switch 35a mounted thereon. The gas and water supply switch 35a is formed with a through hole, also referred to as "gas and water supply channel), communicated with the gas delivery channel SC inside of the manipulator 35. The gas and water supply switch 35a, the gas delivery channel SC, and the insert portion 34 allow the operator to supply gas and water therethrough.

It should be noted that the term "operator" through the specification is not necessarily limited to a person who actually treats; the term "operator" refers to a concept that involves any of nurses, health workers, or other operators who assist such a treatment action.

The manipulator 35 is provided with a suction switch 35b disposed thereto and a flexion knob 37 that allows the operator to flex a flexible portion (not shown) of the flexiblescope 31. The manipulator 35 is formed with a treatment tool channel communicated with the gas delivery channel SC, and the flexiblescope 31 is provided with a treatment tool insertion opening 38 formed to be communicated with the treatment tool channel in the manipulator 35. The treatment tool insertion opening 38 allows treatment tools to be inserted therethrough. The other end of the universal cord 36 is coupled to a light source connector 36a optically detachably so that the universal cord 36 is optically coupled to the second light source 32 through the light source connector 36a.

The second light source 32 has a function of supplying illumination light to the flexiblescope 31 through the light source connector 36a and the universal cord 36.

The flexiblescope 31 is provided at its one end of the insertion portion 34 with an illumination optics. The illumination optics is composed of a light guide that can illuminate light on a target inside the patient 10, such as the lumen BC, through an illumination window disposed to one side of the one end of the insertion portion 34.

The flexiblescope 31 is provided with an image pickup device, such as a CCD or the like, installed in the one end of the insertion portion 34. The image pickup device has a light sensitive pixel area. The image pickup device is so arranged that an optical image of the target illuminated by the light outputted from the illumination optics is focused on the light sensitive pixel area of the image pickup device.

The image pickup device of the flexiblescope 31 is electrically connected to the second CCU 33 through the universal cord 36 and the like. Reference numeral 39 is an electric cable electrically connecting between an electric connector 36b attached to the light source connector 36a and the second CCU 33.

The image pickup device is operative to photoelectrically convert the optical image of the target focused on the light sensitive pixel area into an electric signal as a second image signal.

The second CCU 33 is operative to execute electrical drive control of the image pickup device. When the second image signal corresponding to the optical image of the target, which is picked up by the image pickup device, is sent to the second CCU 33 through the electric cable 39, the second CCU 33 is operative to receive the second image signal to subject the received first image signal to image processing of necessity. The second CCU 33 is operative to output the image-processed second image signal to at least one of the monitor 6 and the center display panel 7.

These operations allow at least one of the monitor 6 and the center display panel 7 to display a second image of the target thereon based on the second image signal. That is, the second image is an endoscopic image corresponding to the second image signal picked up by the flexiblescope 31.

Turning now to the gas supply system 4, it includes a gas supply apparatus 41, a carbon dioxide gas cylinder ($CO_2$ bottle) 42 as a supplier, and an insertion adapter, referred to simply as adapter, 43. The gas supply system 4 has a foot switch 44 serving as an operation switch for controlling supply of the carbon dioxide gas into the lumen BC, a first tube 45a for abdominal cavities, and a second tube 45b for lumens. The $CO_2$ bottle 42 has stored carbon dioxide in liquid.

The gas supply apparatus 41 is provided with a first adapter (connector) 41A for insufflation of the abdominal cavity AC and a second adapter 41B for insufflation of the lumen BC. The first adapter 41A is airtightly coupled to one end of the first tube 45a. The other end of the first tube 45a is airtightly coupled to the third trocar 16. The second adapter 41B is airtightly coupled to one end of the second tube 45b. The other end of the second tube 45b is airtightly coupled to a tube coupler 43a formed on one side of the adapter 43. The adapter 43 is attached to the manipulator 35 of the flexiblescope 31 to be airtightly communicated with the gas delivery channel SC thereinside. This structure allows the second tube 45b to be communicated with the gas delivery channel SC inside the flexiblescope 31 through the adapter 43.

The foot switch 44 is provided with a switch portion 44a and is configured to provide instructions to instruct supply of the carbon dioxide gas into the lumen BC to the gas supply apparatus 41 while the operator or the like depresses the switch portion 44a with operator's foot or the like.

The gas supply apparatus 41 and the $CO_2$ bottle 42 are coupled to each other through a high-pressure gas tube 46. The gas supply apparatus 41 and the foot switch 44 are electrically connected to each other through a foot switch cable 44b. The electrical connection between the foot switch 44 and the gas supply apparatus 41 can be established by wireless. Each of the tubes 45a and 45b is made from a material such as, for instance, silicone, Teflon®, or other similar materials.

The system controller 5 is operative to perform control of the whole system 1. With the system controller 5, the center display panel 7, the center operation panel 8, and peripheral devices including the electric scalpel device 12, the first light source 22, the second light source 32, the first CCU 23, the second CCU 33, and the gas supply apparatus 41 are communicably connected through communication buses (not shown), respectively.

The monitor 6 has a function of receiving the first image signal and/or the second image signal outputted from the first CCU 23 and/or the second CCU 33 to display at least one of the first and second images thereon based on the received first and second image signals.

The center display panel 7 is composed of a display screen, such as a liquid crystal screen or the like, and is electrically connected to the system controller 5. The center display panel 7 allows concentrative display of operating states of the peripheral devices together with the first and second images on the display screen.

The center operation panel 8 is composed of a display section, such as a liquid crystal screen or the like, and a touch-sensitive device integrally formed on the display section. The display section of the center operation panel 8 has a display function of providing a setting screen on which operable switches (buttons) for the peripheral devices are graphically displayed. The display section has an operating function that allows the operator to operate the operable switches by touching them.

Specifically, the operator touches at least one of the operable switches with, for example, a finger so that the touch-sensitive device sets operating conditions corresponding to at least one of the touched operable switches to remotely send to the system controller 5 instructions for operating a corresponding one of the peripheral devices based on the set operating conditions. These remote operations of the graphical operable switches on the center operation panel 8 with respect to the peripheral devices are substantially identical to direct operations of operable switches directly attached to the peripheral devices.

The peripheral devices including the electric scalpel device 12, the first and second light sources 22 and 32, the first and second CCUs 23 and 33, the gas supply apparatus 41, and a VTR (Video Tape Recorder), which is not shown, are mounted on the cart 9. In addition, the system controller 5, the center display panel 7, and the center operation panel 8 are mounted on the cart 9.

Figure 2:
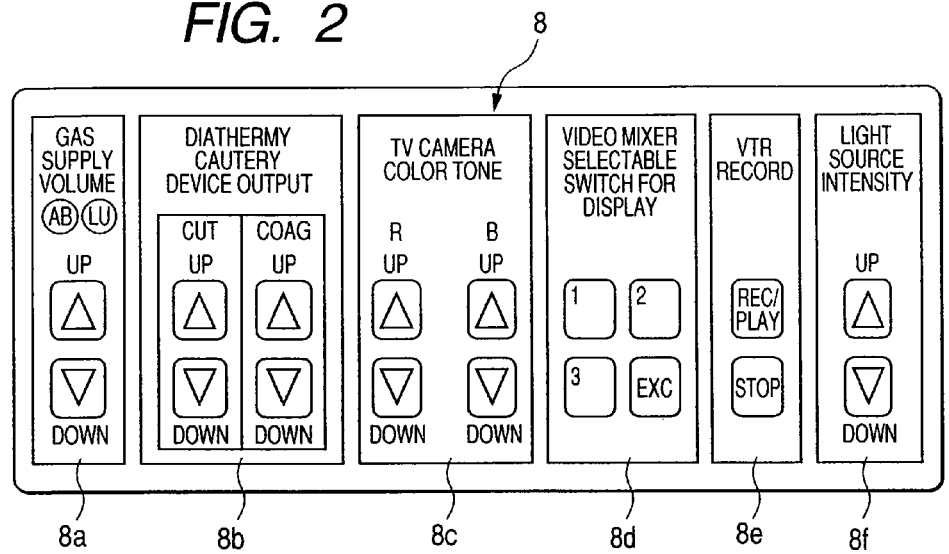
FIG. 2 is a view schematically illustrating a configuration example of an operation panel illustrated in FIG. 1.

A configuration example of the operation panel 8 is illustrated in FIG. 2.

The operation panel 8 is composed of a display screen, such as a liquid crystal display, and a touch-sensitive device integrally formed on the display screen. On the display screen, manually operable sections, such as manually operable graphical buttons, are displayed. The manually operable sections allow the operator to set operating conditions (parameters) with respect to the peripheral devices to give instructions for operating them based on the set operating conditions to the system controller 5 or the corresponding peripheral device.

Specifically, the operator touches at least one of the operable sections (operable buttons), with, for example, a finger so that the touch-sensitive device sets operating conditions corresponding to at least one of the touched operable sections to remotely send to the system controller 5 instructions for operating the corresponding one of the peripheral devices based on the set operating conditions. The system controller 5 controls the corresponding one of the peripheral devices based on the instructions so that the corresponding one of the peripheral devices operates under the set operating conditions.

For example, as shown in FIG. 2, manual operation buttons 8a are graphically displayed on the display screen of the operation panel 8. The manual operation buttons 8a allow the operator to adjust the flow-rate of carbon dioxide gas supplied to the abdominal cavity AC or the lumen BC from the gas supply apparatus 41.

Manual operation buttons 8b are graphically displayed on the display screen of the operation panel 8. The manual operation buttons 8b permit the operator to adjust an output value of the electric scalpel device 12. Manual operation buttons 8c are graphically displayed on the display screen of the operation panel 8. The manual operation buttons 8c allow the operator to control color tones of the first and second CCUs 23 and 33.

In addition, manual operation buttons 8d are graphically displayed on the display screen of the operation panel 8. The manual operation buttons 8d allow the operator to send instructions to the system controller 5 for selectively switching the first image (the endoscopic image of the rigidscope 21) and the second image (the endoscope image of the flexiblescope 31), which are displayed on the monitor 6.

Manual operation buttons 8e are graphically displayed on the display screen of the operation panel 8. The manual operation buttons 8e allow the operator to send instructions to the system controller 5 for making the VTR start recording the first image and/or second image on a video tape or for stopping the record of the first image and/or second image thereon.

Manual operation buttons 8f are graphically displayed on the display screen of the operation panel 8. The manual operation buttons 8f permit the operator to adjust light intensity of the illumination light irradiated from the first light source 22 and that of the illumination light irradiated from the second light source 32.

Figure 3:
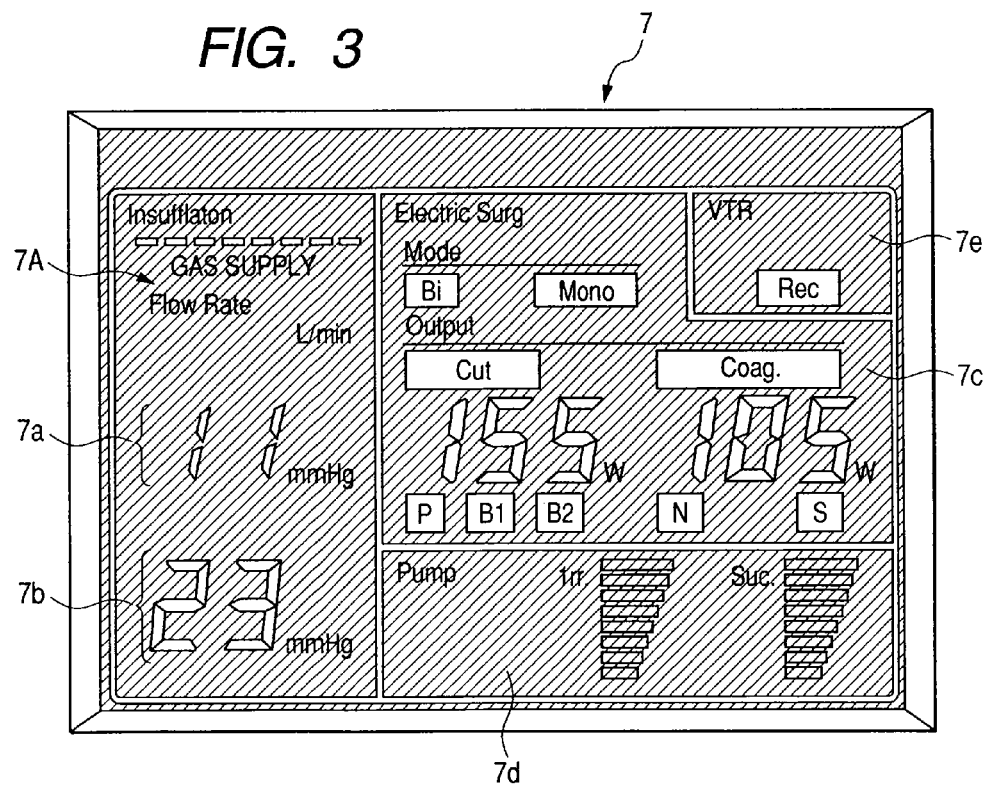
FIG. 3 is a view schematically illustrating an example of a display panel illustrated in FIG. 1.

An example of the display panel 7 shown in FIG. 1 is illustrated in FIG. 3.

As illustrated in FIG. 3, display areas 7A (7a, 7b), 7c, 7d, and 7e are graphically represented on the display screen of the display panel 7. The display areas 7A (7a, 7b), 7c, 7d, and 7e are allocated to the gas supply apparatus 41, the electric scalpel device 12, a water pump (not shown), and the VTR, which are communicated to be controlled by the system controller 5, respectively.

The current settings of the peripheral devices and the operating states thereof are displayed on the corresponding display areas 7A, (7a, 7b), 7c, 7d and 7e, respectively. For example, the display area 7A is operative to display the settings and the operating state of the gas supply apparatus 41. Specifically, the display area 7A includes a display area 7a on which a current pressure inside the lumen BC of the patient 10 is displayed, and a display area 7b on which a current pressure inside the abdominal cavity AC of the patient 10 is displayed. The display area 7A also includes display areas for displaying the flow-rate (FLOW LATE) of the carbon dioxide gas supplied from the gas supply apparatus 41 and the volume (GAS SUPPLY) of the carbon dioxide gas remaining in the $CO_2$ bottle 42.

In addition, the gas supply apparatus 41 includes a front panel FP attached along, for example, one side of a housing of the gas supply apparatus 41. The gas supply apparatus 41 also includes a manually operable setting section 63 and a display section 64, which are provided on the front panel FP.

Figure 4:
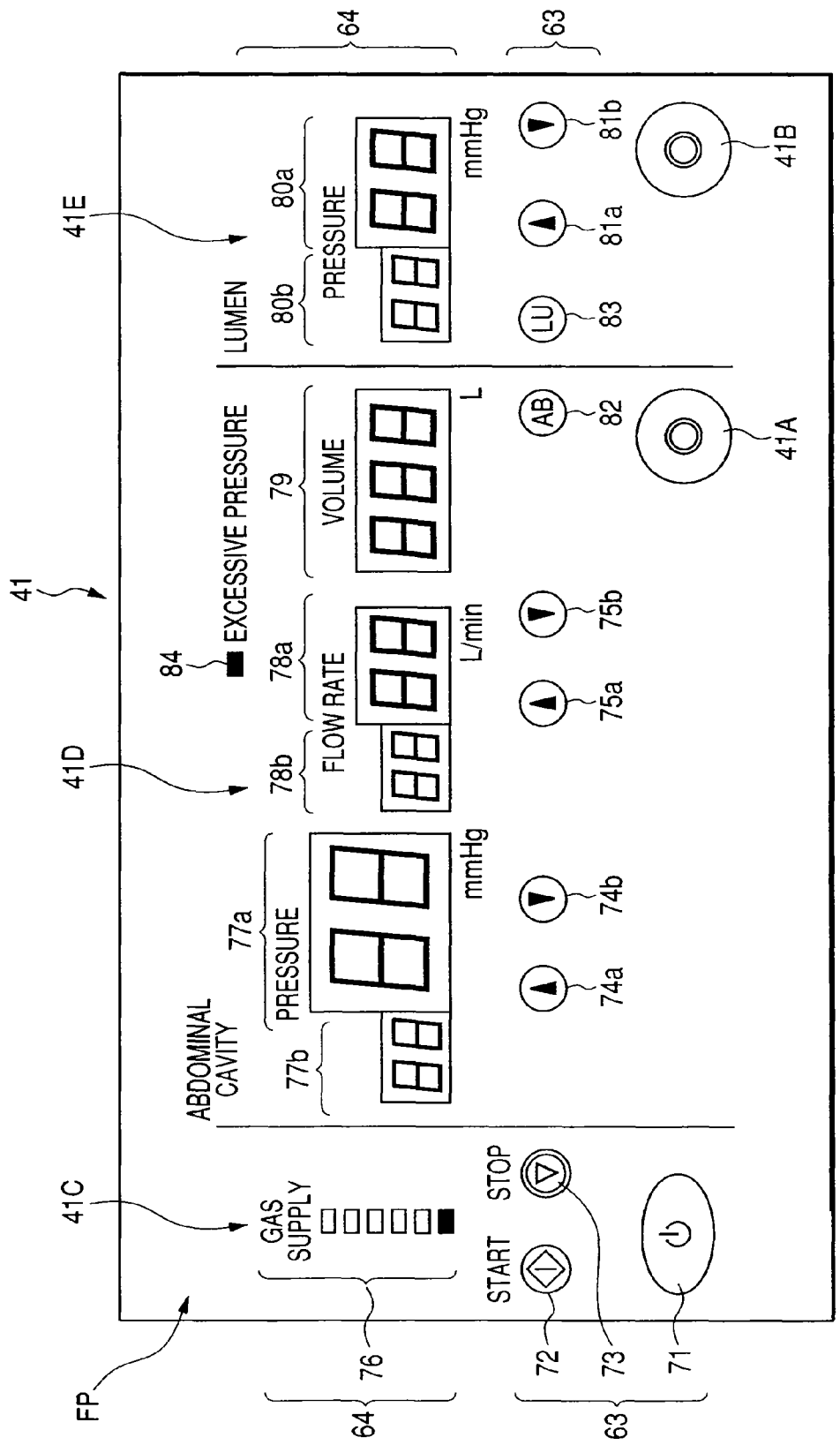
FIG. 4 is a view schematically illustrating a configuration example of a manually operable setting section and a display section provided on a front panel of the gas supply apparatus illustrated in FIG. 1.

Next, a configuration example of the manually operable setting section 63 and the display section 64 is described with reference to FIG. 4. As shown in FIG. 4, the manually operable setting section 63 and the display section 64 are, for example, graphically displayed on the front panel FP of the gas supply apparatus 41. The manually operable setting section 63 and display section 64 are divided in, for instance, three graphical setting and display sections 41C to 41E.

The setting and display section 41C serves as a supply source setting and display section that allows the operator to enter instructions related to the carbon dioxide gas supplied from the $CO_2$ bottle 42. In addition, the setting and display section 41C is designed to display the state of carbon dioxide gas supplied from the $CO_2$ bottle 42.

The setting and display section 41D serves as a setting and display section for an abdominal cavity. Specifically, the setting and display section 41D allows the operator to set parameters related to the pressure inside the abdominal cavity AC and the carbon dioxide gas insufflation thereof. The setting and display section 41D allows the operator to enter instructions related to the pressure inside the abdominal cavity AC and the carbon dioxide gas insufflation thereof. The setting and display section 41D is designed to display the state of the abdominal cavity AC depending on the carbon dioxide gas being insufflated thereinto.

The setting and display section 41E serves as a setting and display section for lumens. Specifically, the setting and display section 41E allows the operator to set parameters related to the carbon dioxide gas insufflation of the lumen BC; the setting and display section 41E is designed to display the state of the lumen BC depending on the carbon dioxide gas being insufflated thereinto.

The first adaptor 41A is attached to the lower side of the setting and display section 41D of the front panel FP; the second adaptor 41B is attached to the lower side of the setting and display section 41E of the front panel FP.

The setting and display section 41C is provided with a power switch 71, a gas-supply start button 72, and a gas-supply stop button 73a as the manually operable setting section 63. In addition, the setting and display section 41C is provided with a gas remaining volume indicators 76 as the display section 64.

The setting and display section 41D is provided with pressure displays 77a and 77b for the pressure inside the abdominal cavity AC, flow-rate displays 78a and 78b for the abdominal cavity AC, a total volume display 79 for the abdominal cavity AC, and an excessive pressure indicator 84 for the abdominal cavity AC as the display section 64.

The setting and display section 41D is provided with pressure setting buttons 74a and 74b for the pressure inside the abdominal cavity AC, flow-rate setting buttons 75a and 75b for the abdominal cavity AC, and an abdominal cavity select button 82 (see "AB" in FIG. 4) as the manually operable setting section 63.

The setting and display section 41E is provided with pressure displays 80a and 80b for the lumen BC as the display section 64.

The setting and display section 41E is provided with pressure setting buttons 81a and 81b for the lumen BC and a lumen select button 83 (see "LU" in FIG. 4) as the manually operable setting section 63.

The power switch 71 serves as a switch that permits the operator to turn power on and off the apparatus 41. The gas-supply start button 72 serves as a button that allows the operator to send an instruction to start the supply of the carbon dioxide gas into the abdominal cavity AC to a controller 98 described hereinafter. The gas-supply stop button 73 serves as a button that permits the operator to send an instruction to stop the supply of the carbon dioxide gas to the controller 98.

The pressure setting buttons 74a and 74b allow the operator to send instructions to change the corresponding parameter (the pressure inside the abdominal cavity AC) to a pressure setting. The flow-rate setting buttons 75a and 75b enable the operator to send instructions to change the corresponding parameter (the flow-rate of the carbon dioxide gas to be delivered into the abdominal cavity AC) to a flow-rate setting. The pressure setting buttons 81a and 81b permit the operator to send instructions to change the corresponding parameter (the pressure inside the lumen BC) to a flow-rate setting.

Specifically, the pressure setting buttons include an up button 74a and a down button 74b. Every time the operator clicks the up button 74a, the pressure setting inside the abdominal cavity AC turns up; every time the operator clicks the down button 74b, the pressure setting turns down. The pressure setting variably determined by the up and down buttons 74a and 74b is sent to the controller 98 every time at least one of the up and down buttons 74a and 74b is operated.

Similarly, the flow-rate setting buttons include an up button 75a and a down button 75b. The flow-rate setting of the carbon dioxide gas to be insufflated into the abdominal cavity AC turns up every time the operator clicks the up button 75a; the flow-rate setting turns down every time the operator clicks the down button 75b. The flow-rate setting variably set by the up and down buttons 75a and 75b is sent to the controller 98 every time at least one of the up and down buttons 75a and 75b is operated.

Furthermore, the pressure setting buttons include an up button 81a and a down button 81b. The pressure setting of the carbon dioxide gas to be insufflated into the lumen BC turns up every time the operator clicks the up button 81a; the pressure setting turns down every time the operator clicks the down button 81b. The pressure setting variably set by the up and down buttons 81a and 81b is sent to the controller 98 every time at least one of the up and down buttons 81a and 81b is operated.

The gas remaining volume indicators 76 are vertically arranged so that a top indicator that is lighting indicates the amount of carbon dioxide gas available.

The right-side pressure display 77a is configured to display a pressure value (in mmHg) based on a measured value of a first pressure sensor 95A described hereinafter. The left-side pressure display 77b is configured to display the pressure setting determined based on operations of, for example, the pressure setting buttons 74a and 74b.

The right-side flow-rate display 78a is configured to display a flow-rate (in L/min) based on a measured value of a first flow-rate sensor 96A described hereinafter. The left-side flow-rate display 78b is configured to display the flow-rate setting determined based on operations of, for example, the flow-rate setting buttons 75a and 75b.

The total volume display 79 is configured to display a total amount of carbon dioxide gas calculated by the controller 98 based on the measured values of the first flow-rate sensor 96A and the second flow-rate sensor 96B.

The right-side pressure display 80a is configured to display a pressure (in mmHg) based on a measured value of a second pressure sensor 95B described hereinafter. The left-side pressure display 80b is configured to display the pressure setting determined based on operations of, for example, the pressure setting buttons 81a and 81b.

When the operator turns on the abdominal cavity select button 82, the button 82 is configured to send to the controller 98 an instruction to make it execute operations for supplying the carbon dioxide gas into the abdominal cavity AC. In other words, when the operator turns on the abdominal cavity select button 82, the button 82 is configured to send to the controller 98 an instruction to change the operation mode thereof to an abdominal cavity insufflation mode.

When the operator turns on the lumen select button 83, the button 83 is configured to send to the controller 98 an instruction to make it execute operations for supplying the carbon dioxide gas into the lumen BC. In other words, when the operator turns on the lumen select button 83, the button 83 is configured to send to the controller 98 an instruction to change the operation mode thereof to a lumen insufflation mode.

The excessive pressure indicator 84 consists of, for example, red LED (light emitting device). The excessive pressure indicator 84 works to turn on or flash on and off based on a control signal sent from the controller 98 at anytime the pressure measured by the first pressure sensor 95A exceeds a threshold value of the pressure inside the abdominal cavity AC by a predetermined pressure. The turning-on or the flashing of the excessive pressure indicator 84 allows the operator to visually recognize that the pressure inside the abdominal cavity AC exceeds the threshold value by the predetermined pressure or more.

Incidentally, an excessive pressure indicator that is the same as the excessive pressure sensor 84 may be provided on the setting and display section 41E. The excessive pressure indicator works to turn on or flash on and off based on a control signal sent from the controller 98 at anytime the pressure measured by the second pressure sensor 95B exceeds a threshold value of the pressure inside the lumen BC by a predetermined pressure.

In addition, the center operation panel 8 allows the operator to set the parameters of the gas supply apparatus 41, which include the settings of the pressures inside the abdominal cavity AC and the lumen BC, and the setting of the flow-rate for the abdominal cavity AC. Specifically, the settings determined on the center operation panel 8 for the corresponding parameters are sent to the controller 98 through the system controller 5. The controller 98 carries out abdominal-cavity pressure control, luminal-pressure control, and abdominal-cavity flow-rate control based on the corresponding parameters, respectively.

The center display panel 7 can be configured to display at least one of the settings, which has been specified by the operator, displayed on the pressure displays 77a, 77b, 80a and 80b, flow-rate displays 78a and 78b, and the total volume display 79.

Specifically, the controller 98 operates to send at least one of the settings, which has been specified by the operator, displayed on the pressure displays 77a, 77b, 80a, and 80b, flow-rate displays 78a and 78b, and the total volume display 79 to the system controller 5. The system controller 5 receives at least one of the settings sent from the controller 98 to display it on the center display panel 7.

The structures of the manually operable setting section 63 and the display section 64 in the front panel FP allow the operator to easily give instructions to the controller 98 and to easily visually recognize the parameters related to the abdominal cavity AC and the lumen BC.

Next, a structure of the gas supply apparatus 41 will be described hereinafter with reference to FIG. 5.

Figure 5:
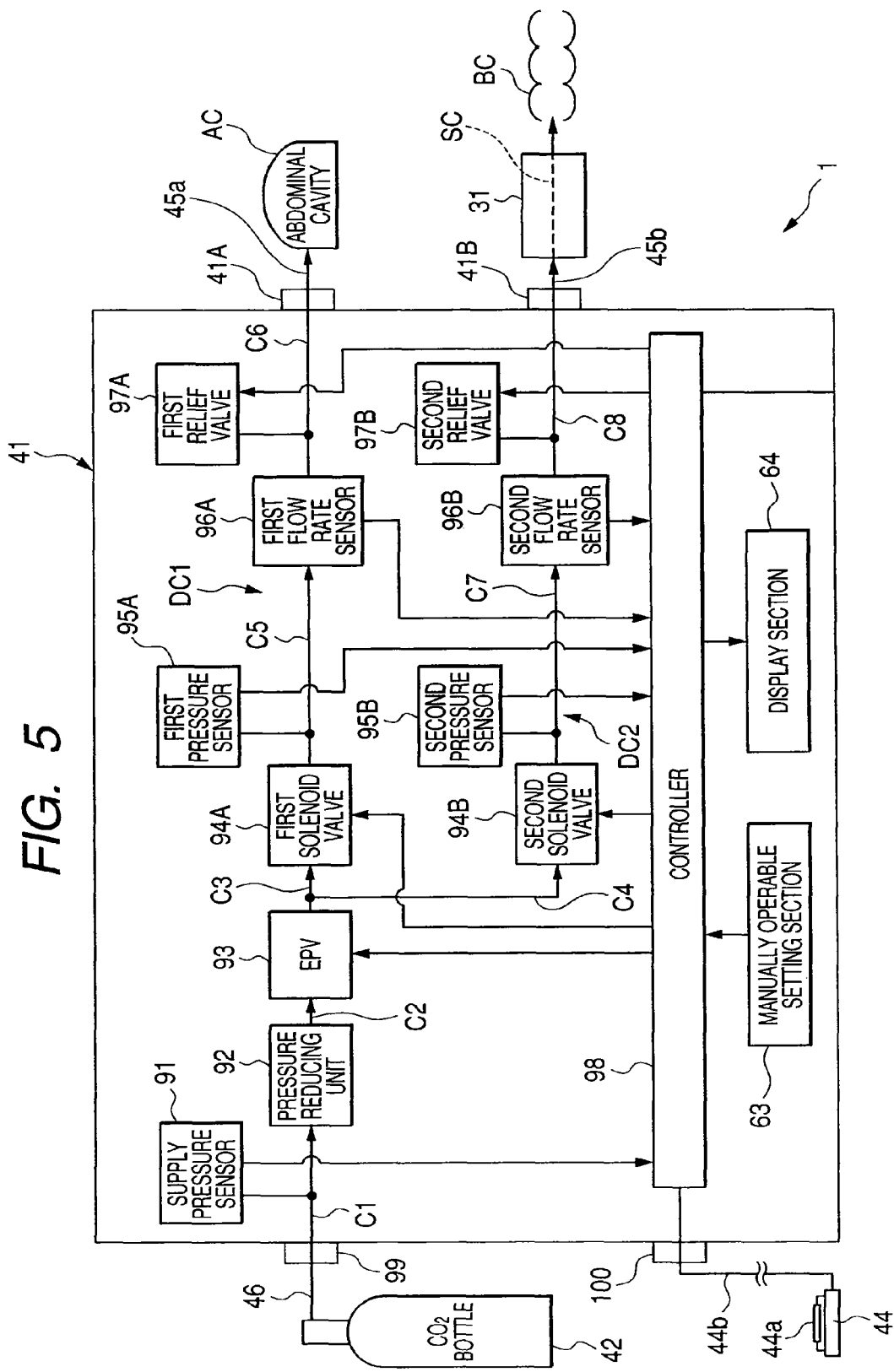
FIG. 5 is a block diagram illustrating a schematic structure of the gas supply apparatus illustrated in FIG. 1.

As shown in FIG. 5, the gas supply apparatus 41 includes a high pressure adapter 99, a first delivery channel C1, a supply pressure sensor 91, and a pressure reducing unit 92 serving as, for example, a pressure regulator. The gas supply apparatus 41 includes a second delivery channel C2, an electropneumatic proportional valve (EPV) 93 as an example of pressure regulating valves, serving as the pressure regulator, a third delivery channel C3, and a fourth delivery channel C4.

In addition, the gas supply apparatus 41 includes first and second electromagnetic valves (solenoid valves) 94A and 94B as examples of open/close valves. The first and second electromagnetic valves 94A and 94B serve as the pressure regulator.

The gas supply apparatus 41 includes a fifth delivery channel C5, a sixth delivery channel C6, the first and second pressure sensors 95A and 95B, the first flow-rate sensor 96A, and a second flow-rate sensor 96B. Moreover, the gas supply apparatus 41 includes a seventh delivery channel C7, an eighth delivery channel C8, first and second relief valves 97A and 97B, the controller 98, the manually operable setting section 63, the display section 64, and the first and second adapters 41A and 41B.

Specifically, the $CO_2$ bottle 42 has a discharge port (cock) to which one end of the high-pressure gas tube 46 is joined. The other end of the high-pressure gas tube 46 is joined to the high-pressure adapter 99. The high-pressure adapter 99 is joined to an inlet of the pressure reducing unit 92 via the first delivery channel C1. The supply pressure sensor 91 is attached to the first delivery channel C1. An outlet of the pressure reducing unit 92 is coupled to an inlet of the electropneumatic proportional valve 93 via the second delivery channel C2. An outlet of the electropneumatic proportional valve 93 is branched into the third delivery channel C3 for the abdominal cavity AC and the fourth delivery channel C4 for the lumen BC.

One branched channel C3 is coupled to an inlet of the first solenoid valve 94A. An outlet of the first solenoid valve 94A is coupled to the fifth delivery channel C5 to which the first pressure sensor 95A is attached. The fifth delivery channel C5 is coupled to an inlet of the first flow rate sensor 96A whose outlet is coupled through the sixth delivery channel C6 and the first adapter 41A to the one end of the first tube 45a. The other end of the first tube 45a is coupled to the third trocar 16, and the third trocar 16 is inserted into the abdominal cavity AC of the patient 10.

The other branched channel C4 is coupled to an inlet of the second solenoid valve 94B via the seventh delivery channel C7. An outlet of the second solenoid valve 94B is coupled to the eighth delivery channel C8. The eighth delivery channel C8 is coupled to an inlet of the second flow rate sensor 96B whose outlet is communicably coupled through the eighth delivery channel C8 to the second adapter 41B. The second adapter 41B is coupled to the one end of the second tube 45b. The other end of the tube 45b is communicably coupled to the gas delivery channel SC formed inside the flexiblescope 31 through the tube coupler 43a, and the insertion portion 34 of the flexiblescope 31 is inserted into the lumen BC of the patient 10.

In the first embodiment, the third delivery channel C3, the first solenoid valve 94A, the fifth delivery channel C5, the first flow-rate sensor 96A, the sixth delivery channel C6, the first adapter 41A, and the first tube 45a constitute a first $CO_2$ supply path DC1 directing the carbon dioxide gas into the abdominal cavity AC. Specifically, the first solenoid valve 94A is provided in the first $CO_2$ supply path DC1.

Similarly, the fourth delivery channel C4, the second solenoid valve 94B, the seventh delivery channel C7, the second flow-rate sensor 96B, the eighth delivery channel C8, the second adapter 41B, and the lumen tube 45b constitute part of a second CO2 supply path DC2. The second CO2 supply path DC2 is configured to direct the carbon dioxide gas into the lumen BC. Specifically, the second solenoid valve 94B is provided in the second CO2 supply path DC2.

The gas supply apparatus 41 has the foot switch cable 44b electrically connected to a switch connector 100; the foot switch cable 44b is electrically connected to the foot switch 44. The switch connector 100 is electrically connected to the controller 98. With the electrical connection between the foot switch 44 and the controller 98, the depressing operation of the switch portion 44a by the operator allows the instruction to be provided through the foot switch cable 44b to the controller 98. Incidentally, communications between the foot switch 44 and the controller 98 can be wirelessly established.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46, the high pressure adapter 99, and the first delivery channel C1 of the gas supply apparatus 41. The carbon dioxide gas is reduced in pressure by the pressure reducing unit 92 to have a predetermined pressure, and thereafter, guided via the second delivery channel C2 to the electropneumatic proportional valve 93. The electropneumatic proportional valve 93 regulates the pressure of the carbon dioxide gas to a pressure within a range suitable for supply into the inside of the abdominal cavity AC or that of the lumen BC.

More particularly, the electropneumatic proportional valve 93 is provided with a solenoid composed of, for example, a magnet coil (solenoid coil) and a compass needle, which are not shown. The electropneumatic proportional valve 93 is provided with a thin film for pressure control, and a pressure reducing spring. The solenoid is electrically connected to the controller 98. The electropneumatic proportional valve 93 is configured such that the solenoid controls force applied on the thin film by the pressure reducing spring depending on a control signal applied from the controller 98, thereby regulating the pressure of the carbon dioxide gas.

Specifically, the electropneumatic proportional valve 93 is designed to change its opening in proportional to a voltage or a current as the control signal applied from the controller 98 so as to regulate the pressure and the flow-rate of the carbon dioxide gas flowing therethrough within the corresponding appropriate ranges, respectively For example, the electropneumatic proportional valve 93 allows the pressure of the carbon dioxide gas to be regulated within a range from 0 to 500 mmHg based on the control signal applied from the controller 98.

For example, the range of the pressure of the carbon dioxide gas to be insufflated into the abdominal cavity AC is preferably 0 to 80 mmHg or thereabout; the range of the flow-rate thereof to be insufflated thereinto is preferably 0.1 to 35 L/min (minute) or thereabout. Moreover, for example, the range of the pressure of the carbon dioxide gas to be insufflated into the lumen BC is preferably 0 to 500 mmHg or thereabout; the range of the flow-rate thereof to be insufflated thereinto is preferably 1 to 3 L/min or thereabout.

The carbon dioxide gas whose pressure is regulated by the electropneumatic proportional valve 93 is divided into two components, and they are introduced into the third and fourth delivery channels C3 and C4, respectively. The third and fourth delivery channels C3 and C4 constitute bifurcating cannels, respectively. The divided parts of the carbon dioxide gas are introduced into two supply paths constituting the first $CO_2$ supply path DC1 directing the carbon dioxide gas into the abdominal cavity AC and the second $CO_2$ supply path DC2 directing it into the lumen BC, respectively.

Specifically, the downstream side of the electropneumatic proportional valve 93 is separated into the first $CO_2$ supply path DC1 and the second $CO_2$ supply path DC2 through the third and fourth delivery channels C3 and C4.

Incidentally, in the first embodiment, a first delivery member of the present invention corresponds to at least the fifth and sixth delivery channels C5 and C6 in the first $CO_2$ supply path DC1. Specifically, the concept of the first delivery member of the present invention can expand to cover the whole of the first $CO_2$ supply path DC1 depending on aspects of the gas supply apparatus 41.

Likewise, in the first embodiment, a second delivery member of the present invention corresponds to at least the seventh and eighth delivery channels C7 and C8 in the second $CO_2$ supply path DC2. Specifically, the concept of the second delivery member of the present invention can expand to cover the whole of the second $CO_2$ supply path DC2 depending on aspects of the gas supply apparatus 41.

The supply pressure sensor 91 is electrically connected to the controller 98. The supply pressure sensor 91 has a function of detecting the pressure of the carbon dioxide gas flowing from the $CO_2$ bottle 42 through the first delivery channel C1 to send the detected result (detected pressure value) to the controller 98.

The first pressure sensor 95A is electrically connected to the controller 98. The first pressure sensor 95A has a function of measuring a pressure in the fifth delivery channel C5, in other words, a pressure inside the abdominal cavity AC, thereby sending the measured result to the controller 98.

The second pressure sensor 95B is electrically connected to the controller 98. The second pressure sensor 95B has a function of measuring a pressure in the seventh delivery channel C7, in other words, a pressure inside the lumen BC thereby sending the measured result to the controller 98.

Each of the first and second solenoid valves 94A and 94B is electrically connected to the controller 98 and configured to open and close based on control signals sent from the controller 98. The opening and closing of the first solenoid valve 94A allow first $CO_2$ supply path DC1 to open and close, respectively. Similarly, the opening and closing of the second solenoid valve 94B permit the second $CO_2$ supply path DC2 to open and close, respectively.

The first and second flow rate sensors 96A and 96B are electrically connected to the controller 98. The first flow rate sensor 96A has a function of detecting the flow rate of the carbon dioxide gas flowing through the first solenoid valve 94A and the fifth delivery channel C5. Similarly, the second flow rate sensor 96B is operative to detect the flow rate of the carbon dioxide gas flowing through the second solenoid valve 94B and the seventh delivery channel C7. Each of the first and second flow rate sensors 96A and 96B is operative to send the detected result to the controller 98.

Furthermore, the first relief valve 97A is disposed at the midstream of the sixth delivery channel C6 between the first flow rate sensor 96A and the first adapter 41A. The first relief valve 97A is electrically connected to the controller 98. The first relief valve 97A is operative to remain in a closed state, and to open based on a control signal sent from the controller 98. The opening of the first relief valve 97A causes carbon dioxide gas in the abdominal cavity AC to be released, thereby reducing a pressure inside the abdominal cavity AC.

Similarly, the second relief valve 97B is disposed at the midstream of the eighth delivery channel C8 between the second flow rate sensor 96B and the second adapter 41B. The second relief valve 97B is electrically connected to the controller 98. The second relief valve 9713 is operative to remain in a closed state, and to open based on a control signal sent from the controller 98. The opening of the second relief valve 97B causes carbon dioxide gas in the lumen BC to be released, thereby reducing a pressure inside the lumen BC.

The controller 98 is operative to receive the measured values outputted from the supply pressure sensor 91, the first and second pressure sensors 95A and 95B, the first and second flow rate sensors 96A and 96B. The controller 98 is, for example, operative to execute opening control (pressure control) of the electropneumatic proportional valve 93, opening and closing controls of each of the first and second solenoid valves 94A and 94B, and display control of the display section 64 based on the received measured values.

In addition, the manually operable setting section 63 is electrically connected to the controller 98. The controller 98 is operative to execute opening control (pressure control) of the electropneumatic proportional valve 93, opening and closing controls of each of the first and second solenoid valves 94A and 94B, and display control of the display section 64 based on the instructions sent from the manually operable setting section 63.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46, the high pressure adapter 99, and the first delivery channel C1 of the gas supply apparatus 41. The carbon dioxide gas is reduced in pressure by the pressure reducing unit 92 to have the predetermined pressure. Thereafter, the carbon dioxide gas is delivered to the electropneumatic proportional valve 93 so that the pressure and flow-rate are regulated based on the control signals sent from the controller 98.

The carbon dioxide gas with its pressure and flow-rate regulated is selectively switched to either the first $CO_2$ supply path DC1 or the second $CO_2$ supply path DC2. The carbon dioxide gas, which is switched to the first $CO_2$ supply path DC1, is supplied into the abdominal cavity AC therethrough; the carbon dioxide gas, which is switched to the second $CO_2$ supply path DC2, is supplied into the lumen BC therethrough.

Incidentally, in the first embodiment, the channels and the like constituting the first $CO_2$ supply path DC1 provide airtight junction therebetween, and the channels and the like constituting the second $CO_2$ supply path DC2 provide airtight junction therebetween.

In the first embodiment, as shown in FIG. 1, the adapter 43 corresponds to the communicable connecting location of the second tube 45b with respect to the gas delivery channel SC inside the manipulator 35. This configuration allows the adapter 43 to be arranged at a position closer to the insertion section 34 than the gas and water supply switch 35a through which the through hole is formed.

Specifically, in the first embodiment, the through hole of the gas and water supply switch 35a of the manipulator 35 of the flexiblescope 31 deviates from the second $CO_2$ supply path DC2 including the second tube 45b through which the carbon dioxide gas is supplied. Thus, in the first embodiment, the operator is able to perform the operations to supply the carbon dioxide gas into the lumen BC and to interrupt the supply thereof by the operations to depress the switch portion 44a of the foot switch 44 and release it without opening and closing the through hole in the switch 35a.

Next, operations of the gas supply apparatus 41 according to the first embodiment will be described hereinafter.

When using the gas supply apparatus 41, a health worker, such as a nurse, prepares the first tube 45a to couple the one end of the tube 45a to the first adapter 41A of the gas supply apparatus 41 and the other end thereof to the third trocar 16. Next, the health worker attaches the adapter 43 to the base 38 of the flexiblescope 31, and prepares the second tube 45b to couple the one end of the tube 45b to the second adapter 41B of the gas supply apparatus 41 and the other end thereof to the tube coupling portion 43a of the adapter 43.

Subsequently, before surgery, the health worker opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 41. The gas flowing into the apparatus 41 is introduced through the first delivery channel C1 to the pressure reducing unit 92.

The carbon dioxide gas is reduced in pressure by the pressure reducing unit 92 to have the predetermined pressure, thereby being guided via the second delivery channel C2 to the inlet of the electropneumatic proportional valve 93.

Under a state before surgery, the electropneumatic proportional valve 93 remains closed, which causes the carbon dioxide gas not to flow the downstream thereof.

Next, the power switch 71 is turned on by, for example, the operator. In response to the turning-on of the switch 71, the measured value by the first pressure sensor 95A is displayed on the pressure display 77a of the front panel FP, and the measured value by the second pressure sensor 95B is displayed on the pressure display 80a thereof. In addition, the foot switch 44 becomes a state that allows the operator to operate it.

On the pressure display 77b, the pressure setting for the abdominal cavity AC, which has been previously set on, for example, the center operation panel 8, is displayed. Similarly, on the flow-rate display 78b, the flow-rate setting of the carbon dioxide gas to be insufflated into the abdominal cavity AC, which has been previously set on, for example, the center operation panel 8, is displayed.

Furthermore, on the pressure display 80b, the pressure setting for the lumen BC, which has been previously set on, for example, the center operation panel 8, is displayed.

The supply pressure sensor 91 measures the pressure supplied from the $CO_2$ bottle 42 to the pressure reducing unit 92 through the first delivery channel C1 to send the measured value to the controller 98. As a result, the controller 98 calculates the volume of the carbon dioxide gas remaining in the $CO_2$ bottle 42 to display it on the gas remaining volume indicators 76.

In cases where no pressure setting for the abdominal cavity AC has been previously determined on the center operating panel 8, the operator appropriately operates the pressure setting buttons 74a and 74b to determine the pressure setting for the abdominal cavity AC. The instruction corresponding to the pressure setting for the abdominal cavity AC is sent from the manually operable setting section 63 to the controller 98. Similarly, in cases where no flow-rate setting for insufflation of the abdominal cavity AC has been previously determined on the center operating panel 8, the operator appropriately operates the flow-rate setting buttons 75a and 75b. The instruction corresponding to the flow-rate setting for insufflation of the abdominal cavity AC is sent from the manually operable setting section 63 to the controller 98.

In addition, no pressure settings for the lumen BC has been previously determined on the center operating panel 8, the operator appropriately operates the pressure setting buttons 81a and 81b to determine the pressure setting for the lumen BC. The instruction corresponding to the pressure setting for the lumen BC is sent from the manually operable setting section 63 to the controller 98.

Subsequently, under laparoscopic surgery, the operator inserts the rigidscope 21 into the inside of the abdominal cavity AC with the flexiblescope 31 being inserted into the lumen BC, such as a large intestine present in the abdominal cavity AC. The operator specifies and treats at least one site to be treated in the abdominal cavity AC and/or the lumen BC based on the first and second images picked up by the rigidscope 21 and the flexiblescope 31, respectively.

Operations of the abdominal cavity select button 82 and the gas-supply start button 72 allow the controller 98 to start carbon dioxide gas insufflation with its pressure regulated suitable for the abdominal cavity AC thereinto. Specifically, the controller 98 continuously controls the pressure and the flow-rate inside the abdominal cavity AC so that they are approximately close to the pressure setting and flow-rate setting established on the font panel FP, respectively.

On the other hand, operations of the lumen select button 83 and the foot switch 44 allow the controller 98 to start carbon dioxide gas insufflation with its pressure regulated suitable for the lumen BC thereinto. Specifically, the controller 98 continuously controls the pressure inside the lumen BC so that it is approximately close to the pressure setting established on the font panel FP.

Next, an example of control operations of the controller 98 of the gas supply apparatus 41 when insufflating the carbon dioxide gas into each of the abdominal cavity AC and the lumen BC will be described hereinafter with reference to FIG. 6.

Figure 6:
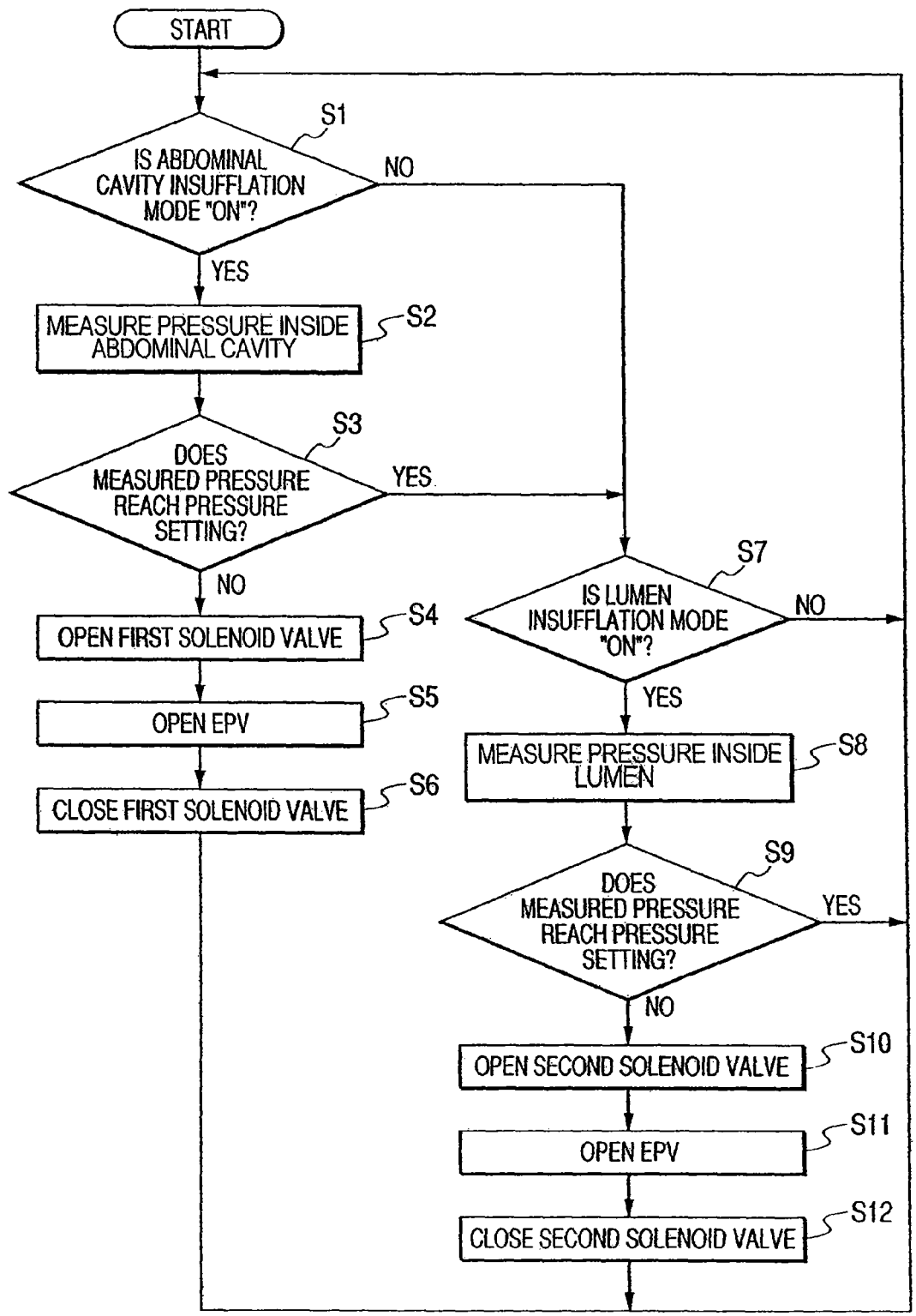
FIG. 6 is a flowchart schematically illustrating an example of control operations of a controller illustrated in FIG. 5.

At first, the controller 98 determines whether the abdominal cavity select button 82 is in on state, in other words, the operation mode thereof is the abdominal-cavity insufflation mode (FIG. 6; step S1).

When the abdominal cavity select button 82 is in on state, the controller 98 determines that its operation mode is the abdominal-cavity insufflation mode, in other words, the determination in step S1 is YES, so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open. As a result, the carbon dioxide gas supplied up to the inlet of the electropneumatic proportional valve 93 flows therethrough so that the pressure and the flow-rate of the carbon dioxide gas are regulated within the corresponding predetermined ranges suitable for the insufflation of the abdominal cavity AC. The carbon dioxide gas with the regulated pressure and flow-rate passes through the first solenoid valve 94A to be supplied into the abdominal cavity AC through the first adapter 41A, the first tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains an actual (current) pressure inside the abdominal cavity AC based on the pressure value measured by the first pressure sensor 95A with the first solenoid valve 94A closed, thereby displaying the obtained pressure on the pressure display 77a in step S2.

The controller 98 determines whether the obtained pressure reaches the pressure setting set on the front panel FP and displayed on the pressure display 77b or thereabout (step S3).

When determining that the obtained pressure does not reach the pressure setting, that is, the determination in step S3 is NO, the controller 98 calculates the difference between the obtained pressure and the pressure setting to determine a pressure reduction value of the electropneumatic proportional valve 93 based on the calculated difference.

Subsequently, the controller 98 sends the control signal to the first solenoid valve 94A to open it (step S4). Next, the controller 98 sends the control signal to the electropneumatic proportional valve 93 to open it by a predetermined opening corresponding to the determined pressure reduction value (step S5).

As a result, the carbon dioxide gas, which is reduced in pressure to the predetermined pressure by the pressure reduction unit 92, is supplied into the abdominal cavity AC through the first $CO_2$ supply path DC1. Specifically, the carbon dioxide gas is supplied through the electropneumatic proportional valve 93, the third delivery channel C3, the first solenoid valve 94A, the fifth delivery channel C5, the first flow rate sensor 96A, the sixth delivery channel C6, and the first adapter 41A. Thereafter, the carbon dioxide gas is delivered through the first tube 45a and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S5.

After a predetermined period of time has elapsed, the controller 98 sends the control signal to the first solenoid valve 94A to close it, thereby interrupting the carbon dioxide gas insufflation of the abdominal cavity AC (step S6), returning to step S1. Thus, the controller 98 repeatedly executes the carbon dioxide gas supply and interruption control operations for the abdominal cavity AC shown in steps S1 to S6 until the pressure measured by the first pressure sensor 95A in step S2 reaches the pressure setting set on the front panel FP or thereabout.

The whole of the carbon dioxide gas supply and interruption control operations for the abdominal cavity AC is referred to as "abdominal-cavity pressure control operations".

On the other hand, while the abdominal cavity select button 82 is in off state, in other words, the operation mode of the controller 98 is not in the abdominal-cavity insufflation mode (the determination in step S1 is NO), the controller 98 shifts to step S7. Similarly, when the abdominal cavity pressure reaches the pressure setting or thereabout, so that the determination in step S3 is YES, the controller 98 shifts to step S7.

In step S7, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S7 is YES so that the controller 98 enters the lumen insufflation mode.

In the lumen insufflation mode, while the switch portion 44a of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open.

As a result, the carbon dioxide gas supplied up to the inlet of the electropneumatic proportional valve 93 to flow therethrough so that the pressure and the flow-rate of the carbon dioxide gas are regulated within the corresponding predetermined ranges suitable for the insufflation of the lumen BC, respectively. The carbon dioxide gas with the regulated pressure and flow-rate passes through the second solenoid valve 94B to be supplied into the lumen BC through the second adapter 41B, the second tube 45b, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains an actual (current) pressure inside the lumen BC based on the pressure value measured by the second pressure sensor 95B with the second solenoid valve 94B closed, thereby displaying the obtained pressure on the pressure display 80a in step S8.

The controller 98 determines whether the obtained pressure reaches the pressure setting set on the front panel FP and displayed on the pressure display 80b or thereabout (step S9).

When determining that the obtained pressure does not reach the pressure setting, that is, the determination in step S9 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S10). Next, the controller 98 sends the control signal to the electropneumatic proportional valve 93 to open it by a predetermined opening corresponding to the determined pressure reduction value (step S11).

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas is supplied through the electropneumatic proportional valve 93, the fourth delivery channel C4, the second solenoid valve 94B, the seventh delivery channel C7, the second flow rate sensor 96B, the eighth delivery channel C8, and the second adapter 41B. Thereafter, the carbon dioxide gas is delivered through the second tube 45b, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S11.

After a predetermined period of time has elapsed, the controller 98 sends the control signal to the second solenoid valve 94B to close it, thereby interrupting the carbon dioxide gas insufflation of the lumen BC (step S12), returning to step S1. Thus, the controller 98 repeatedly executes the carbon dioxide gas supply and interruption control operations for the lumen BC shown in steps S1, S7 to S12 until the pressure measured by the second pressure sensor 95B in step S8 reaches the pressure setting set on the front panel FP or thereabout.

The whole of the carbon dioxide gas supply and interruption control operations for the lumen BC is referred to as "luminal-pressure control operations".

The controller 98 executes both the abdominal-cavity pressure control operations shown in steps S1 to S6 and the luminal-pressure control operations shown in steps S7 to S12. This allows the carbon dioxide gas to be insufflated into the abdominal cavity AC with its pressure regulated suitable therefor, and to be insufflated into the lumen BC with its pressure regulated suitable therefor.

Specifically, the controller 98 executes the abdominal-cavity pressure control operations shown in steps S1 to S6 when the pressure inside the abdominal cavity AC falls down from the pressure setting therefor and executes the luminal-pressure control operations shown in steps S7 to S12 when the pressure inside the lumen BC falls down from the pressure setting therefor.

Figure 7:
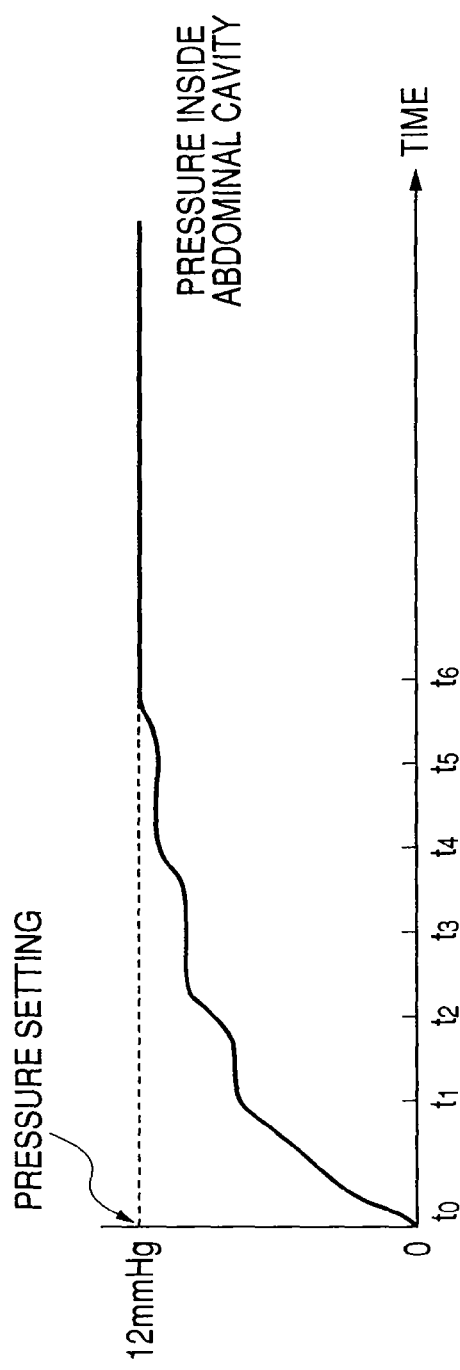
FIG. 7 is a graph schematically illustrating the change of pressure inside an abdominal cavity in time according to the first embodiment.
Figure 8:
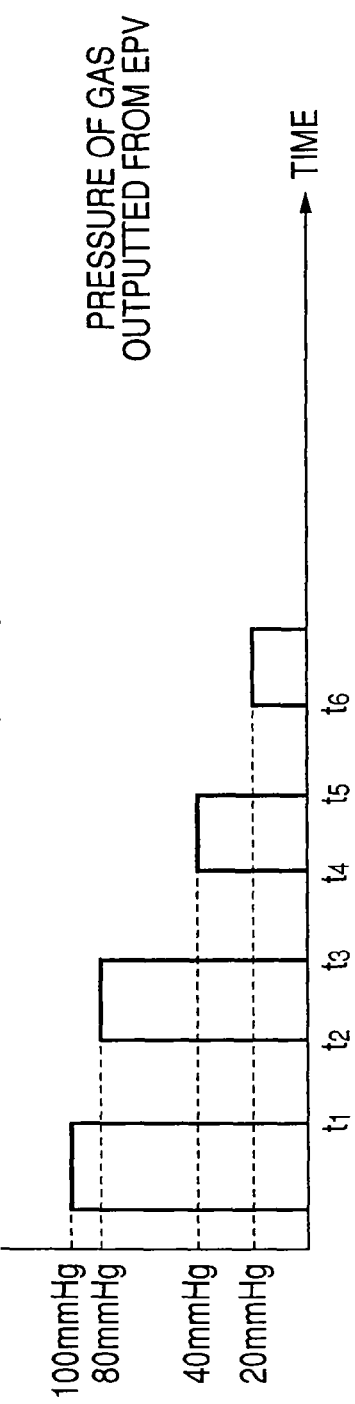
FIG. 8 is a graph schematically illustrating the change of pressure of gas outputted from an electropneumatic proportional valve and directing toward the abdominal cavity in time according to the first embodiment.

For example, in the first embodiment, the pressure inside the abdominal cavity AC is controlled as shown in FIG. 7. In the example, the pressure setting for the abdominal cavity AC set on the front panel FP is 12 mmHg. The pressure of the carbon dioxide gas outputted from the electropneumatic proportional valve 93 is regulated, for example, as shown in FIG. 8. That is, the pressure inside the abdominal cavity AC rises in time (t0, t1, . . . , t6) so that it approximately reaches the pressure setting of 12 mmHg at time t6. In addition, FIGS. 7 and 8 show that the pressure inside the abdominal cavity AC rises in time with decreasing pressure of the carbon dioxide gas outputted from the electropneumatic proportional valve 93 in time.

Figure 9:
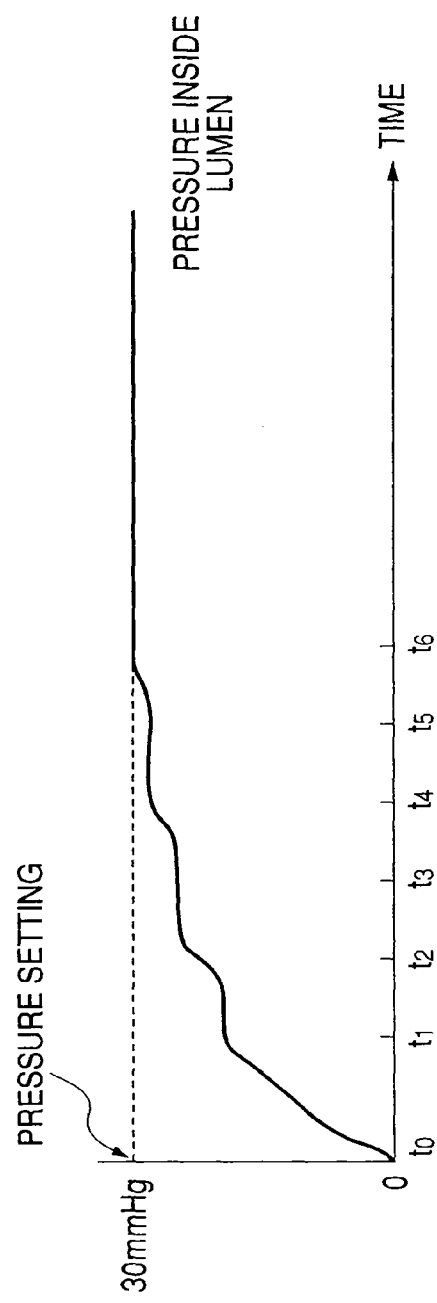
FIG. 9 is a graph schematically illustrating the change of pressure inside a lumen in time according to the first embodiment.
Figure 10:
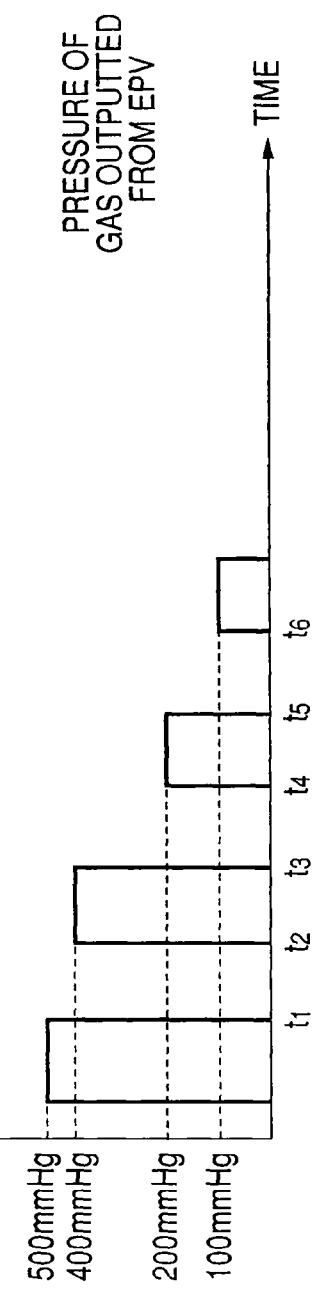
FIG. 10 is a graph schematically illustrating the change of pressure of gas outputted from the electropneumatic proportional valve and directing toward the lumen in time according to the first embodiment.

Similarly, for example, the pressure inside the lumen BC is controlled as shown in FIG. 9. In the example, the pressure setting for the lumen BC set on the front panel FP is 30 mmHg. The pressure of the carbon dioxide gas outputted from the electropneumatic proportional valve 93 is regulated, for example, as shown in FIG. 10. That is, the pressure inside the lumen BC rises in time (t0, t1, . . . , t6) so that it approximately reaches the pressure setting of 30 mmHg at time t6. In addition, FIGS. 9 and 10 show that the pressure inside the lumen BC rises in time with decreasing pressure of the carbon dioxide gas outputted from the electropneumatic proportional valve 93 in time.

As set forth above, the first embodiment allows single gas supply apparatus 41 to serve as both an insufflator and an ECR. Specifically, the gas supply apparatus 41 executes both the abdominal-cavity pressure control operations to supply the carbon dioxide gas into the abdominal cavity AC with its pressure regulated suitable therefor and the luminal-pressure control operations to supply the carbon dioxide gas into the lumen BC with its pressure regulated suitable therefor. The structure of the gas supply apparatus 41 allows expansion of the field of each of the rigidscope 21 and the flexiblescope 31 in each of the abdominal cavity AC and the lumen BC. In addition, the structure of the gas supply apparatus 41 can provide a sufficient space for manipulating treatment tools in each of the abdominal cavity AC and the lumen BC.

The first embodiment of the present invention therefore makes it possible to reduce the size and the cost of the gas supply apparatus 41, as compared with a gas supply apparatus having individually prepared insufflator and ECR.

Second Embodiment

Figure 11:
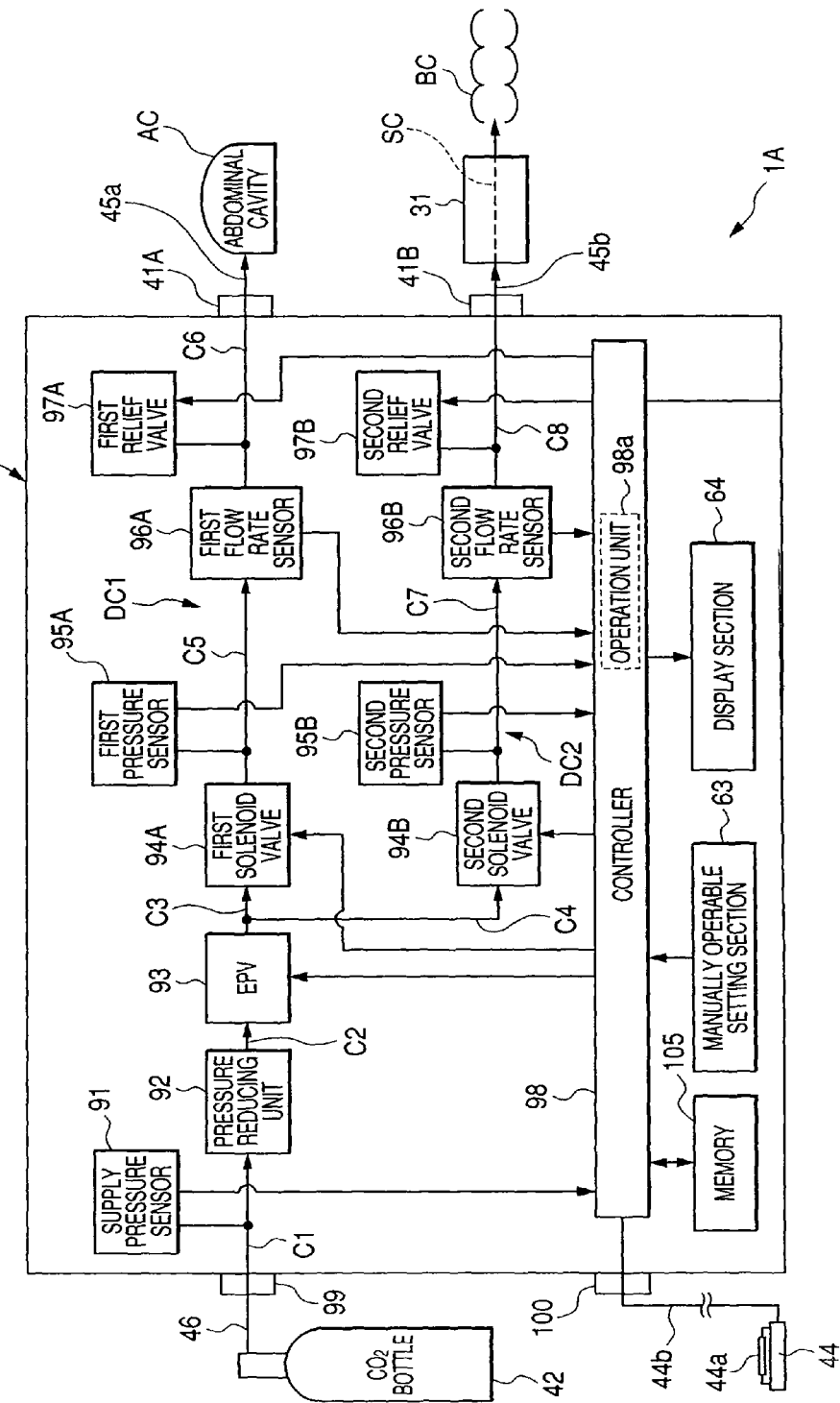
FIG. 11 is a block diagram illustrating a schematic structure of a gas supply apparatus according to a second embodiment of the present invention.

FIG. 11 is a block diagram illustrating a schematic structure of a gas supply apparatus 41K of a surgical system according to a second embodiment of the present invention.

Figure 12:
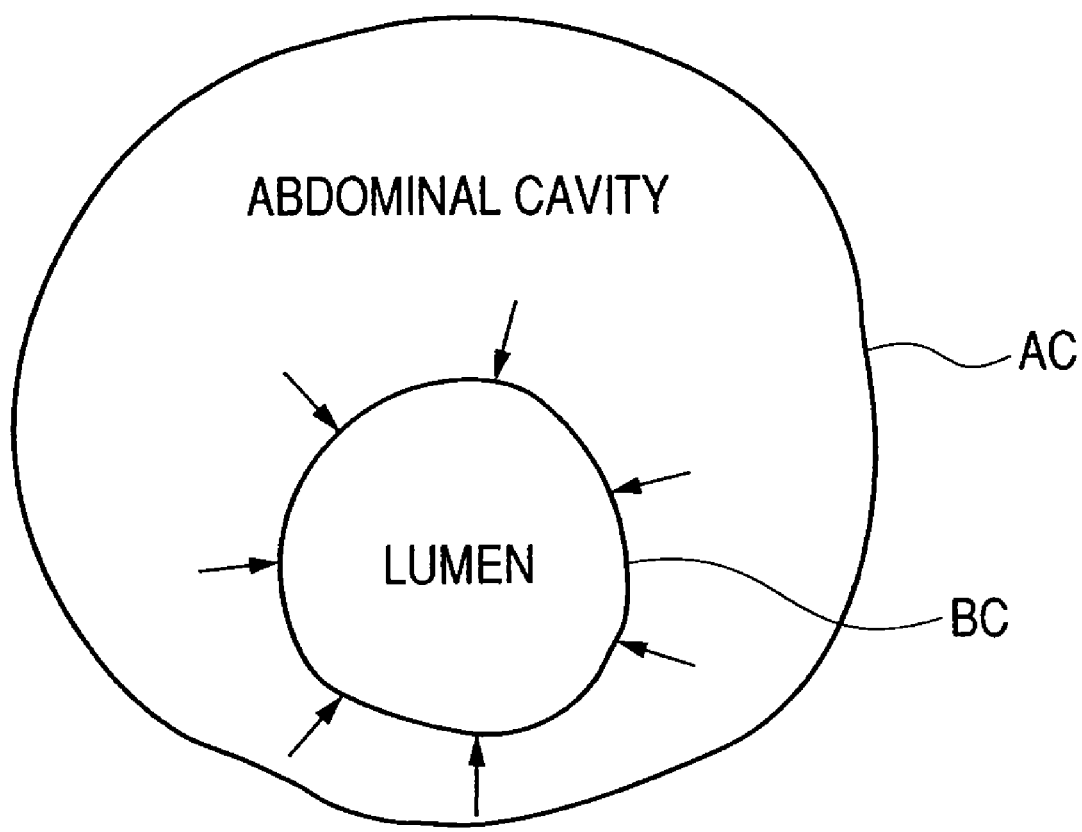
FIG. 12 is a view schematically illustrating a lumen of a patient, which is positioned in the abdominal cavity thereof according to the second embodiment of the present invention.

In the second embodiment, the lumen BC as the target of the flexiblescope 31 is located at a position affected by the pressure in the abdominal cavity AC. For example, the lumen BC may be located at a position within the abdominal cavity AC or adjacent thereto. FIG. 12 is a view schematically illustrating the lumen BC of the patient 10 is located in the abdominal cavity AC thereof according to the second embodiment of the present invention.

As illustrated in FIG. 11, the gas supply apparatus 41K according to the second embodiment is provided with a nonvolatile memory 105, such as an EEPROM (Electrically Erasable Programmable Read Only Memory), electrically connected to the controller 98.

In the second embodiment, the controller 98 has a function of storing, in the memory 105, a pressure setting inside the abdominal cavity AC displayed in the pressure display 77b as a previous value at intervals or at each time the pressure setting is updated by operation of the pressure setting buttons 74a and 74b. Similarly, the controller 98 has a function of storing, in the memory 105, a flow-rate setting for insufflation of the abdominal cavity AC displayed in the flow-rate display 78b as a previous value at intervals or at each time the flow-rate setting is updated by operation of the flow-rate setting buttons 75a and 75b.

Moreover, the controller 98 has a function of storing, in the memory 105, a pressure setting inside the lumen BC displayed in the pressure display 80b as a previous value at intervals or at each time the pressure setting is updated by operation of the pressure setting buttons 81a and 81b.

When, for example, the power switch 71 is turned off at an arbitrary timing, the pressure settings displayed on the pressure displays 77b and 80b and the flow-rate setting displayed on the flow-rate display 77b, which have been set since immediately before the turning-off of the power switch 71, are stored in the memory 105 as the previous values, respectively. Note that, when the power switch 71 is turned off, the controller 98 can store, in the memory 105, the pressure settings being displayed on the pressure displays 77b and 80b and the flow-rate setting being displayed on the flow-rate display 78b as the previous values during execution of a predetermined end processing.

Thereafter, when the power switch 71 is switched from off state to on state at an arbitrary timing, the controller 98 boots up in response to the turning on of the power switch 71. Then, the controller 98 reads out the previous values (the pressure setting for the abdominal cavity AC, the pressure setting for the lumen BC, and the flow-rate setting for the abdominal cavity AC), which have been stored in the memory 105, therefrom. Next, the controller 98 displays the readout previous values on the corresponding pressure displays 77b, 78b, and 80b as initial values, respectively.

The controller 98 has an operation unit 98a as a functional module. When any one of an instruction indicative of a desirable pressure setting for the abdominal cavity AC and that indicative of a desirable pressure setting for the lumen BC is entered into the controller 98, the operation unit 98a is operative to receive any one of the instructions. Next, the operation unit 98a is operative to calculate the pressure setting corresponding to the other of the instructions so that a current pressure inside the lumen BC is higher than that inside the abdominal cavity AC by a predetermined value.

Specifically, in the second embodiment, an operator can enter, into the controller 98, instructions indicative of desirable pressure settings for the abdominal cavity AC and the lumen BC by means of the manually operable setting section 63. The controller 98 is operative to determine the pressure setting for the lumen BC such that it is higher than the pressure setting for the abdominal cavity AC in spite of the entered instructions.

For example, in the second embodiment, every time the operator clicks the up-button 74a/down-button 74b, the manually operable setting section 63 is capable of sending, to the controller 98, a first instruction indicative of turning up/down the pressure setting displayed on the pressure display 77b by 1 mmHg. Similarly, every time the operator clicks the up-button 81a/down-button 81b, the manually operable setting section 63 is capable of sending, to the controller 98, a second instruction indicative of turning up/down the pressure setting displayed on the pressure display 80b by 1 mmHg.

When any one of the first and second instructions is entered into the controller 98, the controller 98 has a function of:

receiving any one of the first and second instructions; and updating the corresponding pressure setting currently displayed on any one of the pressure displays 77b and 80b based on any one of the first and second instructions.

In addition, the operation unit 98a of the controller 98 is operative to:

calculate the pressure setting corresponding to the other of the first and second instructions such that the pressure setting for the lumen BC is higher than that for the abdominal cavity AC by a predetermined value of, for example, 1 mmHg; and display the pressure setting for the lumen BC on the pressure display 80b based on the result of the calculation.

Note that other elements of the gas supply apparatus 41K and the surgical system according to the second embodiment are represented by the same reference characters as in the gas supply apparatus 41 and the surgical system 1 according to the first embodiment. The descriptions of the other elements of the gas supply apparatus 41K and the surgical system according to the second embodiment are therefore omitted.

Next, operations of the gas supply apparatus 41K will be described hereinafter; these operations are different from those of the gas supply apparatus 41 according to the first embodiment.

For example, after the turning-on of the power switch 71, the controller 98 operates to display the settings stored in the memory 105 on the corresponding displays 77b, 78b, and 80b as the initial values, respectively. After the turning on of the power switch 71, the settings previously determined on the center operation panel 8 can be displayed on the corresponding displays 77b, 78b, and 80b as the initial values, respectively.

When no initial values are displayed on the corresponding displays 77b, 78b, and 80b, or the initial values are desired to be updated, the operator turns on the abdominal cavity select button 82 to click the pressure setting buttons 74a/74b of the manually operable setting section 63 in order to set the pressure setting for the abdominal cavity AC. The instruction corresponding to the click of the pressure setting buttons 74a/74b is sent to the controller 98 by the manually operative setting section 63.

When the instruction corresponding to the click of the pressure setting buttons 74a/74b is sent to the controller 98, the controller 98 receives the instruction and displays, on the pressure display 77b, a new pressure setting for the abdominal cavity AC based on the received instruction in cases where no initial value is displayed on the pressure display 77b. If an initial value is displayed on the pressure display 77b, the controller 98 updates the initial value displayed on the pressure display 77b to a new pressure setting for the abdominal cavity AC based on the received instruction (step S15a1 of FIG. 13A).

After the determination of the pressure setting for the abdominal cavity AC, the operation unit 98a of the controller 98 adds the predetermined value of 1 mmHg to the displayed (updated) current pressure setting for the abdominal cavity AC (step S15a2).

In addition to the input of the information for setting the pressure setting for the abdominal cavity AC, the operator turns on the lumen select button 83. Next, the operator clicks the pressure setting buttons 81a/81b of the manually operable setting section 63 in order to set the pressure setting for the lumen BC. The instruction corresponding to the click of the pressure setting buttons 81a/81b is sent to the controller 98 by the manually operative setting section 63.

When the instruction corresponding to the click of the pressure setting buttons 81a/81b is sent to the controller 98, the controller 98 receives the instruction and displays, on the pressure display 80b, a new pressure setting for the lumen BC based on the received instruction in cases where no initial value is displayed on the pressure display 80b. If an initial value is displayed on the pressure display 80b, the controller 98 updates the initial value displayed on the pressure display 80b to a new pressure setting for the lumen BC based on the received instruction (step S15a3).

Subsequently, the operation unit 98a of the controller 98 compares the displayed (updated) pressure setting for the lumen BC with the value obtained in step S15a2 (step S15a4).

When the value obtained in step S15a2 is equal to or lower than the displayed (updated) pressure setting for the lumen BC, the controller 98 exits the operations. As a result, the pressure setting for the lumen BC obtained in step S15a3 has been continuously displayed.

In contrast, when the value obtained in step S15a2 is higher than the displayed (updated) pressure setting for the lumen BC, the controller 98 updates the pressure setting displayed on the pressure display 80b to the value obtained in step S15a2 (step S15a5).

Assuming that the pressure inside the abdominal cavity AC is set within a range from 3 to 25 mmHg for example and that a settable maximum value for the pressure inside the lumen BC is 30 mmHg, a pressure inside the lumen BC can be set within the range from SE1 +1 mmHg to 30 mmHg, where SE1 represents the pressure setting for the abdominal cavity AC.

Specifically, in the second embodiment, the controller 98 is configured to determine the pressure setting for the lumen BC so that it is not lower than the sum of the pressure setting for the abdominal cavity AC entered from the manually operable setting section 63 and the predetermined value of "1 mmHg". The sum of the entered pressure setting and the predetermined value of "1 mmHg" corresponds to the minimum value of the pressure setting for the lumen BC. The controller 98 is also configured to display the determined pressure setting for the lumen BC on the pressure display 80b.

As described in the first embodiment, the controller 98 controls a current pressure inside the lumen BC so that it reaches the pressure setting for the lumen BC displayed on the pressure display 80b while the gas supply apparatus 41K is in the lumen insufflation mode (see steps S1 and S7 to S12 in FIG. 6). These operations of the controller 98 allow an actual pressure inside the lumen BC to be constantly higher than an actual pressure inside the abdominal cavity AC by at least the predetermined value of 1 mmHg.

For another example, after the turning-on of the power switch 71 when no initial values are displayed on the corresponding displays 77b, 78b, and 80b, or the initial values are desired to be updated, the operator turns on the lumen select button 83 in order to set the pressure setting for the lumen BC. Next, the operator clicks the pressure setting buttons 81a/81b of the manually operable setting section 63 the instruction corresponding to the click of the pressure setting buttons 81a/81b is sent to the controller 98 by the manually operative setting section 63.

When the instruction corresponding to the click of the pressure setting buttons 81a/81b is sent to the controller 98, the controller 98 receives the instruction to display, on the pressure display 80b, a new pressure setting for the lumen BC based on the received instruction in cases where no initial value is displayed on the pressure display 81b. If an initial value is displayed on the pressure display 81b, the controller 98 updates the initial value displayed on the pressure display 81b to a new pressure setting for the lumen BC based on the received instruction (step S16a1 of FIG. 13B).

After the determination of the pressure setting for the lumen BC, the operation unit 98a of the controller 98 subtracts the predetermined value of 1 mmHg from the displayed (updated) current pressure setting for the lumen BC (step S16a2).

In addition to the entry of the information for setting the pressure setting for the lumen BC, the operator turns on the abdominal cavity select button 82 in order to set the pressure setting for the abdominal cavity AC. Next, the operator clicks the pressure setting buttons 74a/74b of the manually operable setting section 63 The instruction corresponding to the click of the pressure setting buttons 74a/74b is sent to the controller 98 by the manually operative setting section 63.

When the instruction corresponding to the click of the pressure setting buttons 74a/74b is sent to the controller 98, the controller 98 receives the instruction and displays, on the pressure display 77b, a new pressure setting for the abdominal cavity AC based on the received instruction in cases where no initial value is displayed on the pressure display 74b. If an initial value is displayed on the pressure display 74b, the controller 98 updates the initial value displayed on the pressure display 74b to a new pressure setting for the abdominal cavity AC based on the received instruction (step S16a3).

Subsequently, the operation unit 98a of the controller 98 compares the displayed (updated) pressure setting for the abdominal cavity AC with the value obtained in step S16a2 (step S16a4).

When the value obtained in step S16a2 is equal to or higher than the displayed (updated) pressure setting for the abdominal cavity AC, the controller 98 exits the operations. As a result, the pressure setting for the abdominal cavity AC obtained in step S16a3 has been continuously displayed.

In contrast, when the value obtained in step S16a2 is lower than the displayed (updated) pressure setting for the abdominal cavity AC, the controller 98 updates the pressure setting displayed on the pressure display 77b to the value obtained in step S16a2 (step S16a5).

As a result, assuming that SE2 represents the pressure setting for the lumen BC, the pressure setting for the abdominal cavity AC can be set within the range from 3 to SE2 −1 mmHg.

Specifically, in the second embodiment, the controller 98 is configured to determine the pressure setting for the abdominal cavity AC so that it is not higher than the value obtained by subtracting the predetermined value of 1 mmHg from the pressure setting for the lumen BC entered from the manually operable setting section 63. The value obtained by subtracting the predetermined value of 1 mmHg from the pressure setting for the lumen BC corresponds to the maximum value of the pressure setting for the abdominal cavity AC. The controller 98 is configured to display the determined pressure setting for the abdominal cavity AC on the pressure display 77b.

As described in the first embodiment, the controller 98 controls a current pressure inside the abdominal cavity AC so that it reaches the pressure setting for the abdominal cavity AC displayed on the pressure display 77b while the gas supply apparatus 41K is in the abdominal cavity insufflation mode (see steps S1 to S6 in FIG. 6). These operations of the controller 98 allow an actual pressure inside the abdominal cavity AC to be constantly lower than an actual pressure inside the lumen BC by at least the predetermined value of 1 mmHg.

In the second embodiment, it is possible to set the pressure setting for the lumen BC so as to keep it constantly higher than the pressure setting for the abdominal cavity AC by at least the predetermined value. In other words, it is possible to forcibly set the pressure setting for the lumen BC to a value obtained by adding the predetermined value to the pressure setting for the abdominal cavity AC.

The operations of the controller 98 illustrated in FIG. 6 therefore make it possible to maintain an actual pressure inside the lumen BC to be not lower than that inside the abdominal cavity AC. Even if a current pressure inside the abdominal cavity AC becomes any value, it is possible to inflate the lumen BC against the pressure inside the abdominal cavity AC. This allows the field of the flexiblescope 31 and a space to manipulate treatment tools in the lumen BC to expand.

Like the first embodiment, the second embodiment of the present invention therefore allows single gas supply apparatus 41K to serve as both an insufflator and an ECR.

Specifically, the gas supply apparatus 41K executes both the abdominal-cavity pressure control operations to insufflate the carbon dioxide gas into the abdominal cavity AC with its pressure regulated suitable therefor and the luminal-pressure control operations to insufflate the carbon dioxide gas into the lumen BC with its pressure regulated suitable therefor. This makes it possible to reduce the size and the cost of the gas supply apparatus 41K, as compared with a gas supply apparatus having individually prepared insufflator and ECR.

Third Embodiment

A configuration example of a manually operable setting section 63A and a display section 64A provided on a front panel FP1 of a gas supply apparatus 41L of a surgical system according to a third embodiment of the present invention is illustrated in FIG. 14.

In the third embodiment, like the second embodiment, the lumen BC as the target of the flexiblescope 31 is located at a position affected by the pressure in the abdominal cavity AC. For example, the lumen BC may be located at a position within the abdominal cavity AC or adjacent thereto.

One aspect of the gas supply apparatus 41K according to the second embodiment is configured to determine the pressure setting for the lumen BC so that it is higher than the pressure setting for the abdominal cavity AC by a predetermined value in order to keep an actual pressure inside the lumen BC constantly higher than that inside the abdominal cavity AC by the predetermined value.

In contrast, the manually operable setting section 63A in the front panel FP1 of the gas supply apparatus 41L is configured to allow an operator to set a pressure inside the lumen BC by which the lumen BC is expandable (inflatable) against an ambient pressure thereround; this pressure inside the lumen BC is referred to as "lumen expanding pressure".

Note that other elements of the gas supply apparatus 41L and the surgical system according to the third embodiment are represented by the same reference characters as in the gas supply apparatus 41K and the surgical system according to the second embodiment. The descriptions of the other elements of the gas supply apparatus 41L and the surgical system according to the third embodiment are therefore omitted.

Specifically, as illustrated in FIG. 14, the manually operable setting section 63A in the front panel FP1 of the gas supply apparatus 41L includes lumen expanding pressure setting buttons 81c and 81d in place of the pressure setting buttons 81a and 81b for the lumen BC. The lumen expanding pressure setting buttons 81c and 81d are provided in the setting and display section 41E.

The lumen expanding pressure setting button 81c serves as an up button that enables the operator to send, to the controller 98, instructions to gradually increase the corresponding parameter (a lumen expanding pressure setting).

The lumen expanding pressure setting button 81d serves as a down button that enables the operator to send, to the controller 98, instructions to gradually decrease the corresponding parameter (the lumen expanding pressure setting).

In addition, the display section 64A is provided with an expanding pressure display 80c in place of the pressure display 80b. The expanding pressure display 80c is configured to display the lumen expanding pressure setting set by the operations of the lumen expanding pressure setting buttons 81c and 81d. The expanding pressure display 80c is provided in the setting and display section 41E.

Because the lumen expanding pressure according to the third embodiment is a pressure by which the lumen BC is expandable against an ambient pressure therearound, the higher the lumen expanding pressure is, the more greatly the lumen BC is expanded. This allows the field of the flexible-scope 31 and a space to manipulate treatment tools in the lumen BC to expand.

Specifically, the lumen expanding pressure setting indicates how high the pressure inside the lumen BC is needed for expanding the BC against an ambient pressure therearound, in other words, indicates the tension of the lumen BC.

In the third embodiment, the pressure setting for the lumen BC is represented by the sum of the lumen expanding pressure setting and the pressure setting for the abdominal cavity AC.

Every time the operator clicks the up-button 81c/down-button 81d, the controller 98 causes the lumen expanding pressure setting displayed on the expanding pressure display 80c to increment/decrement by 1 mmHg. The settable range of the lumen expanding pressure setting has been determined as 1 to 10 mmHg.

In the third embodiment, similar to the second embodiment, the controller 98 has an operation unit 98a as a functional module. When an instruction indicative of a pressure setting for the abdominal cavity AC and that indicative of a desirable lumen expanding pressure setting are entered into the controller 98, the operation unit 98a is operative to receive the instructions. Next, the operation unit 98a is operative to calculate the pressure setting for the lumen BC so that the pressure setting for the lumen BC is higher than that for the abdominal cavity AC. That is, the operation unit 98a is operative to calculate the pressure setting for the lumen BC by adding the lumen expanding pressure setting to the pressure setting for the abdominal cavity AC.

In the third embodiment, when determining the lumen expanding pressure setting, the operator firstly turns (clicks) on the abdominal cavity select button 82 of the manually operable setting section 63A to set the operation mode of the controller 98 to the abdominal cavity insufflation mode. Next, the operator clicks the pressure setting buttons 74a/74b of the manually operable setting section 63A in order to set the pressure setting for the abdominal cavity AC.

Secondary, the operator clicks on the lumen select button 83 of the manually operable setting section 63A to turn the operation mode of the controller 98 to the lumen insufflation mode. Next, the operator clicks the pressure setting buttons 81c/81d of the manually operable setting section 63A in order to set the lumen expanding pressure setting.

Next, operations of the gas supply apparatus 41L will be described hereinafter; these operations are different from those of the gas supply apparatus 41 according to the first embodiment and the gas supply apparatus 41K according to the second embodiment.

For example, after the turning-on of the power switch 71, the controller 98 operates to display the settings stored in the memory 105 on the corresponding displays 77b, 78b, and 80c as the initial values, respectively. After the turning on of the power switch 71, the settings previously determined on the center operation panel 8 can be displayed on the corresponding displays 77b, 78b, and 80c as the initial values, respectively.

When no initial values are displayed on the corresponding displays 77b, 78b, and 80c, or the initial values are desired to be updated, the operator turns on the abdominal cavity select button 82 of the manually operable setting section 63A to click the pressure setting buttons 74a/74b in order to set the pressure setting for the abdominal cavity AC. In the third embodiment, the controller 98 can set the pressure inside the abdominal cavity AC within the range from 3 to 25 mmHg by 1 mmHg.

Figure 15:
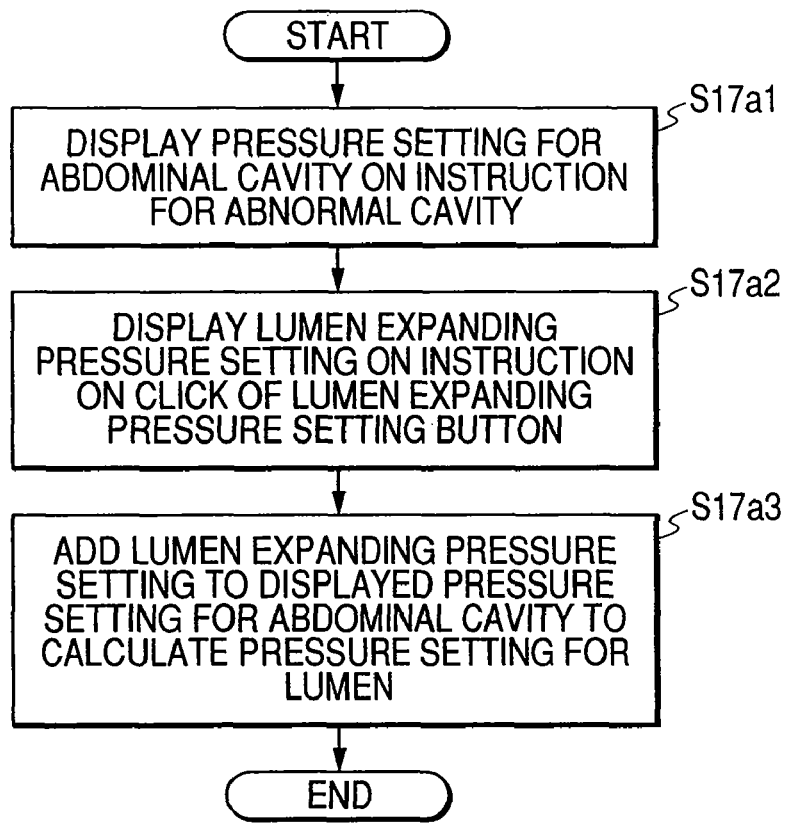
FIG. 15 is a flowchart schematically illustrating an example of control operations of a controller of the gas supply apparatus according to the third embodiment of the present invention.

When the instruction corresponding to the click of the pressure setting buttons 74a/74b is sent to the controller 98, the controller 98 receives the instruction and displays, on the pressure display 77b, a new pressure setting for the abdominal cavity AC based on the received instruction in cases where no initial value is displayed on the pressure display 77b. If an initial value is displayed on the pressure display 77b, the controller 98 updates the initial value displayed on the pressure display 77b to a new pressure setting for the abdominal cavity AC based on the received instruction (step S17a1 of FIG. 15).

Next, the operator turns on the lumen select button 83 of the manually operable setting section 63A to click the lumen expanding pressure setting buttons 81c/81d in order to set the lumen expanding pressure setting. As a result, the instruction corresponding to the click of the lumen expanding pressure setting buttons 81c/81d is sent to the controller 98.

The controller 98 receives the instruction and displays, on the expanding pressure display 80c, a new lumen expanding pressure setting based on the received instruction in cases where no initial value is displayed on the expanding pressure display 80c. If an initial value is displayed on the expanding pressure display 80c, the operation unit 98a of the controller 98 updates the initial value displayed on the expanding pressure display 80c to a new lumen expanding pressure setting based on the received instruction (step S17a2).

Subsequently, the operation unit 98a of the controller 98 adds the lumen expanding pressure setting to the displayed (updated) pressure setting for the abdominal cavity AC, thereby automatically calculating the pressure setting for the lumen BC (step S17a3).

Assuming that the pressure setting for the abdominal cavity AC, which is settable within the range from 3 to 25 mmHg, is set to 8 mmHg, and that the lumen expanding pressure setting is set to 5 mmHg, the pressure setting for the lumen BC can be calculated by the following equation: 8 (mmHg)+5 (mmHg)=13 (mmHg).

As described in the first embodiment, the controller 98 controls a current pressure inside the lumen BC so that it reaches the pressure setting for the lumen BC calculated by the operation in step S17a3 while the gas supply apparatus 41L is in the lumen insufflation mode (see steps S1 and S7 to S12 in FIG. 6). These operations of the controller 98 allow an actual pressure inside the lumen BC to be constantly higher than an actual pressure inside the abdominal cavity AC by at least the lumen expanding pressure setting.

Note that, during laparoscopic surgery, when the pressure setting for the abdominal cavity AC is changed by the clicks of the pressure setting buttons 74a/74b by the operator, the controller 98 updates the pressure setting for the abdominal cavity AC displayed on the pressure display 77b to a new pressure setting based on the instruction corresponding to the clicks of the pressure setting buttons 74a/74b (see step S17a1).

Subsequently, the operation unit 98a of the controller 98 adds the lumen expanding pressure setting displayed on the expanding pressure display 80c to the updated pressure setting for the abdominal cavity AC, thereby automatically changing the pressure setting for the lumen BC depending on the change of the pressure setting for the abdominal cavity AC (see step S17a3).

As a result, even if the pressure setting for the abdominal cavity AC is changed, it is possible to automatically change the pressure setting for the lumen BC depending on the change of the pressure setting for the abdominal cavity AC in accordance with the following equation: "the pressure setting for the lumen BC=the pressure setting for the abdominal cavity AC+the lumen expanding pressure setting".

As described above, in the third embodiment, it is possible to set the pressure setting for the lumen BC so as to keep the pressure setting for the lumen BC constantly higher than the pressure setting for the abdominal cavity AC based on the lumen expanding pressure setting. In other words, it is possible to set the pressure setting for the lumen BC to a value obtained by the sum of the pressure setting for the abdominal cavity AC and the lumen expanding pressure setting.

The operations of the controller 98 illustrated in FIG. 6 therefore make it possible to maintain an actual pressure inside the lumen BC to be higher than that inside the abdominal cavity AC.

As a result, when starting to insufflate the carbon dioxide gas into the lumen BC, the lumen BC can rapidly expand against an ambient pressure therearound, such as a pressure inside the abdominal cavity AC. This allows the operator to obtain a wide field in the lumen BC, such as the intestines of the patient 10, through the flexiblescope 31 immediately after the start of the insufflation of the lumen BC.

Especially, in the third embodiment, even if the pressure setting for the abdominal cavity AC is changed, it is possible to automatically change the pressure setting for the lumen BC depending on the change of the pressure setting for the abdominal cavity AC in accordance with the following equation: "the pressure setting for the lumen BC=the pressure setting for the abdominal cavity AC+the lumen expanding pressure setting". Therefore, even if the pressure inside the abdominal cavity AC around the lumen BC is changed, the third embodiment allows the tension (expansion) of the lumen BC to remain unchanged.

Note that, in the third embodiment, the lumen expanding pressure setting is settable by 1 mmHg, but the present invention is not limited to the structure. The manually operable setting section 63A can set a predetermined plurality of lumen expanding pressure settings, such as three settings of "a high pressure setting (HIGH)", "an intermediate pressure setting (INTERMEDIATE)", and "a low pressure setting (LOW)".

Specifically, in the third embodiment, the manually operable setting section 63 can be provided with a selector switch in place of the lumen expanding pressure setting buttons 81c and 81d. The selector switch allows the operator to enter a high pressure setting, an intermediate presser setting lower than the high pressure setting, and a low pressure setting lower than the intermediate pressure setting into the controller 98 through the manually operable setting section 63A. For example, the selector switch is movable at first, second, and third positions corresponding to the high pressure setting of, for example, 10 mmHg, the intermediate pressure setting of, for example, 5 mmHg, and the low pressure setting of, for example, 1 mmHg, respectively. Specifically, when the operator makes the selector switch move to any one of the first to third positions, the instruction indicative of any one of the high pressure setting, the intermediate pressure setting, and the low pressure setting can be sent from the manually operable setting section 63A to the controller 98.

Fourth Embodiment

Figure 16:
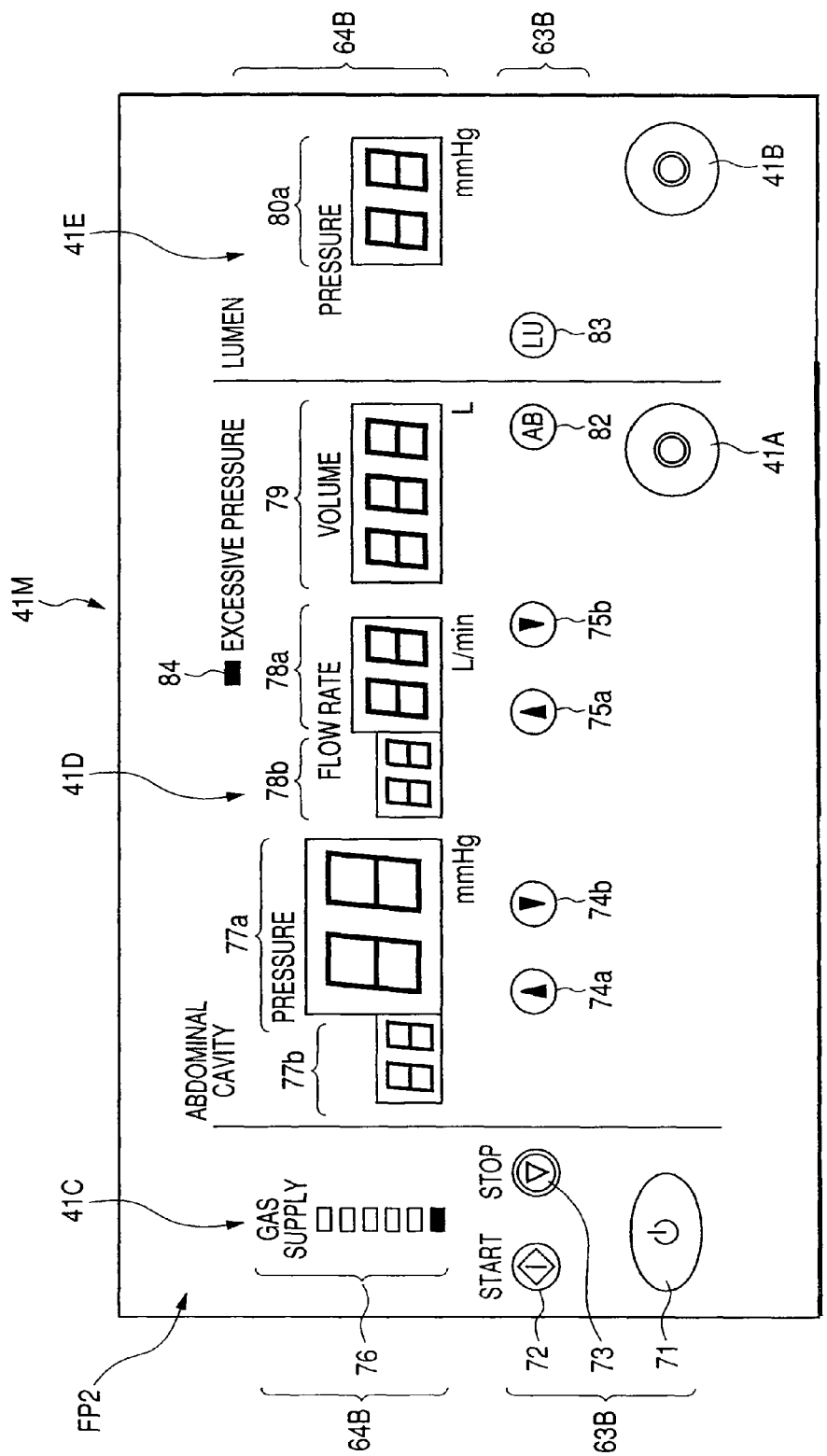
FIG. 16 is a view schematically illustrating a configuration example of a manually operable setting section and a display section provided on a front panel of a gas supply apparatus according to a fourth embodiment of the present invention.

A configuration example of a manually operable setting section 63B and a display section 64B provided on a front panel FP2 of a gas supply apparatus 41M of a surgical system according to a fourth embodiment of the present invention is illustrated in FIG. 16.

In the fourth embodiment, as well as the second and third embodiments, the lumen BC as the target of the flexiblescope 31 is located at a position affected by the pressure in the abdominal cavity AC. For example, the lumen BC may be located at a position within the abdominal cavity AC or adjacent thereto.

In the gas supply apparatuses 41K and 41L according to the second and third embodiments, a value associated with a pressure inside the lumen BC and entered by an operator through the manually operable setting section is used. The value received by the controller 98 allows the controller 98 to control an actual pressure inside the lumen BC so that it is higher than an actual pressure inside the abdominal cavity AC by a predetermined value.

In contrast, the controller 98 of the gas supply apparatus 41M is configured, when a pressure setting for the abdominal cavity AC is set by the operator through the manually operable setting section 63B, to set a pressure setting for the lumen BC based on only the pressure setting for the abdominal cavity AC.

Note that other elements of the gas supply apparatus 41M and the surgical system according to the fourth embodiment are represented by the same reference characters as in the gas supply apparatuses 41 and 41K according to the first and second embodiments. The descriptions of the other elements of the gas supply apparatus 41M and the surgical system according to the fourth embodiment are therefore omitted.

Specifically, as illustrated in FIG. 16, in the manually operable setting section 63B of the front panel FP2, the pressure setting buttons 81a and 81b and the lumen expanding pressure setting buttons 81c and 81d are omitted. In addition, in the display section 64B, the pressure displays 80b for displaying the pressure setting for the lumen BC and the pressure display 80c for displaying the lumen expanding pressure setting are also omitted.

In other words, the setting and display section 41E is provided with only the lumen select button 83 as the manually operable setting section 63B and with only the pressure display 80a as the display section 64B, this pressure display 80a is configured to display a pressure based on a measured value of the second pressure sensor 95B One of the pressure settings, which is enterable by the operator through the manually operable setting section 63B, is the pressure setting for the abdominal cavity AC. In the fourth embodiment, the pressure setting for the lumen BC is set to the sum of the pressure setting for the abdominal cavity AC, which is set by the operator through the manually operable setting section 63B, and a predetermined initial value of, for example, 5 mmHg.

Specifically, the controller 98 of the gas supply apparatus 41M has an operation unit 98a as a functional module. When an instruction indicative of a pressure setting for the abdominal cavity AC is entered into the controller 98, the operation unit 98a is operative to receive the instruction. Next, the operation unit 98a is operative to add the predetermined initial value of 5 mmHg to the received pressure setting for the abdominal cavity AC to calculate the pressure setting for the lumen BC.

Next, operations of the gas supply apparatus 41M will be described hereinafter; these operations are different from those of the gas supply apparatus 41 according to the first embodiment and the gas supply apparatus 41K according to the second embodiment.

For example, after the turning-on of the power switch 71, the controller 98 operates to display the settings stored in the memory 105 on the corresponding displays 77b and 78b as the initial values, respectively. After the turning on of the power switch 71, the settings previously determined on the center operation panel 8 can be displayed on the corresponding displays 77b and 78b as the initial values, respectively.

When no initial values are displayed on the corresponding displays 77b and 78b, or the initial values are desired to be updated, the operator turns on the abdominal cavity select button 82 of the manually operable setting section 63B to click the pressure setting buttons 74a/74b in order to set the pressure setting for the abdominal cavity AC. In the fourth embodiment, the controller 98 can set the pressure inside the abdominal cavity AC within the range from 3 to 25 mmHg by 1 mmHg.

Figure 17:
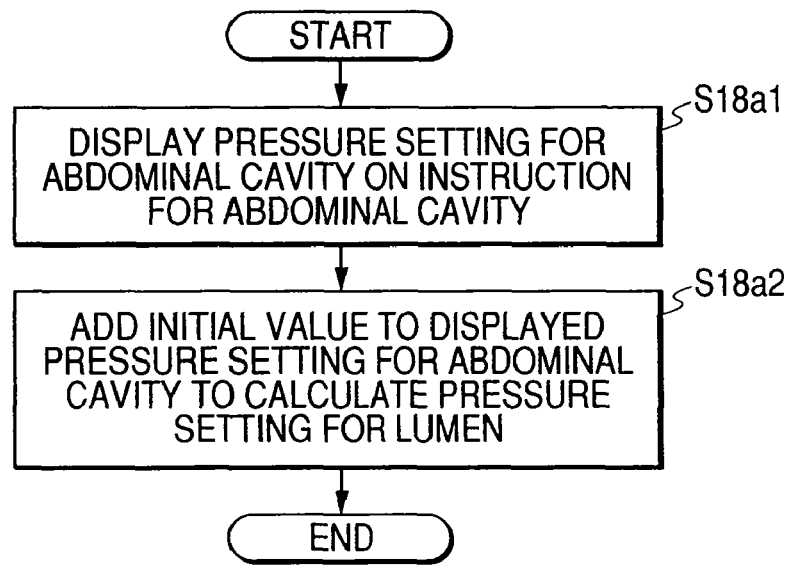
FIG. 17 is a flowchart schematically illustrating an example of control operations of a controller of the gas supply apparatus according to the fourth embodiment of the present invention.

When the instruction corresponding to the click of the pressure setting buttons 74a/74b is sent to the controller 98, the controller 98 receives the instruction and displays, on the pressure display 77b, a new pressure setting for the abdominal cavity AC based on the received instruction in cases where no initial value is displayed on the pressure display 77b. If an initial value is displayed on the pressure display 77b, the controller 98 updates the initial value displayed on the pressure display 77b to a new pressure setting for the abdominal cavity AC based on the received instruction (step S18a1 of FIG. 17).

Next, the operation unit 98a of the controller 98 adds the initial value of 5 mmHg to the displayed (updated) pressure setting for the abdominal cavity AC, thereby automatically calculating the pressure setting for the lumen BC (step S18a2).

Assuming that the pressure setting for the abdominal cavity AC, which is settable within the range from 3 to 25 mmHg, is set to 8 mmHg, the pressure setting for the lumen BC can be calculated by the following equation: 8 (mmHg)+5 (mmHg)=13 (mmHg).

As described in the first embodiment, the controller 98 controls a current pressure inside the lumen BC so that it reaches the pressure setting for the lumen BC calculated by the operation in step S18a2 while the gas supply apparatus 41M is in the lumen insufflation mode (see steps S1 and S7 to S12 in FIG. 6). These operations of the controller 98 allow an actual pressure inside the lumen BC to be constantly higher than an actual pressure inside the abdominal cavity AC by the initial value of 5 mmHg.

Note that, during laparoscopic surgery, when the pressure setting for the abdominal cavity AC is changed by the clicks of the pressure setting buttons 74a/74b by the operator, the controller 98 updates the pressure setting for the abdominal cavity AC displayed on the pressure display 77b to a new pressure setting based on the instruction corresponding to the clicks of the pressure setting buttons 74a/74b (see step S18a1).

Subsequently, the operation unit 98a of the controller 98 adds the initial value of 5 mmHg to the updated pressure setting for the abdominal cavity AC, thereby automatically changing the pressure setting for the lumen BC depending on the change of the pressure setting for the abdominal cavity AC (see step S18a2).

As a result, even if the pressure setting for the abdominal cavity AC is changed, it is possible to automatically change the pressure setting for the lumen BC depending on the change of the pressure setting for the abdominal cavity AC in accordance with the following equation: "the pressure setting for the lumen BC=the pressure setting for the abdominal cavity AC+the initial value (5 mmHg)".

As described above, in the fourth embodiment, it is possible to set the pressure setting for the lumen BC so as to keep the pressure setting for the lumen BC constantly higher than the pressure setting for the abdominal cavity AC based on the initial value. In other words, it is possible to set the pressure setting for the lumen BC to a value obtained by the sum of the pressure setting for the abdominal cavity AC and the initial value.

The operations of the controller 98 illustrated in FIG. 6 therefore make it possible to maintain an actual pressure inside the lumen BC to be higher than that inside the abdominal cavity AC.

As a result, when starting to insufflate the carbon dioxide gas into the lumen BC, the lumen BC can rapidly expand against an ambient pressure therearound, such as a pressure inside the abdominal cavity AC. This allows the operator to obtain a wide field in the lumen BC, such as the intestines of the patient 10, through the flexiblescope 31 immediately after the start of the insufflation of the lumen BC.

Particularly, in the fourth embodiment, even if the pressure setting for the abdominal cavity AC is changed, it is possible to automatically change the pressure setting for the lumen BC depending on the change of the pressure setting for the abdominal cavity AC in accordance with the following equation: "the pressure setting for the lumen BC=the pressure setting for the abdominal cavity AC+the initial value". Therefore, even if the pressure inside the abdominal cavity AC around the lumen BC is changed, the fourth embodiment allows the tension (expansion) of the lumen BC to remain unchanged.

Furthermore, in the fourth embodiment, the operator can set the pressure setting for the lumen BC without any operations through the manually operable setting section 63B; these operations are associated with the set of the pressure setting for the lumen BC. This makes it possible to reduce the burden on the operator, which is required to determine the pressure setting for the lumen BC, and to simplify the operator's operations required to set a pressure inside the lumen BC.

Fifth Embodiment

The configuration of a surgical system with a gas supply apparatus according to a fifth embodiment of the present invention is substantially identical to that of the surgical system 1 according to the first embodiment. Reference numerals assigned to elements of the surgical system according to the fifth embodiment, which are substantially identical to those of the surgical system 1, are the same as those assigned to the elements of the surgical system 1.

The fifth embodiment has characterized control operations of the controller 98 when the measured pressure inside the abdominal cavity AC or that inside the lumen BC falls down from a corresponding pressure setting.

Figure 18:
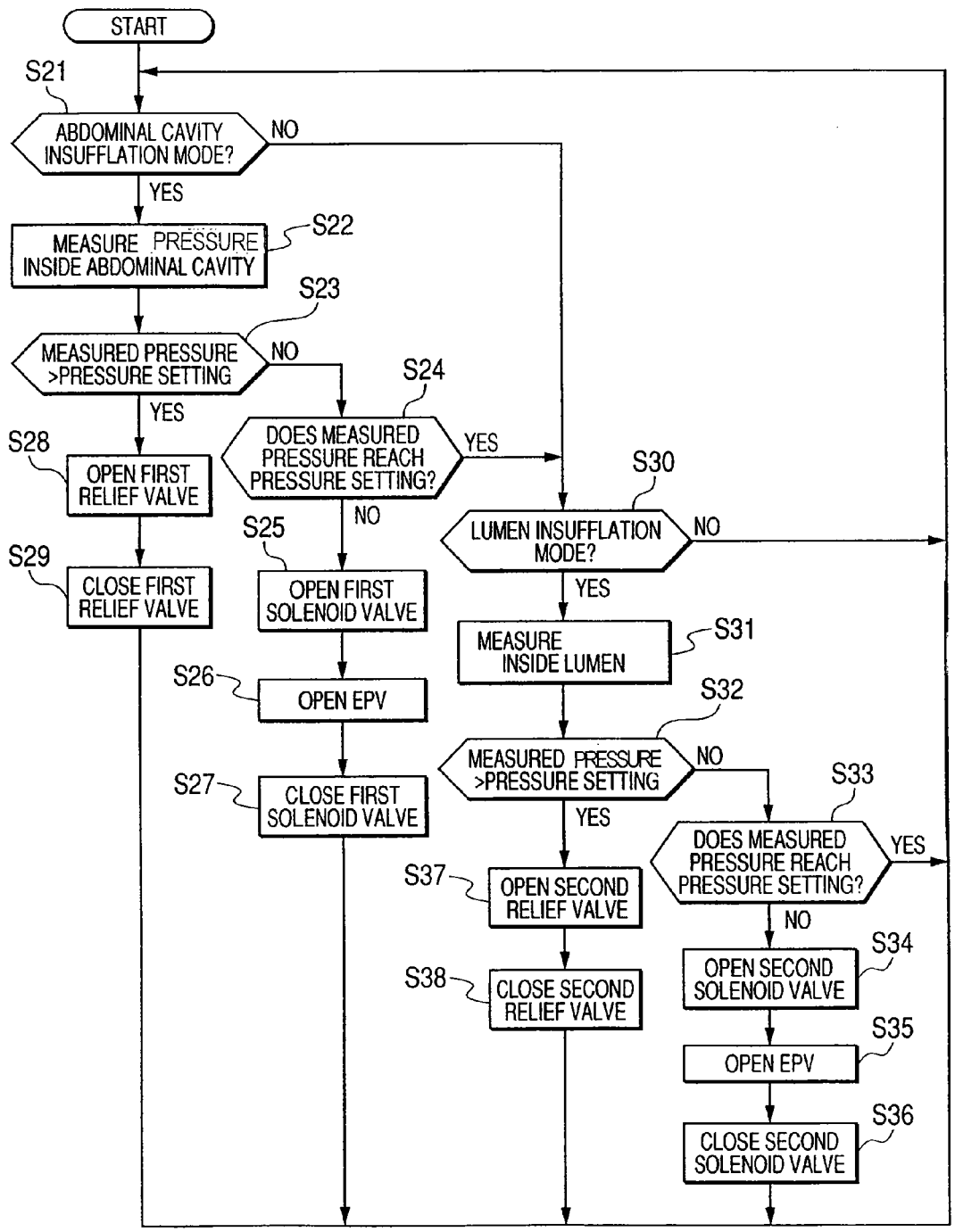
FIG. 18 is a flowchart schematically illustrating an example of control operations of a controller of a gas supply apparatus according to a fifth embodiment of the invention.

As shown in FIG. 18, the controller 98 determines whether the abdominal cavity select button 82 is turned on, in other words, its operation mode is the abdominal-cavity insufflation mode (FIG. 18; step S21).

When the abdominal cavity select button 82 is in on state, the controller 98 determines its operation mode is the abdominal-cavity insufflation mode, in other words, the determination in step S21 is YES so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open. As a result, the carbon dioxide gas supplied up to the inlet of the electropneumatic proportional valve 93 flows through the electropneumatic proportional valve 93 so that the pressure and the flow-rate of the carbon dioxide gas are regulated within the corresponding predetermined ranges suitable for the insufflation of the abdominal cavity AC, respectively. The carbon dioxide gas with the regulated pressure and flow-rate passes through the first solenoid valve 94A to be supplied into the abdominal cavity AC through the first adapter 41A, the first tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains the pressure inside the abdominal cavity AC based on the pressure measured by the first pressure sensor 95A with the first solenoid valve 94A closed, thereby displaying the obtained pressure value on the pressure display 77a in step S22.

The controller 98 determines whether the obtained pressure is higher than the pressure setting set on the front panel FP and displayed on the pressure display 77b (step S23).

When determining that the obtained pressure is lower than the pressure setting, that is, the determination in step S23 is NO, the controller 98 determines whether the obtained pressure reaches the pressure setting set on the front panel FP and displayed on the pressure display 77b or thereabout (step S24).

When determining that the obtained pressure does not reach the pressure setting, that is, the determination in step S24 is NO, the controller 98, as well as the first embodiment, calculates the difference between the obtained pressure and the pressure setting to determine a pressure reduction value of the electropneumatic proportional valve 93 based on the calculated difference.

Subsequently, the controller 98 sends the control signal to the first solenoid valve 94A to open it (step S25). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the abdominal cavity AC through the first $CO_2$ supply path DC1. Specifically, the carbon dioxide gas is supplied through the electropneumatic proportional valve 93, the third delivery channel C3, the first solenoid valve 94A, the fifth delivery channel C5, the first flow rate sensor 96A, the sixth delivery channel C6, and the first adapter 41A. Thereafter, the carbon dioxide gas is delivered through the first tube 45a and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S26.

After a predetermined period of time has elapsed, the controller 98 sends the control signal to the first solenoid valve 94A to close it, thereby interrupting the insufflation of the carbon dioxide gas into the abdominal cavity AC (step S27), returning to step S21. Thus, the controller 98 repeatedly executes the carbon dioxide gas supply and interruption control operations for the abdominal cavity AC shown in steps S1 to S6 until the pressure measured by the first pressure sensor 95A in step S22 reaches the pressure setting set on the front panel FP or thereabout.

In contrast, when it is determined that the obtained pressure is higher than the pressure setting, that is, the determination in step S23 is YES, the controller 98 sends the first relief valve 97A to open it and keep the valve 97A opened for a predetermined period of time in step S28.

The opening of the first relief valve 97A causes carbon dioxide gas in the abdominal cavity AC to be released, thereby reducing the pressure inside the abdominal cavity AC. After the predetermined period of time has elapsed, the controller 98 sends the control signal to the first relief valve 97A to close it in step S29, and repeatedly executes the operations in step S21 to S23, S28, and S29 until the pressure inside the abdominal cavity AC falls down to the pressure setting.

On the other hand, while the abdominal cavity select button 82 is in off state, in other words, the operation mode of the controller 98 is not in the abdominal-cavity insufflation mode (the determination in step S21 is NO), the controller 98 shifts to step S30. Similarly, when the abdominal cavity pressure reaches the pressure setting or thereabout, so that the determination in step S24 is YES, the controller 98 shifts to step S30.

In step S30, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S30 is YES so that the controller 98 enters the lumen insufflation mode.

In the lumen insufflation mode, while the switch portion 44a of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open. As a result, the carbon dioxide gas supplied up to the inlet of the electropneumatic proportional valve 93 flows therethrough so that the pressure and the flow-rate of the carbon dioxide gas are regulated within the corresponding predetermined ranges suitable for the insufflation of the lumen BC, respectively. The carbon dioxide gas with the regulated pressure and flow-rate passes through the second solenoid valve 94B to be supplied into the lumen BC through the second adapter 41B, the second tube 45b, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains the pressure inside the lumen BC based on the pressure measured by the second pressure sensor 95B with the second solenoid valve 94B closed, thereby displaying the obtained pressure value on the pressure display 80a in step S31.

The controller 98 determines whether the obtained pressure is higher than the pressure setting set on the front panel FP and displayed on the pressure display 80b (step S32).

When determining that the obtained pressure is lower than the pressure setting, that is, the determination in step S32 is NO, the controller 98 determines whether the obtained pressure reaches the pressure setting set on the front panel FP and displayed on the pressure display 80b or thereabout (step S33).

When determining that the obtained pressure does not reach the pressure setting, that is, the determination in step S33 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S34). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas is supplied through the electropneumatic proportional valve 93, the fourth delivery channel C4, the second solenoid valve 94B, the seventh delivery channel C7, the second flow rate sensor 96B, the eighth delivery channel C8, and the second adapter 41B. Thereafter, the carbon dioxide gas is delivered through the second tube 45b, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S35.

After a predetermined period of time has elapsed, the controller 98 sends the control signal to the second solenoid valve 94B to close it, thereby interrupting the insufflation of the carbon dioxide gas into the lumen BC (step S36), returning to step S21. Thus, the controller 98 repeatedly executes the carbon dioxide gas supply and interruption control operations for the lumen BC shown in steps S21, S30 to S36 until the pressure measured by the second pressure sensor 95B in step S31 reaches the pressure setting set on the front panel FP or thereabout.

In contrast, when it is determined that the obtained pressure is higher than the pressure setting, that is, the determination in step S32 is YES, the controller 98 sends the second relief valve 97B to open it and keep the valve 97B opened for a predetermined period of time in step S37.

The opening of the second relief valve 97B causes carbon dioxide gas in the lumen BC to be released, thereby reducing the intraluminal pressure of the lumen BC. After the predetermined period of time has elapsed, the controller 98 sends the control signal to the second relief valve 97B to close it in step S38, and repeatedly executes the operations in step S30 to S32, S37, and S38 until the pressure inside the lumen BC falls down to the pressure setting.

As described above, the gas supply apparatus 41 according to the fifth embodiment, in addition to obtaining the same effects as the first embodiment, provides the following effect. Specifically, in the fifth embodiment, the first relief valve 97A or the second relief valve 97B allows the pressure inside the abdominal cavity AC or that inside the lumen BC to decrease when it is higher than the corresponding one of the pressure settings.

This results in that, when the pressure inside the abdominal cavity AC or that inside the lumen BC is higher than the corresponding pressure setting, it is possible to regulate the pressure inside the abdominal cavity AC or that inside the lumen to the corresponding one of the pressure settings.

Figure 19:
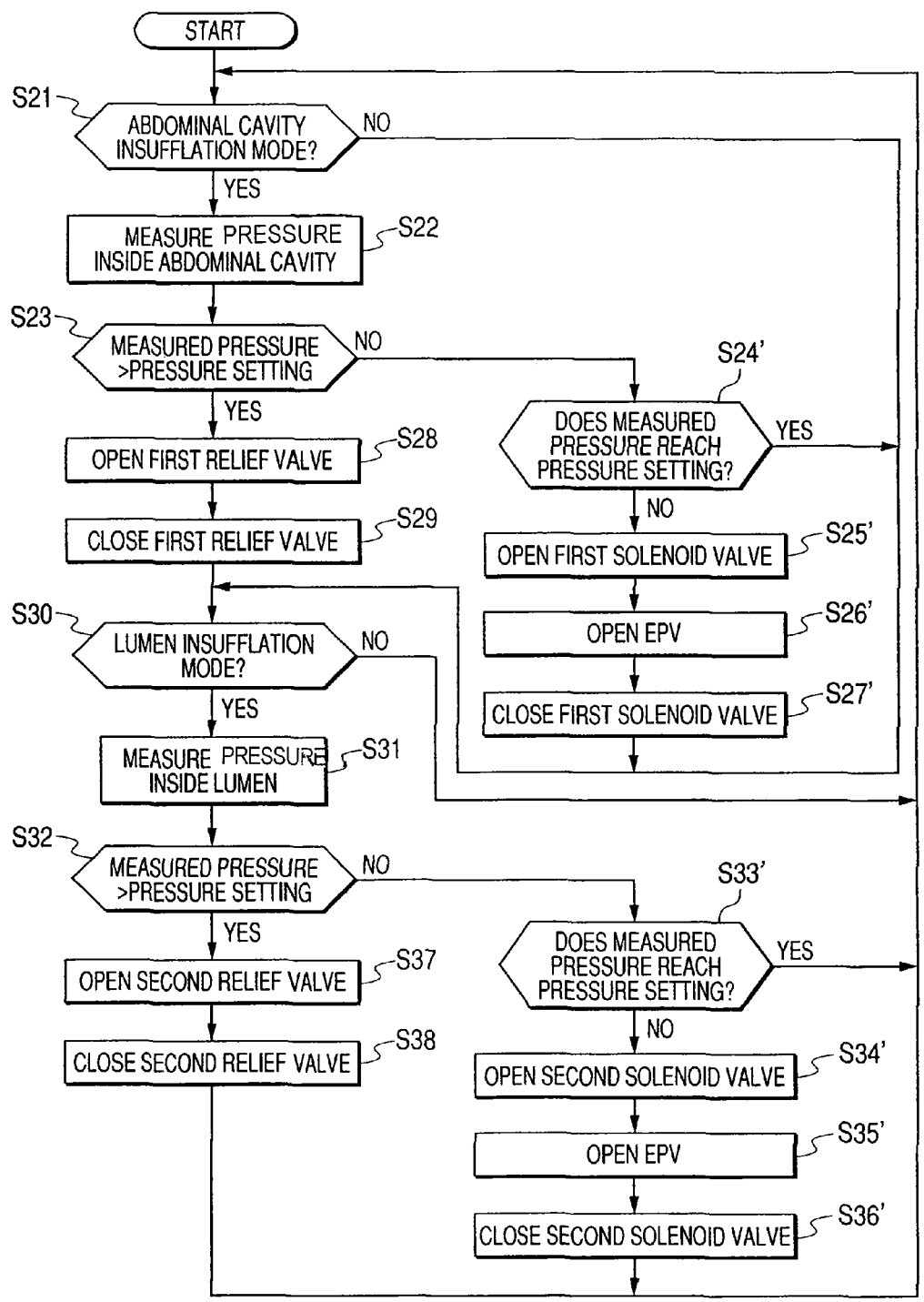
FIG. 19 is a flowchart schematically illustrating another example of control operations of the controller of the gas supply apparatus according to the fifth embodiment of the invention.

FIG. 19 represents another example of control operations of the controller 98 of the gas supply apparatus 41 according to the fifth embodiment.

Specifically, in the control operations shown in FIG. 18, when both the abdominal-cavity insufflation mode and the lumen insufflation mode are selected (both buttons 82 and 83 are on state), the controller 98 executes the operations in steps S25 to S27. The operations allow the carbon dioxide gas insufflation of the abdominal cavity AC until the pressure inside the abdominal cavity AC reaches the corresponding pressure setting. After that, the controller 98 executes the operations in steps S34 to S36 to insufflate the carbon dioxide gas into the lumen BC until the intraluminal pressure of the lumen BC reaches the corresponding pressure setting.

In contrast, in the control operations shown in FIG. 19, when both the abdominal-cavity and the lumen insufflation modes are selected, the controller 98 alternately executes the insufflation control operations in steps S25' to S27' and those in steps S34' to S36' until the pressures inside the abdominal cavity AC and the lumen BC reach the corresponding pressure settings, respectively.

Specifically, the controller 98 determines whether the obtained pressure in step S23 reaches the pressure setting or thereabout (FIG. 19; step S24'). When determining that the obtained pressure does not reach the pressure setting, that is, the determination in step S24' is NO, the controller 98, as well as the first embodiment, causes each of the first solenoid valve 94A and the electropneumatic proportional valve 93 to open, thereby supplying the carbon dioxide gas into the abdominal cavity AC.

After a predetermined period of time has elapsed, the controller 98 closes the first solenoid valve 94A in step S27'.

Subsequently, when the lumen select button 83 is in on state (determination in step S30 is YES), the controller 98 obtains the pressure inside the lumen BC based on the pressure measured by the second pressure sensor 95B with the second solenoid valve 94B closed in step S31.

Thus, the controller 98 determines whether the obtained pressure reaches the pressure setting set on the front panel FP and displayed on the pressure display 80b or thereabout (step S33'). When determining that the obtained pressure does not reach the pressure setting, that is, the determination in step S33' is NO, the controller 98 causes each of the second solenoid valve 94B and the electropneumatic proportional valve 93 to open, thereby supplying the carbon dioxide gas into the lumen BC The controller 98 repeatedly executes the control operations shown in steps S23, S24' to S27', S30 to S32, and S33' to S36' until the pressure inside abdominal cavity AC and that inside the lumen BC reach the corresponding pressure settings, respectively.

Incidentally, when the pressure inside the abdominal cavity AC or that inside the lumen BC is higher than the corresponding one of the pressure settings, the first relief valve 97A or the second relief valve 97B is opened to release the carbon dioxide gas in the abdominal cavity AC or that in the lumen BC. This allows the pressure inside the abdominal cavity AC or that inside the lumen BC to decrease, obtaining the same effects as those in the fifth embodiment.

Sixth Embodiment

The configuration of a surgical system with a gas supply apparatus according to a sixth embodiment of the present invention is substantially identical to that of the surgical system 1 according to the first embodiment. Reference numerals assigned to elements of the surgical system according to the sixth embodiment, which are substantially identical to those of the surgical system 1, are the same as those assigned to the elements of the surgical system 1.

The sixth embodiment has characterized control operations of the controller 98 to reduce the pressure inside the abdominal cavity AC temporarily when a rate of pressure rise inside the lumen BC decreases, thereby making the carbon dioxide gas easily flow into the lumen BC.

The control operations of the controller 98 according to the sixth embodiment will be described hereinafter with reference to FIGS. 20 and 21.

Figure 20:
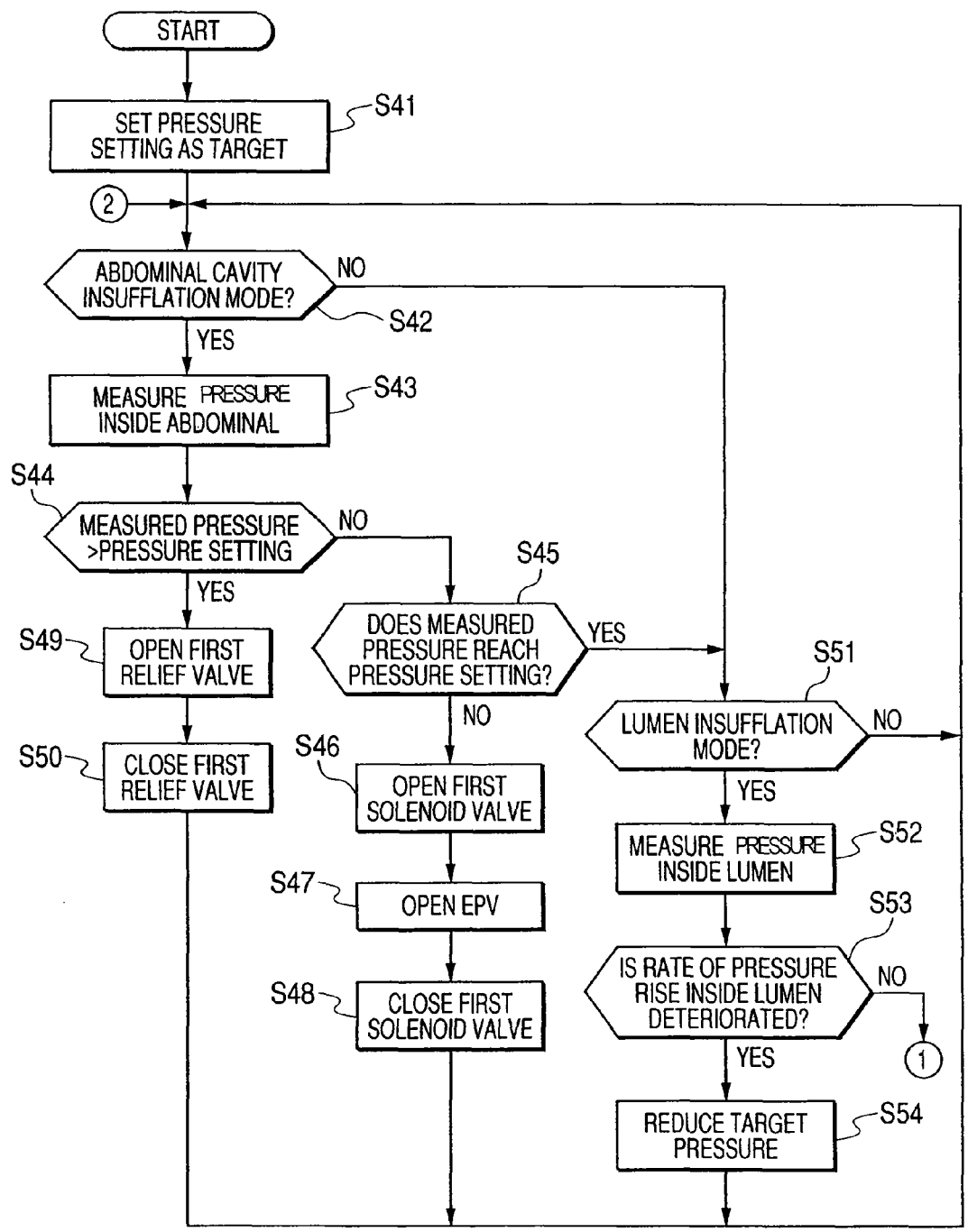
FIG. 20 is a flowchart schematically illustrating an example of control operations of a controller of a gas supply apparatus according to a sixth embodiment of the invention.
Figure 21:
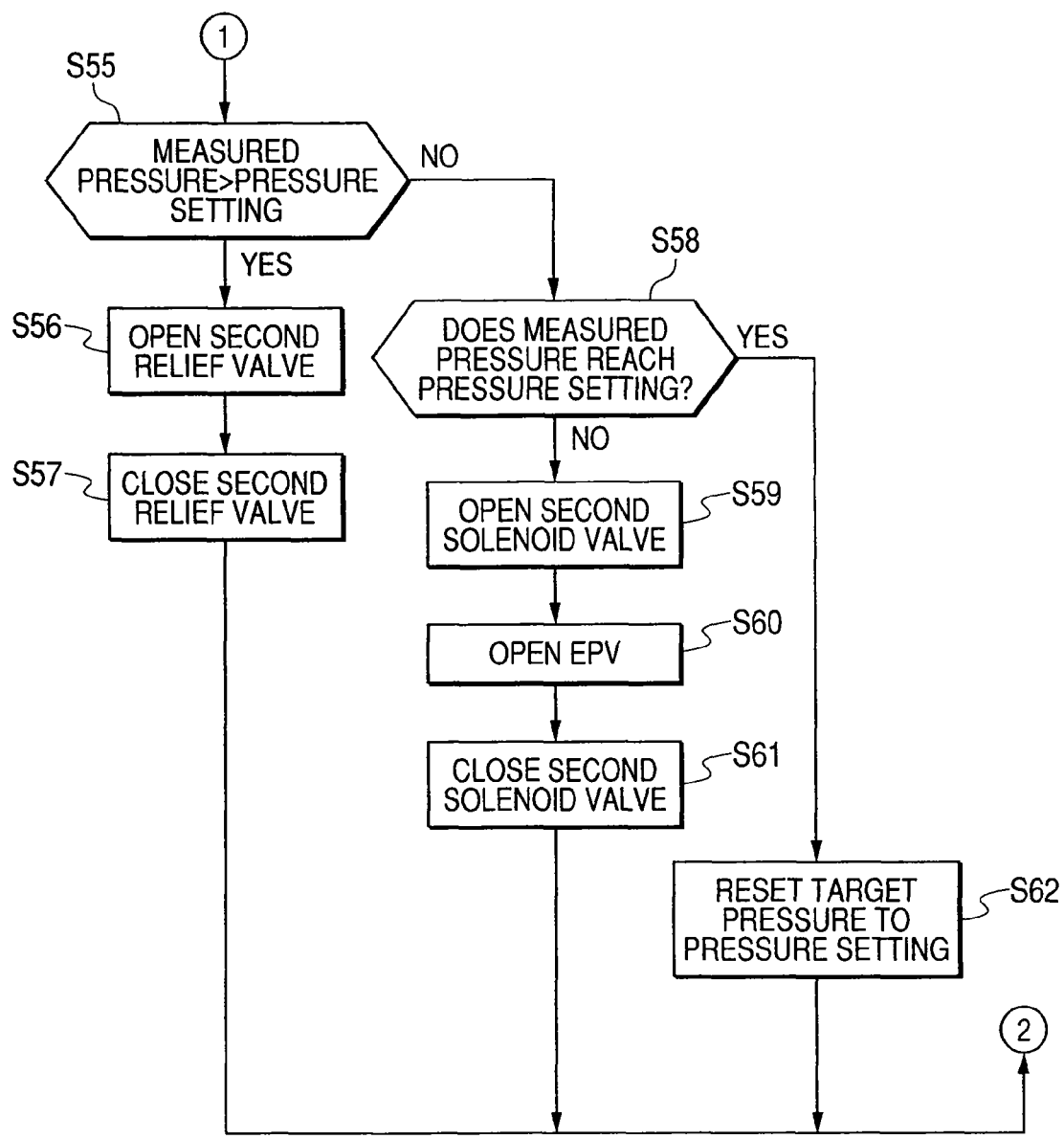
FIG. 21 is a flowchart schematically illustrating an example of control operations of the controller of the gas supply apparatus according to the third embodiment of the invention.

As shown in FIG. 20, the controller 98 establishes the pressure setting set on the front panel FP by an operator as a target pressure (FIG. 20; step S41). Next, the controller 98 determines whether the abdominal cavity select button 82 is turned on, in other words, its operation mode is the abdominal-cavity insufflation mode (step S42).

When the abdominal cavity select button 82 is in on state, the controller 98 determines its operation mode is the abdominal-cavity insufflation mode, in other words, the determination in step S42 is YES so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open.

As a result, the carbon dioxide gas supplied up to the inlet of the electropneumatic proportional valve 93 flows therethrough so that the pressure and the flow-rate of the carbon dioxide gas are regulated within the corresponding predetermined ranges suitable for the insufflation of the abdominal cavity AC, respectively. The carbon dioxide gas with the regulated pressure and flow-rate passes through the first solenoid valve 94A to be supplied into the abdominal cavity AC through the first adapter 41A, the first tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains the pressure inside the abdominal cavity AC based on the pressure measured by the first pressure sensor 95A with the first solenoid valve 94A closed, thereby displaying the obtained pressure on the pressure display 77a in step S43.

The controller 98 determines whether the obtained pressure is higher than the target pressure (step S44).

When determining that the obtained pressure is lower than the target pressure, that is, the determination in step S44 is NO, the controller 98 determines whether the obtained pressure value reaches the target pressure (step S45).

When determining that the obtained pressure does not reach the target pressure, that is, the determination in step S45 is NO, the controller 98, as well as the first embodiment, calculates the difference between the obtained pressure and the target pressure to determine a pressure reduction value of the electropneumatic proportional valve 93 based on the calculated difference.

Subsequently, the controller 98 sends the control signal to the first solenoid valve 94A to open it (step S46). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the abdominal cavity AC through the first $CO_2$ supply path DC1. Specifically, the carbon dioxide gas is supplied through the electropneumatic proportional valve 93, the third delivery channel C3, the first solenoid valve 94A, the fifth delivery channel C5, the first flow rate sensor 96A, the sixth delivery channel C6, and the first adapter 41A. Thereafter, the carbon dioxide gas is delivered through the first tube 45a and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S47.

After a predetermined period of time has elapsed, the controller 98 sends the control signal to the first solenoid valve 94A to close it, thereby interrupting the carbon dioxide gas insufflation of the abdominal cavity AC (step S48), returning to step S42. Thus, the controller 98 repeatedly executes the carbon dioxide gas supply and interruption control operations for the abdominal cavity AC shown in steps S42 to S48 until the pressure measured by the first pressure sensor 95A in step S43 reaches the target pressure.

In contrast, when it is determined that the obtained pressure is higher than the target pressure, that is, the determination in step S44 is YES, the controller 98 sends the first relief valve 97A to open it and keep the valve 97A opened for a predetermined period of time in step S49.

The opening of the first relief valve 97A causes carbon dioxide gas in the abdominal cavity AC to be released, thereby reducing the pressure inside the abdominal cavity AC. After the predetermined period of time has elapsed, the controller 98 sends the control signal to the first relief valve 97A to close it in step S50, and repeatedly executes the operations in step S42 to S44, S49, and S50 until the pressure inside the abdominal cavity AC falls down to the target pressure.

On the other hand, while the abdominal cavity select button 82 is in off state, in other words, the operation mode of the controller 98 is not in the abdominal-cavity insufflation mode (the determination in step S42 is NO), the controller 98 shifts to step S51. Similarly, when the abdominal cavity pressure reaches the pressure setting or thereabout, so that the determination in step S45 is YES, the controller 98 shift to step S51.

In step S51, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S51 is YES so that the controller 98 enters the lumen insufflation mode.

In the lumen insufflation mode, while the switch portion 44a of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open.

As a result, the carbon dioxide gas supplied up to the inlet of the electropneumatic proportional valve 93 flows therethrough so that the pressure and the flow-rate of the carbon dioxide gas are regulated within the corresponding predetermined ranges suitable for the insufflation of the lumen BC, respectively. The carbon dioxide gas with the regulated pressure and flow-rate passes through the second solenoid valve 94B to be supplied into the lumen BC through the second adapter 41B, the lumen tube 45b, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains the pressure inside the lumen BC based on the pressure measured by the second pressure sensor 95B with the second solenoid valve 94B closed, thereby displaying the obtained pressure on the pressure display 80a in step S52.

The controller 98 determines whether a rate of rise of the obtained pressure deteriorates in step S53. In other words, the rate of rise of the pressure inside the lumen BC is lower than a predetermined threshold rate in step S53.

As an example of the operation in step S53, the controller 98 calculates a rate of rise of the pressure inside the lumen BC for a predetermined period of time, which is represented as dP/dt. Where "P" indicates the pressure inside the lumen BC, and "t" indicates the predetermined period of time. Subsequently, the controller 98 compares the rate of rise "dP/dt" with the predetermined threshold rate to determine whether the rate of rise of the pressure inside the lumen BC deteriorates based on the compared result.

When it is determined that the rate of rise of the pressure inside the lumen BC deteriorates, for example, the rate of rise "dP/dt" is lower than the predetermined threshold rate, the determination in step S53 is YES. Thus, the controller 98 decreases the target pressure established by the operation in step S41 by a predetermined value (step S52), returning to step S42. Specifically, the controller 98 repeatedly executes the operations in steps S42 to S44, S49, and S50 until the pressure inside the lumen BC reaches the target pressure, which has been changed in step S54.

In contrast, when it is determined that the rate of rise of the pressure inside the lumen BC is kept sufficiently high so that it dose not deteriorate, for example, the rate of rise "dP/dt" is as high as or higher than the predetermined threshold rate, the determination in step S53 is NO. Hence, the controller 98 determines whether the obtained pressure is higher than the pressure setting set on the front panel FP and displayed on the pressure display 80b (FIG. 21; step S55).

When it is determined that the obtained pressure is higher than the pressure setting, that is, the determination in step S55 is YES, the controller 98 sends the second relief valve 97B to open it and keep the valve 97B opened for a predetermined period of time in step S56.

The opening of the second relief valve 97B causes carbon dioxide gas in the lumen BC to be released, thereby reducing the pressure inside the lumen BC. After the predetermined period of time has elapsed, the controller 98 sends the control signal to the second relief valve 97B to close it in step S57, and repeatedly executes the operations in step S51 to S57 until the pressure inside the lumen BC falls down to the pressure setting.

In contrast, when determining that the obtained pressure is lower than the pressure setting, that is, the determination in step S55 is NO, the controller 98 determines whether the obtained pressure value reaches the pressure setting set on the front panel FP and displayed on the pressure display 80b or thereabout (step S58).

When determining that the obtained pressure does not reach the pressure setting, that is, the determination in step S58 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S59). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas is supplied through the electropneumatic proportional valve 93, the fourth delivery channel C4, the second solenoid valve 94B, the seventh delivery channel C7, the second flow rate sensor 96B, the eighth delivery channel C8, and the second adapter 41B. Thereafter, the carbon dioxide gas is delivered through the second tube 45b, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S60.

After a predetermined period of time has elapsed, the controller 98 sends the control signal to the second solenoid valve 94B to close it, thereby interrupting the insufflation of the carbon dioxide gas into the lumen BC (step S61), returning to step S51. Thus, the controller 98 repeatedly executes the carbon dioxide gas supply and interruption control operations for the lumen BC shown in steps S51 to S53, S55, and S58 to S61 until the pressure measured by the second pressure sensor 95B in step S42 reaches the pressure setting set on the front panel FP or thereabout.

On the other hand, in step S58, when it is determined that the obtained pressure reaches the pressure setting, that is, the determination in step S58 is YES. In this case, when reducing the target pressure from the pressure setting established on the front panel FP and displayed on the pressure display 77b in step S54, the controller 98 resets the target pressure to the pressure setting (step S62), repeatedly executing the operations in steps S42 to S61.

Figure 22:
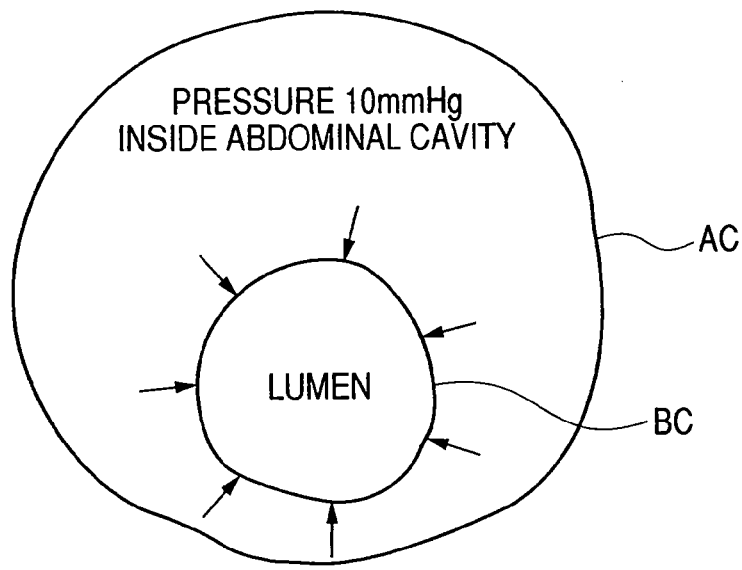
FIG. 22 is a view schematically illustrating a lumen affected by a pressure of an abdominal cavity of 10 mmHg.

In the sixth embodiment, in a case where the pressure setting for the abdominal cavity AC set on the front panel FP is 10 mmHg, and the pressure inside the abdominal cavity AC is coincide with the pressure setting of 10 mmHg (see FIG. 22). In this case, because the lumen BC is located at a position affected by the pressure inside the abdominal cavity AC, for example, at a position within the abdominal cavity AC, the pressure inside the abdominal cavity AC exerts an influence upon the lumen BC, which prevents the carbon dioxide gas from flowing into the lumen BC.

Figure 23:
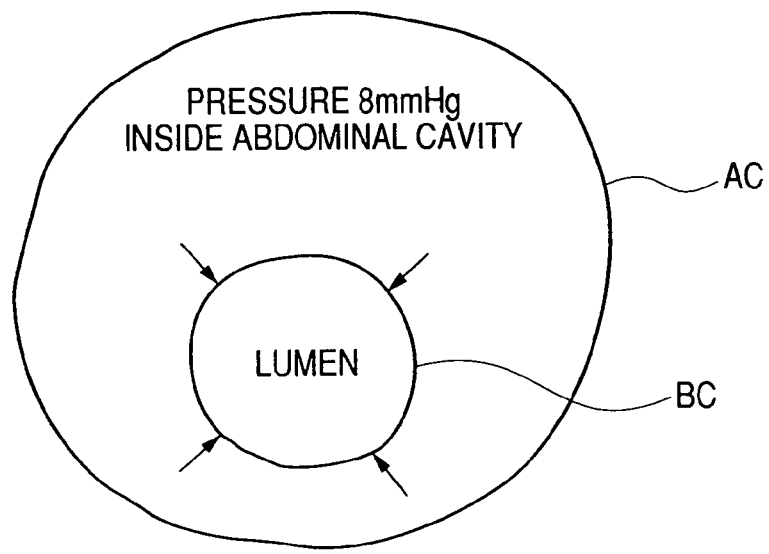
FIG. 23 is a view schematically illustrating the lumen affected by the pressure of the abdominal cavity of 8 mmHg.

On this point, in the present invention, when it is difficult for the carbon dioxide gas to flow into the lumen BC, the target pressure is reduced from 10 mmHg to 8 mmHg (see FIG. 23), and the operations in steps S51 to S53 and steps S55 to S61 are executed by the controller 98. This results in that the pressure inside the abdominal cavity AC is reduced, which lessens the influence of pressure inside the abdominal cavity on the lumen BC, thereby making the carbon dioxide gas easily flow into the lumen BC.

As set forth above, in the gas supply apparatus 41 according to the sixth embodiment, when the rate of pressure rise inside the lumen BC, it is possible to temporarily reduce the pressure inside the abdominal cavity AC. This allows the lumen BC to smoothly distend with the influence of the abdominal cavity's pressure lessened, making it possible to improve the operating efficiency of the laparoscopic surgery system 1.

Seventh Embodiment

The configuration of a gas supply apparatus 41N according to a seventh embodiment of the present invention is substantially identical to that of the gas supply apparatus 41 according to the first embodiment. Reference numerals assigned to elements of the gas supply apparatus according to the seventh embodiment, which are substantially identical to those of the surgical system 1, are the same as those assigned to the elements of the gas supply apparatus 41.

Figure 24:
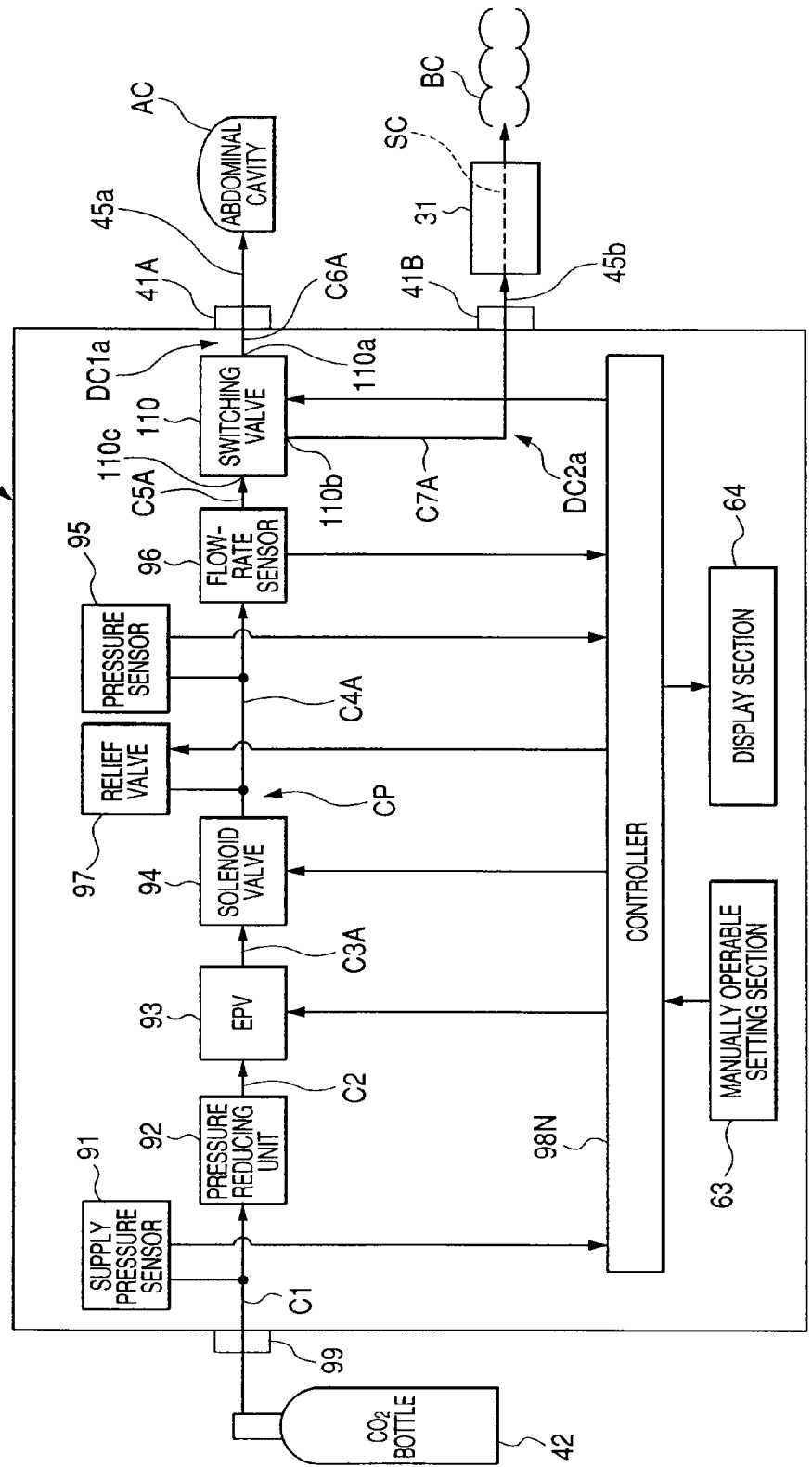
FIG. 24 is a block diagram illustrating a schematic structure of a gas supply apparatus according to a seventh embodiment of the present invention.

As shown in FIG. 24, the gas supply apparatus 41N of the seventh embodiment is provided with the high pressure adapter 99, the first delivery channel C1, the supply pressure sensor 91, and the pressure reducing unit 92 serving as, for example, a pressure regulator. The gas supply apparatus 41N includes the second delivery channel C2, the electropneumatic proportional valve (EPV) 93 as an example of pressure regulating valves, serving as the pressure regulator, a third delivery channel C3A, and a fourth delivery channel C4A.

In addition, the gas supply apparatus 41N includes an electromagnetic valve (solenoid valve) 94 as an example of open/close valves. The electromagnetic valve 94 serves as the pressure regulator.

The gas supply apparatus 41N includes a fifth delivery channel C5A, a sixth delivery channel C6A, a pressure sensor 95, a flow-rate sensor 96. Moreover, the gas supply apparatus 41N includes a seventh delivery channel C7A, a relief valve 97, a controller 98N, the manually operable setting section 63, the display section 64, and the first and second adapters 41A and 41B.

As shown in FIG. 24, because the gas supply apparatus 41N of the fourth embodiment whose elements located at the upstream of the electropneumatic proportional valve 93 are substantially identical to those of the gas supply apparatus 41 of the first embodiment, so that the descriptions of which are omitted or simplified.

As shown in FIG. 24, the gas supply apparatus 41N of the seventh embodiment is provided with a common $CO_2$ supply path CP for both the abdominal cavity AC and the lumen BC, which is coupled to the outlet of the electropneumatic proportional valve 93. The common $CO_2$ supply path CP is composed of the third delivery channel C3A, the solenoid valve 94, the fourth delivery channel C4A, the flow-rate sensor 96, and the fifth delivery channel C5A.

The solenoid valve 94 is connected to the outlet of the electropneumatic proportional valve 93 through the third delivery channel C3A. The outlet of the solenoid valve 94 is connected to the inlet of the flow-rate sensor 96 through the fourth delivery channel C4A. The pressure sensor 95 is attached to the fourth delivery channel C4A. The relief valve 97 is attached to the fourth delivery channel C4A at the upstream of the pressure sensor 95. The flow-rate sensor 96 is configured to detect a flow-rate of the carbon dioxide gas passing through the fourth delivery channel C4A.

The outlet of the flow-rate sensor 96 is connected to one end of the fifth delivery channel C5A.

In addition, the gas supply apparatus 41N is provided with a switching valve 110 whose inlet port 110c is connected to the other end of the fifth delivery channel C5A.

The switching valve 110 has two outlet ports 110a and 110b. The outlet ports 110a and 110b of the switching valve 110 are separated for the abdominal cavity AC and the lumen BC, respectively. The abdominal cavity outlet port 110a is connected to the first adapter 41A through the sixth delivery channel C6A; the lumen outlet port 110b is connected to the second adapter 41B through the seventh delivery channel C7A.

In the seventh embodiment, a first $CO_2$ supply path DC1a directing to the abdominal cavity AC includes the electropneumatic proportional valve 93, and the common $CO_2$ supply path CP constituting the third delivery channel C3A, the solenoid valve 94, the flow-rate sensor 96, and the fifth delivery channel C5A. In addition, the first $CO_2$ supply path DC1a includes the switching valve 110, the sixth delivery channel C6A, the first adapter 41A, and the first tube 45a. The configuration of the first $CO_2$ supply path DC1a allows the carbon dioxide gas to be introduced into the abdominal cavity AC therethrough.

In addition, in the seventh embodiment, a second $CO_2$ supply path DC2a directing to the lumen BC includes the electropneumatic proportional valve 93, and the common $CO_2$ supply path CP constituting the third delivery channel C3A, the solenoid valve 94, the flow-rate sensor 96, and the fifth delivery channel C5A. In addition, the second $CO_2$ supply path DC2a includes the switching valve 110, the seventh delivery channel C7A, the second adapter 41B, and the second tube 45b.

The electropneumatic proportional valve 93, the solenoid valve 94, the relief valve 97, the pressure sensor 95, the flow-rate sensor 96, and the switching valve 110 are electrically connected to the controller 98N.

The electropneumatic proportional valve 93, as well as the first embodiment, is designed to change its opening in proportional to a voltage or a current as the control signal applied from the controller 98N so as to regulate the pressure and the flow-rate of the carbon dioxide gas flowing therethrough within the corresponding appropriate ranges, respectively. Just like the first embodiment, the solenoid valve 94 is operative to open and close based on the control signal sent from the controller 98N.

The pressure sensor 95 has a function of measuring a pressure inside the abdominal cavity AC and that inside the lumen BC, thereby sending the measured result to the controller 98N. The flow-rate sensor 96 has a function of measuring a flow-rate of the carbon dioxide gas flowing through the fourth delivery channel C4A toward the switching valve 110, thereby sending the measured result to the controller 98N.

The switching valve 110 has a function of selectively outputting the carbon dioxide gas supplied through the inlet port 110c to either the outlet port 110a or the outlet port 110b based on a control signal sent from the controller 98N.

The relief valve 97 is operative to remain in a closed state, and to open based on a control signal sent from the controller 98N.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46 and the like to be reduced in pressure by the pressure reducing unit 92. Thereafter, the carbon dioxide gas is delivered to the electropneumatic proportional valve 93 so that the pressure and flow-rate is regulated based on the control signals sent from the controller 98.

The carbon dioxide gas with the regulated pressure and flow-rate is delivered through the common $CO_2$ supply path CP (solenoid valve 94, the fourth delivery channel C4A, flow-rate sensor 96, and the fifth delivery channel C5A) to the switching valve 110.

The carbon dioxide gas delivered to the switching valve 110 is switched to output either the sixth delivery channel C6A or the seventh delivery channel C7A through the outlet port 110a or outlet port 110b.

Incidentally, in the seventh embodiment, a first delivery member of the present invention corresponds to, for example, at least the sixth channel C6A in the first $CO_2$ supply path DC1a, and a second delivery member thereof corresponds to, for example, at least the seventh delivery channel C7A in the second $CO_2$ supply path DC2a.

Next, operations of the gas supply apparatus 41N will be described hereinafter.

Figure 25:
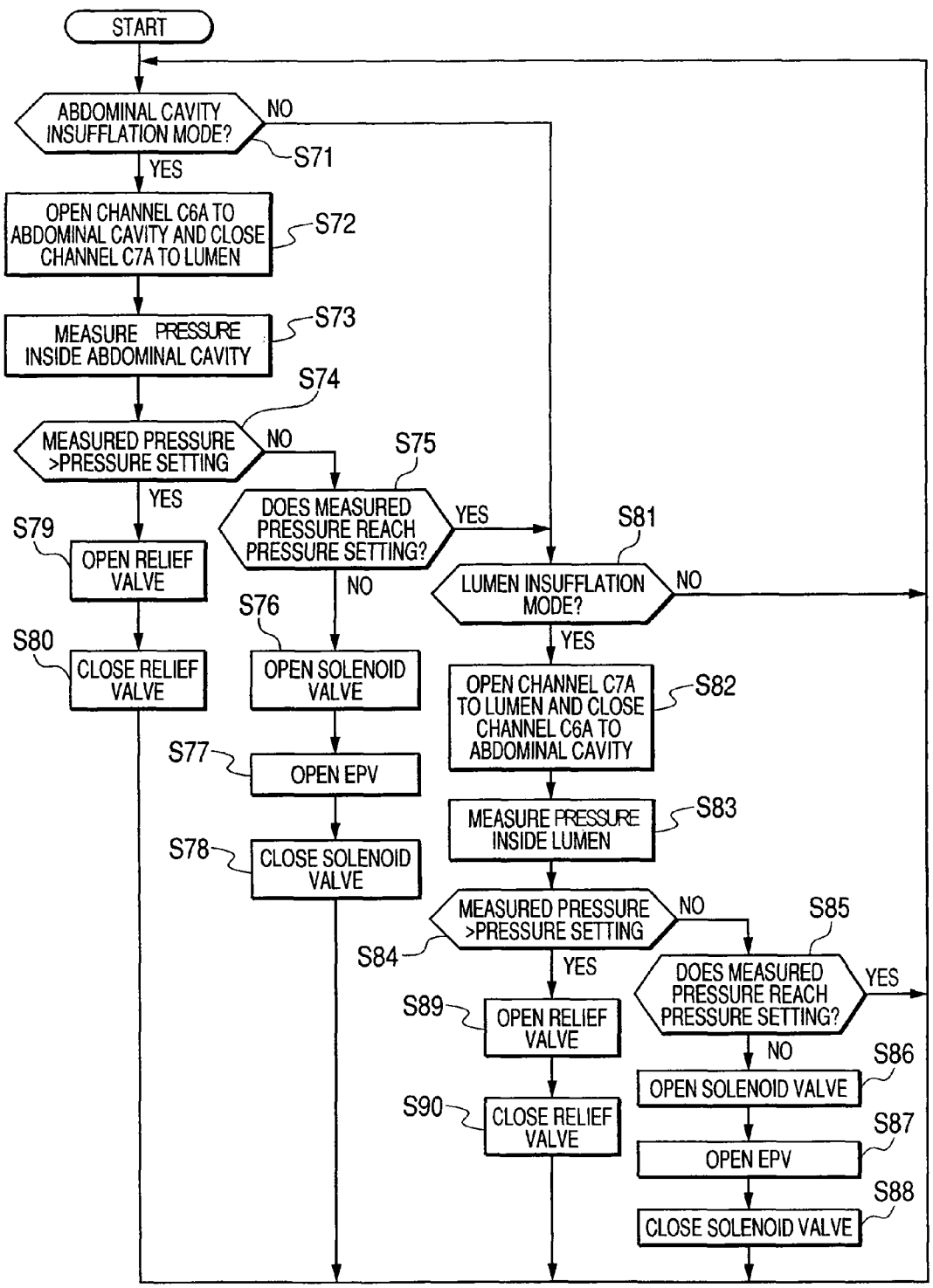
FIG. 25 is a flowchart schematically illustrating an example of control operations of a controller illustrated in FIG. 24 according to the seventh embodiment of the invention.

As shown in FIG. 25, the controller 98N determines whether the abdominal cavity select button 82 is turned on, in other words, its operation mode is the abdominal-cavity insufflation mode (FIG. 25; step S71).

When the abdominal cavity select button 82 is in on state, the controller 98N determines its operation mode is the abdominal-cavity insufflation mode, in other words, the determination in step S71 is YES so that the controller 98N enters the abdominal-cavity insufflation mode.

In the abdominal-cavity insufflation mode, while the gas-supply start button 73 is in on state, the controller 98N sends the control signal to the switching valve 110 so that the switching valve 110 switches its output to the output port 110a. Specifically, the switching valve 110 opens the sixth delivery channel C6A constituting the first $CO_2$ supply path DC1a directing to the abdominal cavity AC and closes the seventh delivery channel C7A constituting the second $CO_2$ supply path DC2a directing to the lumen BC in step S72.

That is, the switching operation of the switching valve 110 allows the carbon dioxide gas insufflation of the abdominal cavity AC and relief therefrom.

In the abdominal-cavity insufflation mode, while the gas-supply start button 73 is in on state, the controller 98N repeatedly executes control operations shown in steps S73 to S80, which correspond to the operations shown in steps S22 to S29, respectively. These repeated operations allow the pressure inside the abdominal cavity AC to be regulated to the corresponding pressure setting established on the front panel FP.

On the other hand, while the abdominal cavity select button 82 is in off state, in other words, the operation mode of the controller 98 is not in the abdominal-cavity insufflation mode (the determination in step S71 is NO), the controller 98N shifts to step S81. Similarly, when the abdominal cavity pressure reaches the pressure setting or thereabout, so that the determination in step S75 is YES, the controller 98N shifts to step S81.

In step S81, the controller 98N determines whether the lumen select button 83 is turned on, in other words, its operation mode is the lumen insufflation mode.

When the lumen select button 83 is in on state, the controller 98N determines its operation mode is the lumen insufflation mode, in other words, the determination in step S81 is YES so that the controller 98N enters the lumen insufflation mode.

In the lumen insufflation mode, while the switch portion 44a of the foot switch 44 is in on state, the controller 98N sends the control signal to the switching valve 110 so that the switching valve 110 switches its output to the output port 110b. Specifically, the switching valve 110 opens the seventh delivery channel C7A constituting the second $CO_2$ supply path DC2a directing to the lumen BC and closes the sixth delivery channel C6A constituting the first $CO_2$ supply path DC1a directing to the abdominal cavity AC in step S82.

That is, the switching operation of the switching valve 110 allows carbon dioxide gas insufflation of the lumen BC and relief therefrom.

In the lumen insufflation mode, while the switch portion 44a of the foot switch 44 is in on state, the controller 98N repeatedly executes control operations shown in steps S81 to S90, which correspond to the operations shown in steps S30 to S38, respectively. These repeated operations allow the pressure inside the lumen BC to be regulated to the pressure setting established on the front panel FP.

As described above, in the gas supply apparatus 41N according to the seventh embodiment, providing the switching valve 110 to the upstream of the first and second adapters 41A and 41B allows commonality of the upstream $CO_2$ supply path of the switching valve 110 between the abdominal cavity AC and the lumen BC, as the common $CO_2$ supply path CP. The structure, in addition to the same effects as the first and sixth embodiments, makes it possible to reduce the number of elements of the gas supply apparatus 41N as compared with those of, for example, the gas supply apparatus 41M according to the sixth embodiment. For example, in the gas supply apparatus 41N according to the seventh embodiment, the number of relief valves, the number of pressure sensors, the number of flow-rate sensors, and the number of delivery channels can be reduced as compared with the gas supply apparatus 41M according to the sixth embodiment. As a result, it is possible to offer simplified manufacturing of the gas supply apparatus 41N and to reduce the manufacturing cost thereof.

Eighth Embodiment

Figure 26:
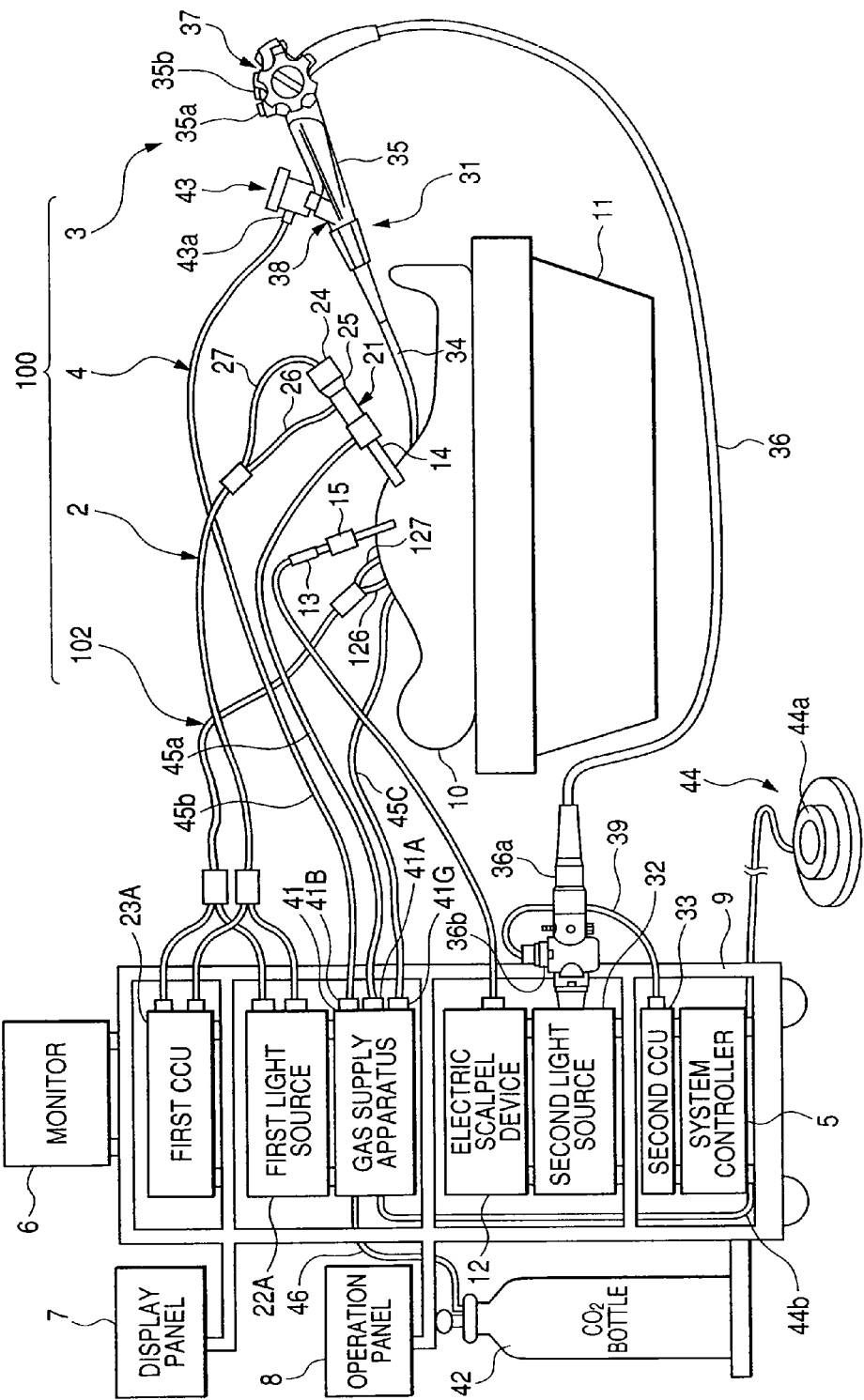
FIG. 26 is an overall structural view schematically illustrating the structure of an endoscopic surgical system equipped with a gas supply apparatus according to an eighth embodiment of the present invention.

The configuration of a surgical system 100 with a gas supply apparatus 141 according to an eighth embodiment of the present invention is illustrated in FIG. 26. Note that elements of the surgical system 100 according to the eighth embodiment, which are substantially identical to those of the surgical system 1 according to the first embodiment shown in FIG. 1, are represented by the same reference characters as in FIG. 1. The descriptions of the elements of the surgical system 100 according to the eighth embodiment are therefore omitted or simplified.

The surgical system 100 according to the eighth embodiment of the present invention allows an operator to carry out surgical operations of at least one site to be treated of a patient 10 while the operator monitors at least one of a first abdominal cavity AC1, a second abdominal cavity AC2 thereof, and a lumen BC of the patient 10. The second abdominal cavity AC2 is different from the first abdominal cavity AC1.

Figure 31:
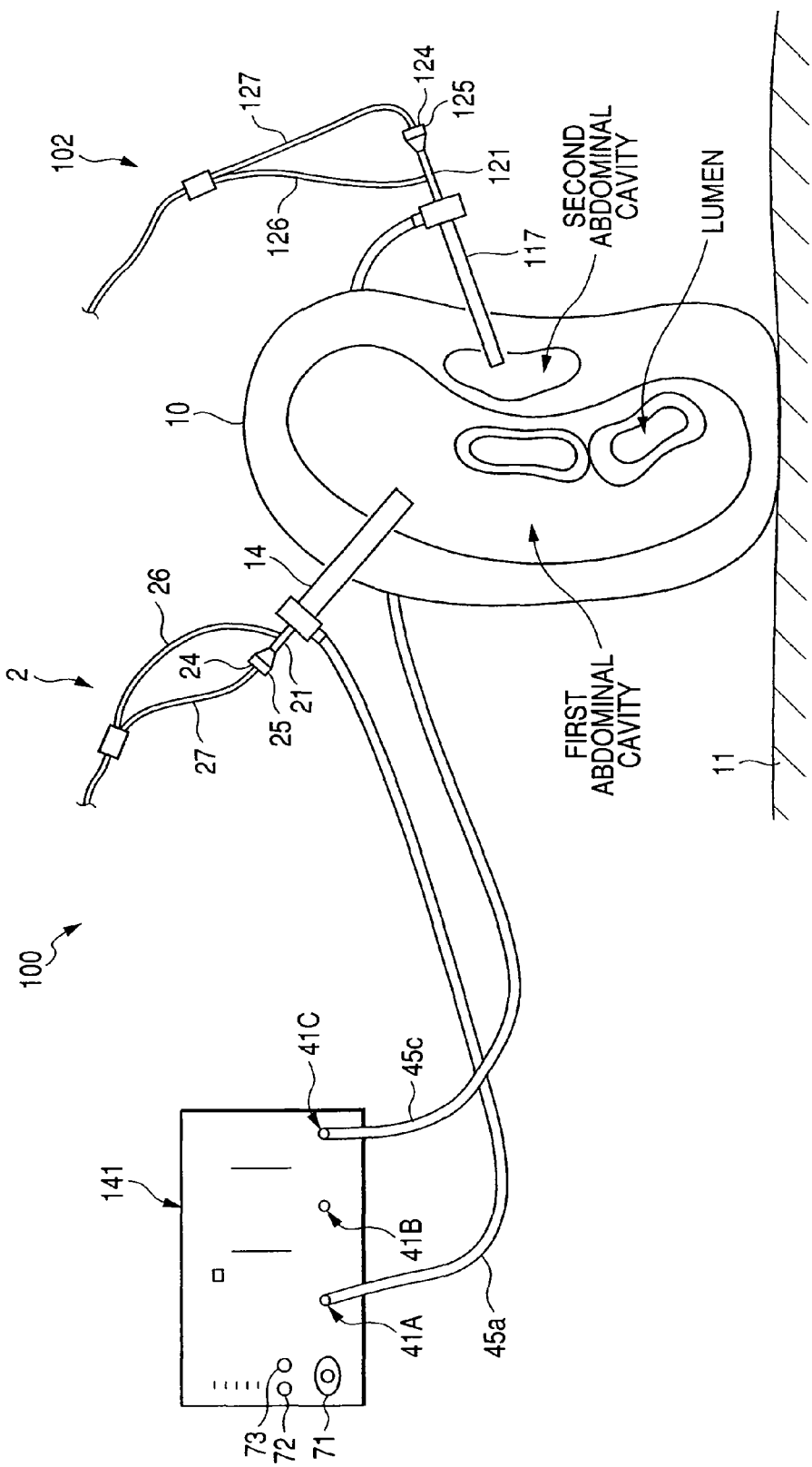
FIG. 31 is a view schematically illustrating service conditions of the gas supply apparatus according to the eighth embodiment when insufflating a carbon dioxide gas into a first abdominal cavity and a second abdominal cavity of a patient.

Specifically, as illustrated in FIGS. 26 and 31, the surgical system 100 includes a third endoscope system 102 for insufflation of the second abdominal cavity AC2 in addition to the first endoscope system 2 for insufflation of the first abdominal cavity AC1 and the second endoscope system 3 for insufflation of the lumen BC. Note that, in the eighth embodiment, the first tube 45a of the first endoscope system 2 is coupled to one end of the first trocar 14. The carbon dioxide gas guided through the first tube 45a passes through the first trocar 14 to be delivered from the other end thereof.

The gas supply system 4 according to the eighth embodiment includes a third tube 45c for insufflation of the second abdominal cavity AC2 in addition to the first and second tubes 45a and 45b.

In addition to the first and second adapters 41A and 41B, the gas supply apparatus 141 is provided with a third adapter 41G for insufflation of the second abdominal cavity AC2. The third adapter 41G is airtightly coupled to one end of the third tube 45c. As illustrated in FIG. 31, the other end of the third tube 45c is airtightly coupled to a fourth trocar 117 inserted into the second abdominal cavity AC2, such as a retroperitoneal cavity, of the patient 10.

In addition, the third endoscope system 102 is provided with a rigid endoscope (rigidscope) 121 with substantially the same structure as the rigidscope 21 of the first endoscope system 2. One end portion of the rigidscope 121 is configured to be inserted in part into the fourth trocar 117. The rigidscope 121 includes a camera (TV camera) 124 for endoscopes.

The rigidscope 121 is provided with an illumination optics (not shown) and an observation optics (not shown), which are installed in the one end portion thereof. The illumination optics is composed of, for example, a light guide and the like, and configured to illuminate light onto a third target, such as the site to be treated, of the inside of the patient 10. For example, the observation optics is composed of relay lenses and the like. The observation optics is configured to optically deliver an optical image of the third target illuminated by the light.

The rigidscope 121 is provided at its other end portion with an eyepiece 125 that allows the operator to observe the optical image delivered by the observation optics. The camera 124 is detachably installed in the eyepiece 125. The camera 124 is integrated with an image pickup device, such as a CCD or the like, having a light sensitive pixel area, wherein the optical image delivered by the observation optics is focused on the light sensitive pixel area thereof. The optical image of the third target focused on the light sensitive pixel area of the image pickup device is photoelectrically converted into an electric signal as a third image signal, by the image pickup device.

The third endoscope system 102 is provided with a light guide cable 126 extending from one side of the other end portion of the rigidscope 121. The light guide cable 126 is optically coupled to a first light source 22A. The third endoscope system 102 is provided with an image pickup cable 127 electrically connecting between a first CCU 23A and the camera 124.

The first light source 22A has a function of supplying illumination light to the illumination optics of the rigidscope 121 of the third endoscope system 102 via the light guide cable 126 in addition to the function of supplying illumination light to the illumination optics of the rigidscope 21 of the first endoscope system 2.

The first CCU 23A has:

a first function of controlling the image pick-up processes of the image pickup device of the camera 24 of the first endoscope system 2; a second function of, when the first image signal corresponding to the optical image of a first target, which is picked up by the image pickup device of the camera 24, is sent to the first CCU 23A, receiving the first image signal to subject the received first image signal to image processing of necessity;

a third function of outputting the image-processed first image signal to at least one of the monitor 6 and the center display panel 7;

a fourth function of controlling the image pick-up processes of the camera's image pickup device of the third endoscope system 102;

a fifth function of, when the third image signal corresponding to the optical image of the third target, which is picked up by the image pickup device of the camera 124, is sent to the first CCU 23A, receiving the third image signal to subject the received third image signal to image processing of necessity; and a sixth function of outputting the image-processed third image signal to at least one of the monitor 6 and the center display panel 7.

Theses functions of the first CCU 23A allow at least one of the monitor 6 and the center display panel 7 to display both a first image (endoscopic image) of the first target thereon based on the first image signal and a third image (endoscopic image) of the third target thereon based on the third image signal. Note that, as described hereinbefore, the second endoscope system 3 allows at least one of the monitor 6 and the center display panel 7 to display a second image (endoscopic image) of a second target thereon based on the second image signal in addition to the first and second images.

In addition, the gas supply apparatus 141 includes a front panel FP10 attached along, for example, one side of a housing of the gas supply apparatus 141. The gas supply apparatus 141 also includes a manually operable setting section 163 and a display section 164, which are provided on the front panel FP10.

Figure 27:
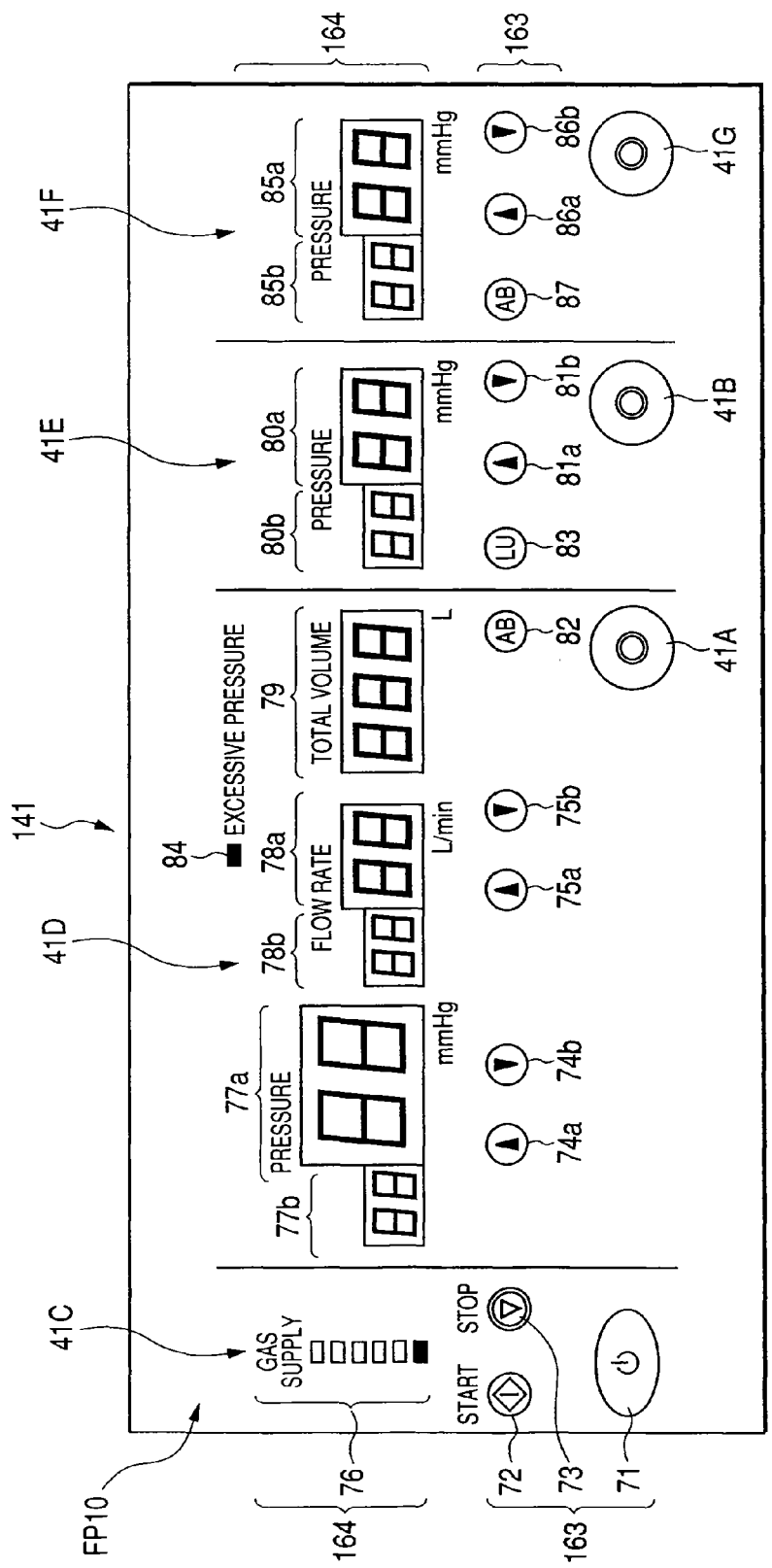
FIG. 27 is a view schematically illustrating a configuration example of a manually operable setting section and a display section provided on a front panel of the gas supply apparatus illustrated in FIG. 26.

As illustrated in FIG. 27, the manually operable setting section 163 and the display section 164 are, for example, graphically displayed on the front panel FP10 of the gas supply apparatus 141. The manually operable setting section 163 and display section 164 are divided in, for instance, four graphical setting and display sections 41C to 41F. Because the setting and display sections 41C and 41E are substantially identical to those of the gas supply apparatus 41, the descriptions of which are omitted.

The setting and display section 41D allows the operator to enter instructions related to the pressure inside the first abdominal cavity AC1 and the carbon dioxide gas insufflation thereof. The setting and display section 41D is designed to display the state of the first abdominal cavity AC1 depending on the carbon dioxide gas being insufflated thereinto.

The setting and display section 41F allows the operator to enter instructions related to the pressure inside the second abdominal cavity AC2 and the carbon dioxide gas insufflation thereof. The setting and display section 41F is designed to display the state of the second abdominal cavity AC2 depending on the carbon dioxide gas being insufflated thereinto. The third adapter 41G is attached to the lower side of the setting and display section 41F of the front panel FP 10.

Like the first embodiment, the setting and display section 41D is provided with the pressure displays 77a and 77b, the flow-rate displays 78a and 78b, the total volume display 79, and the excessive pressure indicator 84 as the display section 164 associated with the first abdominal cavity AC1. In addition, the setting and display section 41D is provided with the pressure setting buttons 74a and 74b, the flow-rate setting buttons 75a and 75b, and a first abdominal cavity select button 82 as the manually operable setting section 163 associated with the first abdominal cavity AC1.

The setting and display section 41E is provided with the pressure displays 80a and 80b for the lumen BC as the display section 164 and with the pressure setting buttons 81a and 81b for the lumen BC and the lumen select button 83 as the manually operable setting section 163, the configuration of which is similar to the first embodiment.

In addition, the setting and display section 41F is provided with pressure displays 85a and 85b associated with the second abdominal cavity AC2 as the display section 164.

The setting and display section 41F is also provided with pressure setting buttons 86a and 86b associated with the second abdominal cavity AC2 and a second abdominal cavity select button 87 (see "AC" in FIG. 27) as the manually operable setting section 163.

Click of each of the pressure setting button 74a, the flow-rate setting button 75a, the pressure setting button 81a, and the pressure setting button 85a allows an instruction to be sent to a controller 198 described hereinafter. The instruction is indicative of incrementing a corresponding parameter, such as a first pressure setting for the first abdominal cavity AC1, a flow-rate setting therefor, a luminal pressure setting for the lumen BC, or a second pressure setting for the second abdominal cavity AC2, by, for example, 1 mmHg.

Click of each of the pressure setting button 74b, the flow-rate setting button 75b, the pressure setting button 81b, and the pressure setting button 85b permits an instruction to be sent to the controller 198. The instruction is indicative of decrementing a corresponding parameter, such as the first pressure setting, the flow-rate setting, the luminal pressure setting, or the second pressure setting, by, for example, 1 mmHg.

The right-side pressure display 77a is configured to display a pressure value (in mmHg) based on a measured value of a first pressure sensor 95A described hereinafter. The left-side pressure display 77b is configured to display the first pressure setting determined based on the operations of, for example, the pressure setting buttons 74a and 74b.

The right-side flow-rate display 78a is configured to display a flow-rate (in L/min) based on a measured value of a first flow-rate sensor 96A described hereinafter. The left-side flow-rate display 78b is configured to display the flow-rate setting determined based on operations of, for example, the flow-rate setting buttons 75a and 75b.

The total volume display 79 is configured to display a total amount of carbon dioxide gas calculated by the controller 198 based on the measured values of the first flow-rate sensor 96A, the second flow-rate sensor 96B, and a third flow-rate sensor 96C described hereinafter.

The right-side pressure display 80a is configured to display a pressure (in mmHg) based on a measured value of a second pressure sensor 95B described hereinafter. The left-side pressure display 80b is configured to display the luminal pressure setting determined based on operations of, for example, the pressure setting buttons 81a and 81b.

The right-side pressure display 85a is configured to display a pressure value (in mmHg) based on a measured value of a third pressure sensor 95C described hereinafter. The left-side pressure display 85b is configured to display the second pressure setting determined based on operations of, for example, the pressure setting buttons 86a and 86b.

When the operator turns on the first abdominal cavity select button 82, the button 82 is configured to send to the controller 198 an instruction to make it execute operations for supplying the carbon dioxide gas into the first abdominal cavity AC1. In other words, when the operator turns on the first abdominal cavity select button 82, the button 82 is configured to send to the controller 198 an instruction to designate a first abdominal cavity insufflation mode thereof.

When the operator turns on the lumen select button 83, the button 83 is configured to send to the controller 198 an instruction to make it execute operations for supplying the carbon dioxide gas into the lumen BC. In other words, when the operator turns on the lumen select button 83, the button 83 is configured to send to the controller 198 an instruction to designate a lumen insufflation mode thereof.

When the operator turns on the second abdominal cavity select button 87, the button 87 is configured to send to the controller 198 an instruction to make it execute operations for supplying the carbon dioxide gas into the second abdominal cavity AC2. In other words, when the operator turns on the second abdominal cavity select button 87, the button 87 is configured to send to the controller 198 an instruction to designate a second abdominal cavity insufflation mode thereof.

The excessive pressure indicator 84 is configured to turn on or flash on and off based on a control signal sent from the controller 198 at anytime the pressure measured by the first pressure sensor 95A exceeds a threshold value of the pressure inside the first abdominal cavity AC1 by a predetermined pressure. The turning-on or the flashing of the excessive pressure indicator 84 allows the operator to visually recognize that the pressure inside the first abdominal cavity AC1 exceeds the threshold value by the predetermined pressure or more.

The structures of the manually operable setting section 163 and the display section 164 in the front panel FP10 allow the operator to easily give instructions to the controller 198 and to easily visually recognize the parameters related to the first abdominal cavity AC1, the lumen BC, and the second abdominal cavity AC2.

Incidentally, an excessive pressure indicator that is the same as the excessive pressure sensor 84 may be provided on either the setting and display section 41E or 41F. The excessive pressure indicator is configured to turn on or flash on and off based on a control signal sent from the controller 198 at anytime the pressure measured by the sensor 95B or sensor 95C exceeds a threshold value of the pressure inside the lumen BC or the second abdominal cavity AC2 by a predetermined pressure.

In addition, the center operation panel 8 allows the operator to set the parameters of the gas supply apparatus 141, which include the settings of the pressures inside the first abdominal cavity AC1, the lumen BC, and the second abdominal cavity AC2, and the setting of the flow-rate for the first abdominal cavity AC1. The center display panel 7 can be configured to display at least one of the settings, which has been specified by the operator, displayed on the pressure displays 77a, 77b, 80a, 80b, 85a, and 85b, the flow-rate displays 78a and 78b, and the total volume display 79.

Specifically, the controller 198 operates to send at least one of the settings, which has been specified by the operator, displayed on the pressure displays 77a, 77b, 80a, 80b, 85a, and 85b, flow-rate displays 78a and 78b, and the total volume display 79 to the system controller 5. The system controller 5 receives at least one of the settings sent from the controller 198 to display it on the center display panel 7.

Next, a structure of the gas supply apparatus 141 will be described hereinafter with reference to FIG. 28.

Figure 28:
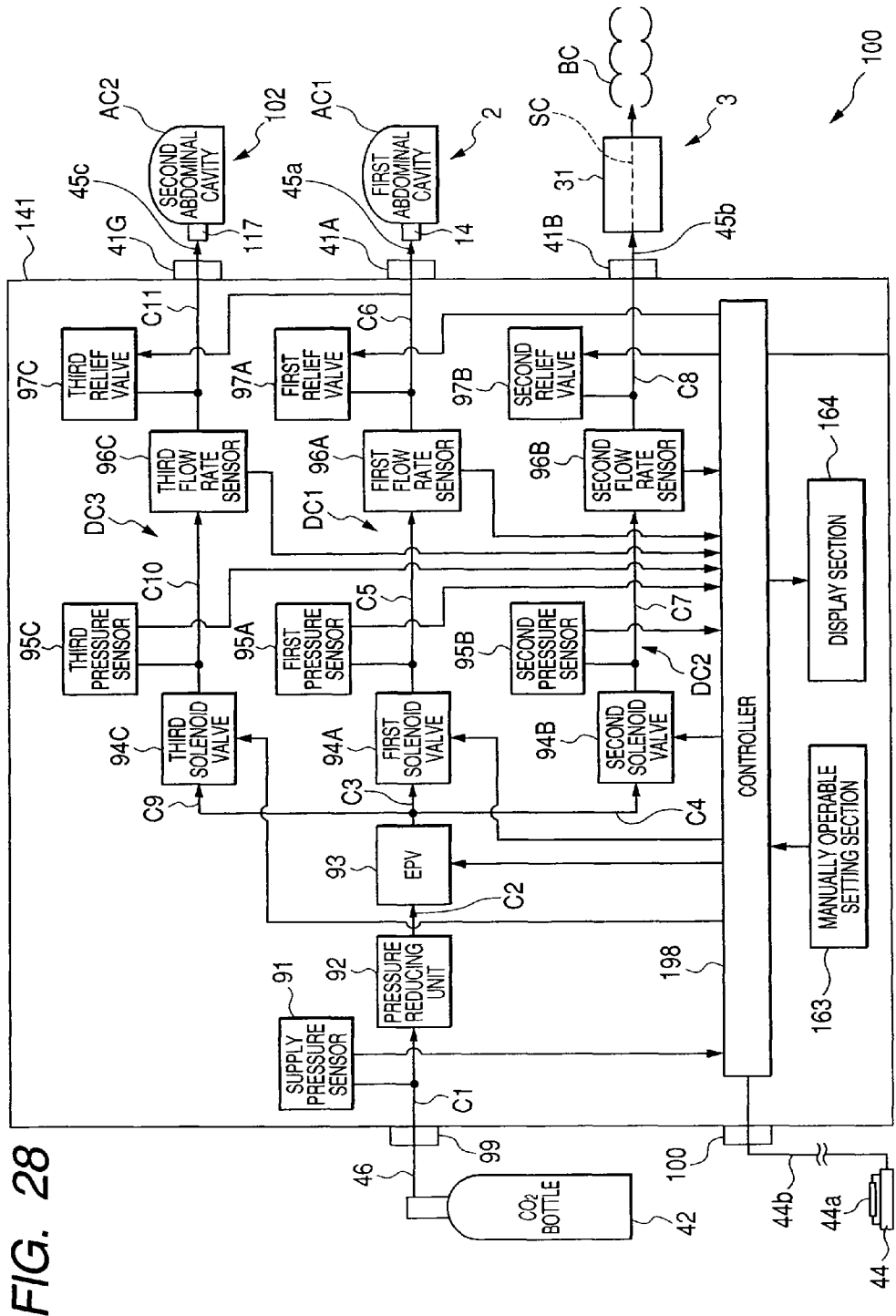
FIG. 28 is a block diagram illustrating a schematic structure of the gas supply apparatus illustrated in FIG. 26.

As shown in FIG. 28, like the first embodiment, the gas supply apparatus 141 includes the controller 198, the manually operable setting section 163, the display section 164, and the first delivery channel C1 coupled to the high-pressure adapter 99. The as supply apparatus 141 includes the supply pressure sensor 91 attached to the first delivery channel C1, the pressure reducing unit 92 coupled to the first delivery channel C1, the second delivery channel C2 coupled to the outlet of the pressure reducing unit 92, and the electropneumatic proportional valve 93 coupled to the second delivery channel C2.

In the eighth embodiment, the first $CO_2$ supply path DC1 coupled to the outlet of the electropneumatic proportional valve 93 constitutes a path through which the carbon dioxide gas is supplied into the first abdominal cavity AC1. The structure of the first $CO_2$ supply path DC1 is the same as that of the first $CO_2$ supply path DC1 shown in FIG. 5, so that the descriptions of the first $CO_2$ supply path DC1 are omitted.

Similarly, the second $CO_2$ supply path DC2 coupled to the outlet of the electropneumatic proportional valve 93 constitutes a path through which the carbon dioxide gas is supplied into the lumen BC. The structure of the second $CO_2$ supply path DC2 is the same as that of the second $CO_2$ supply path DC2 shown in FIG. 5, so that the descriptions of the second $CO_2$ supply path DC2 are omitted.

Furthermore, as illustrated in FIG. 28, the gas supply apparatus 141 includes a ninth delivery channel C9, as a supply path for the second abdominal cavity AC2, coupled to the outlet of the electropneumatic proportional valve 93 and branched from the third delivery channel C3 and the fourth delivery channel C4. In addition, the gas supply apparatus 141 includes a third solenoid valve 94C as an example of open/close valves, a tenth delivery channel C10, a third pressure sensor 95C, a third flow-rate sensor 96C, an eleventh delivery channel C11, and the third adapter 41G.

Specifically, the inlet of the third solenoid valve 94C is communicably coupled to the ninth delivery channel C9, and the outlet of the third solenoid valve 94C is communicably coupled to the tenth delivery channel C10. The tenth delivery channel C10 is communicably coupled to an inlet of the third flow rate sensor 96C whose outlet is communicably coupled through the eleventh delivery channel C11 to the third adapter 41G The third adapter 41G is communicably coupled to the one end of the third tube 45c. The other end of the tube 45b is communicably coupled to the gas delivery channel SC formed inside the flexiblescope 31 through the tube coupler 43a, and the insertion portion 34 of the flexiblescope 31 is inserted into the lumen BC of the patient 10.

In the eighth embodiment, the ninth delivery channel C9, the third solenoid valve 94C, the tenth delivery channel C10, the third flow-rate sensor 96C, the eleventh delivery channel C11, the third adapter 41G and the third tube 45c constitute a third $CO_2$ supply path DC3 directing the carbon dioxide gas into the second abdominal cavity AC2.

Specifically, the carbon dioxide gas whose pressure is regulated by the electropneumatic proportional valve 93 is divided to flow into the third delivery channel C3 for the first abdominal cavity AC1, the fourth delivery channel C4 for the lumen BC, and the ninth delivery channel C9.

The carbon dioxide gas flowing into the third delivery channel C3 is guided into the first abdominal cavity AC1 through the first $CO_2$ supply path DC1, and the carbon dioxide gas flowing into the fourth delivery channel C4 is guided into the lumen BC through the second $CO_2$ supply path DC2. In addition, the carbon dioxide gas flowing into the ninth delivery channel C9 is guided into the second abdominal cavity AC2 through the third $CO_2$ supply path DC3.

Specifically, the downstream side of the electropneumatic proportional valve 93 is separated into the first $CO_2$ supply path DC1, the second $CO_2$ supply path DC2, and the third $CO_2$ supply path DC3 through the third, fourth, and ninth delivery channels C3, C4, and C9, respectively.

Incidentally, in the eighth embodiment, a third delivery member of the present invention corresponds to at least the tenth and eleventh delivery channels C10 and C11 in the third $CO_2$ supply path DC3. Specifically, the concept of the third delivery member of the present invention can expand to cover the whole of the third $CO_2$ supply path DC3 depending on aspects of the gas supply apparatus 141.

Because the elements of the first and second $CO_2$ supply paths DC1 and DC2 have been described in the first embodiment, the descriptions of them are omitted.

The third solenoid valve 94C is electrically connected to the controller 198 and configured to open and close based on control signals sent from the controller 198. The opening and closing of the third solenoid valve 94C allow the third $CO_2$ supply path DC3 to open and close, respectively.

The third pressure sensor 95C is electrically connected to the controller 198. The third pressure sensor 95C has a function of measuring a pressure in the tenth delivery channel C10, in other words, a pressure inside the second abdominal cavity AC2, thereby sending the measured result to the controller 198.

The third flow rate sensor 96C is electrically connected to the controller 198. The third flow rate sensor 96C has a function of detecting the flow rate of the carbon dioxide gas flowing through the third solenoid valve 94C and the tenth and eleventh delivery channel C10 and C11 into the third adapter 41G thereby sending the detected result to the controller 198.

The third relief valve 97C is disposed at the midstream of the eleventh delivery channel C11 between the third flow rate sensor 96C and the third adapter 41G. The third relief valve 97C is electrically connected to the controller 198. The third relief valve 97C is operative to remain in a closed state, and to open based on a control signal sent from the controller 198. The opening of the third relief valve 97C causes carbon dioxide gas in the second abdominal cavity AC2 to be released, thereby reducing a pressure inside the second abdominal cavity AC2.

In the structure of the gas supply apparatus 141 according to the eighth embodiment, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46, the high pressure adapter 99, and the first delivery channel C1 of the gas supply apparatus 141. The carbon dioxide gas is reduced in pressure by the pressure reducing unit 92 to have the predetermined pressure. Thereafter, the carbon dioxide gas is delivered to the electropneumatic proportional valve 93 so that the pressure and flow-rate are regulated based on the control signals sent from the controller 198.

The carbon dioxide gas with its pressure and flow-rate regulated is selectively switched to at least one of the first $CO_2$ supply path DC1, the second $CO_2$ supply path DC2, and the third $CO_2$ supply path DC3. The carbon dioxide gas, which is switched to the first $CO_2$ supply path DC1, is supplied into the first abdominal cavity AC1 therethrough; the carbon dioxide gas, which is switched to the second $CO_2$ supply path DC2, is supplied into the lumen BC therethrough. Moreover, the carbon dioxide gas, which is switched to the third $CO_2$ supply path DC3, is supplied into the second abdominal cavity AC2 therethrough.

Next, operations of the gas supply apparatus 141 according to the eighth embodiment will be described hereinafter.

Firstly, operations of the gas supply apparatus 141 in cases where the operator carries out surgical procedure to supply the carbon dioxide gas into both the first abdominal cavity AC1 and the lumen BC with the use of the gas supply apparatus 141 will be described hereinafter.

As illustrated in FIGS. 26 and 31, a health worker, such as an operator or a nurse, establishes, as an introduction step, the first $CO_2$ supply path DC1 and the second $CO_2$ supply path DC2 in order to supply the carbon dioxide gas into both the first abdominal cavity AC1 and the lumen BC.

Specifically, the health worker prepares the first tube 45a to couple the one end of the tube 45a to the first adapter 41A of the gas supply apparatus 141 and the other end thereof to the first trocar 14 to create the first $CO_2$ supply path DC1. Next, the health worker attaches the adapter 43 to the base 38 of the flexiblescope 31. Thereafter, the health worker prepares the second tube 45b to couple the one end of the tube 45b to the second adapter 41B of the gas supply apparatus 141 and the other end thereof to the tube coupling portion 43a of the adapter 43 to create the second $CO_2$ supply path DC2.

When the power switch 71 is turned on by, for example, the operator as an operation step, the measured value by the first pressure sensor 95A is displayed on the pressure display 77a of the front panel FP10, and the measured value by the second pressure sensor 95B is displayed on the pressure display 80a thereof. In addition, the foot switch 44 becomes a state that allows the operator to operate it.

On the pressure display 77b, the first pressure setting for the first abdominal cavity AC1, which has been previously set on, for example, the center operation panel 8, is displayed. Similarly, on the flow-rate display 78b, the flow-rate setting of the carbon dioxide gas to be insufflated into the first abdominal cavity AC1, which has been previously set on, for example, the center operation panel 8, is displayed.

Furthermore, on the pressure display 80b, the luminal pressure setting for the lumen BC, which has been previously set on, for example, the center operation panel 8, is displayed.

In cases where no first pressure setting for the first abdominal cavity AC1 has been previously determined on the center operating panel 8, the operator appropriately operates, as an operation step, the pressure setting buttons 74a and 74b to determine the first pressure setting for the first abdominal cavity AC1. The instruction corresponding to the first pressure setting for the first abdominal cavity AC1 is sent from the manually operable setting section 163 to the controller 198 so that the first pressure setting is displayed on the pressure display 77b by the controller 198.

Similarly, in cases where no flow-rate setting for insufflation of the first abdominal cavity AC1 has been previously determined on the center operating panel 8, the operator appropriately operates, as an operation step, the flow-rate setting buttons 75a and 75b. The instruction corresponding to the flow-rate setting for insufflation of the first abdominal cavity AC1 is sent from the manually operable setting section 163 to the controller 198 so that the flow-rate setting is displayed on the pressure display 78b by the controller 198.

In addition, no luminal pressure setting for the lumen BC has been previously determined on the center operating panel 8, the operator appropriately operates, as an operation step, the pressure setting buttons 81a and 81b to determine the luminal pressure setting for the lumen BC. The instruction corresponding to the luminal pressure setting is sent from the manually operable setting section 163 to the controller 198 so that the luminal pressure setting is displayed on the pressure display 81b by the controller 198.

Subsequently, the health worker opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 141. The gas flowing into the apparatus 141 is introduced through the first delivery channel C1 to the pressure reducing unit 92.

The carbon dioxide gas is reduced in pressure by the pressure reducing unit 92 to have the predetermined pressure, thereby being guided via the second delivery channel C2 to the inlet of the electropneumatic proportional valve 93.

Under a state before surgery, the electropneumatic proportional valve 93 remains closed, which causes the carbon dioxide gas not to flow the downstream thereof.

At that time, the supply pressure sensor 91 measures the pressure supplied from the $CO_2$ bottle 42 to the pressure reducing unit 92 through the first delivery channel C1 to send the measured value to the controller 198. As a result, the controller 198 calculates the volume of the carbon dioxide gas remaining in the $CO_2$ bottle 42 to display it on the gas remaining volume indicators 76.

Under the operating state of the gas supply apparatus 141 set forth above, the operator, as an introduction step, inserts the rigidscope 21 into the first abdominal cavity AC1 with the flexiblescope 31 being inserted into the lumen BC, such as a large intestine present in the first abdominal cavity AC1. The operator specifies and treats at least one site to be treated in the first abdominal cavity AC1 and/or the lumen BC based on the first and second images picked up by the rigidscope 21 and the flexiblescope 31, respectively. After the identification of the at least one site to be treated, the operator treats the specified site as a treatment step.

Specifically, operations of the first abdominal cavity select button 82 and the gas-supply start button 72 allow the controller 198 to start the carbon dioxide gas insufflation of the first abdominal cavity AC1 with the pressure of the carbon dioxide gas regulated suitable therefor. On the other hand, operations of the lumen select button 83 and the foot switch 44 allow the controller 198 to start the carbon dioxide gas insufflation of the lumen BC with the pressure of the carbon dioxide gas regulated suitable therefor.

Next, an example of control operations of the controller 198 of the gas supply apparatus 141 when insufflating the carbon dioxide gas into both the first abdominal cavity AC1 and the lumen BC will be described hereinafter with reference to FIG. 29.

If the first abdominal cavity select button 82, the lumen select button 83, and the gas-supply start button 72 are in on state, respectively, the controller 198 enters the first abdominal cavity and lumen insufflation mode. In the first abdominal cavity and lumen insufflation mode, the controller 198 obtains an actual (current) pressure inside the first abdominal cavity AC1 based on the pressure value that is measured by the first pressure sensor 95A with the first solenoid valve 94A closed in step S101 of FIG. 29.

Next, the controller 198 determines whether the obtained pressure reaches the first pressure setting, as a first abdominal cavity target pressure Pa, set on the front panel FP10 and displayed on the pressure display 77b (step S102).

When it is determined that the obtained pressure does not reach the first abdominal cavity target pressure Pa (the obtained pressure<Pa), the determination in step S102 is YES so that the controller 198 shifts to step S103. In contrast, when it is determined that the obtained pressure reaches the first abdominal cavity target pressure Pa (the obtained pressure Pa), the determination in step S102 is NO so that the controller 198 shifts to step S104.

In step S103, the controller 198 calculates the difference between the obtained pressure and the first abdominal cavity target pressure Pa to control the opening of the electropneumatic proportional valve 93 based on the calculated difference. The control of the opening of the electropneumatic proportional valve 93 allows the pressure of the carbon dioxide gas flowing out of the valve 93 to be regulated within the corresponding appropriate range of, for example, 0 to 80 mmHg or thereabout.

In addition, in step S103, the controller 198 determines an opening period of the first solenoid valve 94A based on the calculated difference, and sends the control signal to the first solenoid valve 94A to open it during the determined opening period. This allows the flow-rate of the carbon dioxide gas flowing out of the first solenoid valve 94A to be regulated within the corresponding appropriate range of, for example, 0.1 to 35 L/min or thereabout.

Specifically, a predetermined volume of the carbon dioxide gas whose pressure and flow-rate are regulated is supplied through the fifth delivery channel C5, the first flow rate sensor 96A, the sixth delivery channel C6, and the first adapter 41A. Thereafter, the carbon dioxide gas is delivered through the first tube 45a and the first trocar 14 to be supplied into the first abdominal cavity AC1.

In step S104, the controller 198 obtains an actual (current) pressure inside the lumen BC based on the pressure value that is measured by the second pressure sensor 95B with the second solenoid valve 94B closed.

Next, the controller 198 determines whether the obtained pressure reaches the luminal pressure setting, as a luminal target pressure Pb, set on the front panel FP10 and displayed on the pressure display 80b in step S105.

When it is determined that the obtained pressure does not reach the luminal target pressure Pb (the obtained pressure<Pb), the determination in step S105 is YES so that the controller 198 shifts to step S106. In contrast, when it is determined that the obtained pressure reaches the luminal target pressure Pb (the obtained pressure Pb), the determination in step S105 is NO so that the controller 198 shifts to step S107.

In step S106, the controller 198 calculates the difference between the obtained pressure and the luminal target pressure Pb to control the opening of the electropneumatic proportional valve 93 based on the calculated difference. The control of the opening of the electropneumatic proportional valve 93 allows the pressure of the carbon dioxide gas flowing out of the valve 93 to be regulated within the corresponding appropriate range of, for example, 0 to 500 mmHg or thereabout.

In addition, in step S106, the controller 198 determines an opening period of the second solenoid valve 94B based on the calculated difference, and sends the control signal to the second solenoid valve 94B to open it during the determined opening period. This allows the flow-rate of the carbon dioxide gas flowing out of the second solenoid valve 94B to be regulated within the corresponding appropriate range of, for example, 1 to 3 L/min or thereabout.

Specifically, a predetermined volume of the carbon dioxide gas whose pressure and flow-rate are regulated is supplied through the seventh delivery channel C7, the second flow rate sensor 96B, the eighth delivery channel C8, and the second adapter 41B. Thereafter, the carbon dioxide gas is delivered into the lumen BC through the second tube 45b, the adapter 43, and the gas delivery channel SC inside the flexiblescope 31.

In step S107, the controller 198 determines whether the obtained pressure inside the first abdominal cavity AC1 is equal to or higher than the first abdominal cavity target pressure Pa and the obtained pressure inside the lumen BC is equal to or higher than the luminal target pressure Pb.

When it is determined that the obtained pressure inside the first abdominal cavity AC1 and that inside the lumen BC are equal to or higher than the first abdominal cavity target pressure Pa and the luminal target pressure Pb, respectively, (the obtained pressure inside the first abdominal cavity≧Pa, the obtained pressure inside the lumen≧Pb), the determination in step S107 is YES. In this affirmative determination, for example, the controller 198 controls the first and second solenoid valves 95A and 95B to close them, thereby interrupting the carbon dioxide gas insufflations of both the first abdominal cavity AC1 and the lumen BC.

In contrast, when it is determined that at least one of the obtained pressure inside the first abdominal cavity AC1 and the obtained pressure inside the lumen BC is lower than at least one of the first abdominal cavity target pressure Pa and the luminal target pressure Pb, the determination in step S107 is NO. In this negative determination, the controller 198 returns to step S101, and repeatedly executes the operations in steps S101 to S107. These operations in steps S101 to S107 allow the actual pressure inside the first abdominal cavity AC1 and that inside the lumen BC to rise greater than the corresponding first abdominal cavity target pressure Pa and the luminal target pressure Pb, respectively.

As set forth above, in the gas supply apparatus 141 according to the eighth embodiment, the controller 198 obtains an actual pressure inside the first abdominal cavity AC1 and that inside the lumen BC. Based on the obtained actual pressures, the controller 198 allows the carbon dioxide gas insufflations of the first abdominal cavity AC1 and the lumen BC while regulating the pressure and the flow-rate of the carbon dioxide gas within the appropriate ranges for the first abdominal cavity AC1 and the lumen BC, respectively.

In addition, the controller 198 permits the alternative carbon dioxide gas insufflations of the first abdominal cavity AC1 and the lumen BC while checking whether the actual pressure inside the first abdominal cavity AC1 and that inside the lumen BC are lower than the corresponding first abdominal cavity target pressure Pa and the luminal target pressure Pb, respectively. These alternative carbon dioxide gas insufflations of the first abdominal cavity AC1 and the lumen BC make it possible to set the actual pressure inside the first abdominal cavity AC1 and that inside the lumen BC to be higher than the first abdominal cavity target pressure Pa and the luminal target pressure Pb, respectively.

Figure 30:
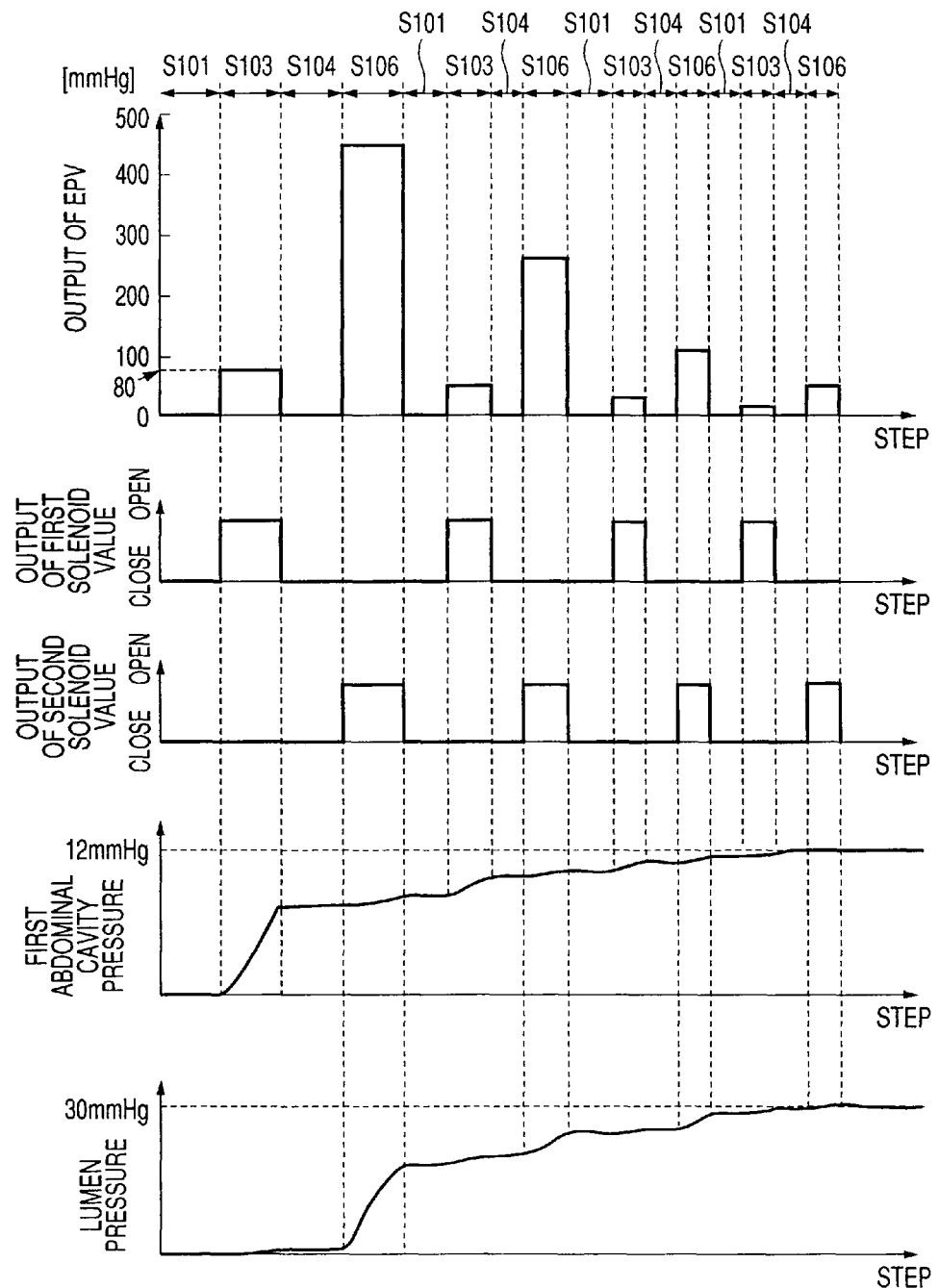
FIG. 30 is a sequence diagram schematically illustrating a control operation sequence performed by the controller illustrated in FIG. 28.

Specifically, as illustrated in FIG. 30 as an example, the controller 198 controls the first and second solenoid valves 94A and 94B to open/close them while controlling the opening of the electropneumatic proportional valve 93 to regulate the discharge pressure thereof. These controls of the controller 198 permit the alternative carbon dioxide gas insufflations of the first abdominal cavity AC1 and the lumen BC with the pressure and the flow-rate of the carbon dioxide gas regulated within the appropriate ranges for the first abdominal cavity AC1 and the lumen BC, respectively.

These alternative carbon dioxide gas insufflations of the first abdominal cavity AC1 and the lumen BC allow the actual pressure inside the first abdominal cavity AC1 and that inside the lumen BC to gradually rise. This makes it possible for the actual pressure inside the first abdominal cavity AC1 and that inside the lumen BC to reach 12 mmHg and 30 mmHg as examples of the first abdominal cavity target pressure Pa and the luminal target pressure Pb, respectively (see FIG. 30).

As described above, in the eighth embodiment of the present invention, the gas supply apparatus 141 with the first and second $CO_2$ supply paths DC1 and DC2 is configured to supply the carbon dioxide gas into both the first abdominal cavity AC1 and the lumen BC through the first and second $CO_2$ supply paths DC1 and DC2.

Like each of the aforementioned embodiments, the configuration of the gas supply apparatus 141 allows expansion of the field of each of the rigidscope 21 and the flexiblescope 31 in each of the first abdominal cavity AC1 and the lumen BC. In addition, the configuration of the gas supply apparatus 141 can provide a sufficient space for manipulating treatment tools in each of the first abdominal cavity AC1 and the lumen BC, which are similar to each of the aforementioned embodiments.

In addition, in the eighth embodiment, it is possible to set the pressure of the carbon dioxide gas to be insufflated into alternatively the first abdominal cavity AC1 and the lumen BC based on the measurement results corresponding to the actual pressures inside the first abdominal cavity AC1 and the lumen BC, respectively. This can prevent the pressure inside each of the first abdominal cavity AC1 and the lumen BC from rapidly increasing.

Secondary, operations of the gas supply apparatus 141 in cases where the operator carries out surgical procedure to supply the carbon dioxide gas into both the first abdominal cavity AC1 and the second abdominal cavity AC2 with the use of the gas supply apparatus 141 will be described hereinafter.

As illustrated in FIG. 31, a health worker, such as an operator or a nurse, establishes, as an introduction step, the first $CO_2$ supply path DC1 and the third $CO_2$ supply path DC3 in order to supply the carbon dioxide gas into both the first and second abdominal cavities AC1 and AC2.

Specifically, in addition to the operations to create the first $CO_2$ supply path DC1 described above, the health worker prepares the third tube 45c to couple the one end of the tube 45c to the third adapter 41G of the gas supply apparatus 141 and the other end thereof to the fourth trocar 117 to create the third $CO_2$ supply path DC3.

When the power switch 71 is turned on by, for example, the operator as an operation step, the measured value by the first pressure sensor 95A is displayed on the pressure display 77a of the front panel FP10, and the measured value by the third pressure sensor 95C is displayed on the pressure display 85a of the front panel FP10.

On the pressure display 77b, the first pressure setting for the first abdominal cavity AC1, which has been previously set on, for example, the center operation panel 8, is displayed. Similarly, on the pressure display 85b, the second pressure setting for the second abdominal cavity AC2 has been previously set on, for example, the center operation panel 8, is displayed.

Next, the health worker opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 141. The gas flowing into the apparatus 141 is introduced through the first delivery channel C1 to the pressure reducing unit 92.

The carbon dioxide gas is reduced in pressure by the pressure reducing unit 92 to have the predetermined pressure, thereby being guided via the second delivery channel C2 to the inlet of the electropneumatic proportional valve 93.

Under a state before surgery, the electropneumatic proportional valve 93 remains closed, which causes the carbon dioxide gas not to flow the downstream thereof.

At that time, the supply pressure sensor 91 measures the pressure supplied from the $CO_2$ bottle 42 to the pressure reducing unit 92 through the first delivery channel C1 to send the measured value to the controller 198. As a result, the controller 198 calculates the volume of the carbon dioxide gas remaining in the $CO_2$ bottle 42 to display it on the gas remaining volume indicators 76.

Under the operating state of the gas supply apparatus 141 set forth above, the operator, as an introduction step, inserts the rigidscope 21 into the inside of the first abdominal cavity AC1, and inserts the rigidscope 121 into the second abdominal cavity AC2. The operator specifies and treats at least one site to be treated in the first abdominal cavity AC1 and/or the second abdominal cavity AC2 based on the first and third images picked up by the rigidscopes 21 and 121, respectively. After the identification of the at least one site to be treated, the operator treats the specified site as a treatment step.

Specifically, operations of the first and second abdominal cavity select buttons 82 and 87, and the gas-supply start button 72 allow the controller 198 to start the carbon dioxide gas insufflations of the first and second abdominal cavities AC1 and AC2 with the pressure of the carbon dioxide gas regulated suitable therefor.

Next, an example of control operations of the controller 198 of the gas supply apparatus 141 when insufflating the carbon dioxide gas into both the first and second abdominal cavities AC1 and AC2 will be described hereinafter with reference to FIG. 32.

If the first abdominal cavity select button 82, the second abdominal cavity select button 87, and the gas-supply start button 72 are in on state, respectively, the controller 198 enters the first and second abdominal cavity insufflation mode. In the first and second abdominal cavity insufflation mode, the controller 198 obtains an actual (current) pressure inside the first abdominal cavity AC1 based on the pressure value that is measured by the first pressure sensor 95A with the first solenoid valve 94A closed in step S111 of FIG. 32.

Next, the controller 198 determines whether the obtained pressure reaches the first pressure setting (the first abdominal cavity target pressure Pa) set on the front panel FP10 and displayed on the pressure display 77b (step S112).

When it is determined that the obtained pressure does not reach the first abdominal cavity target pressure Pa, the determination in step S112 is YES so that the controller 198 shifts to step S113. In contrast, when it is determined that the obtained pressure reaches the first abdominal cavity target pressure Pa, the determination in step S112 is NO so that the controller 198 shifts to step S114.

Figure 29:
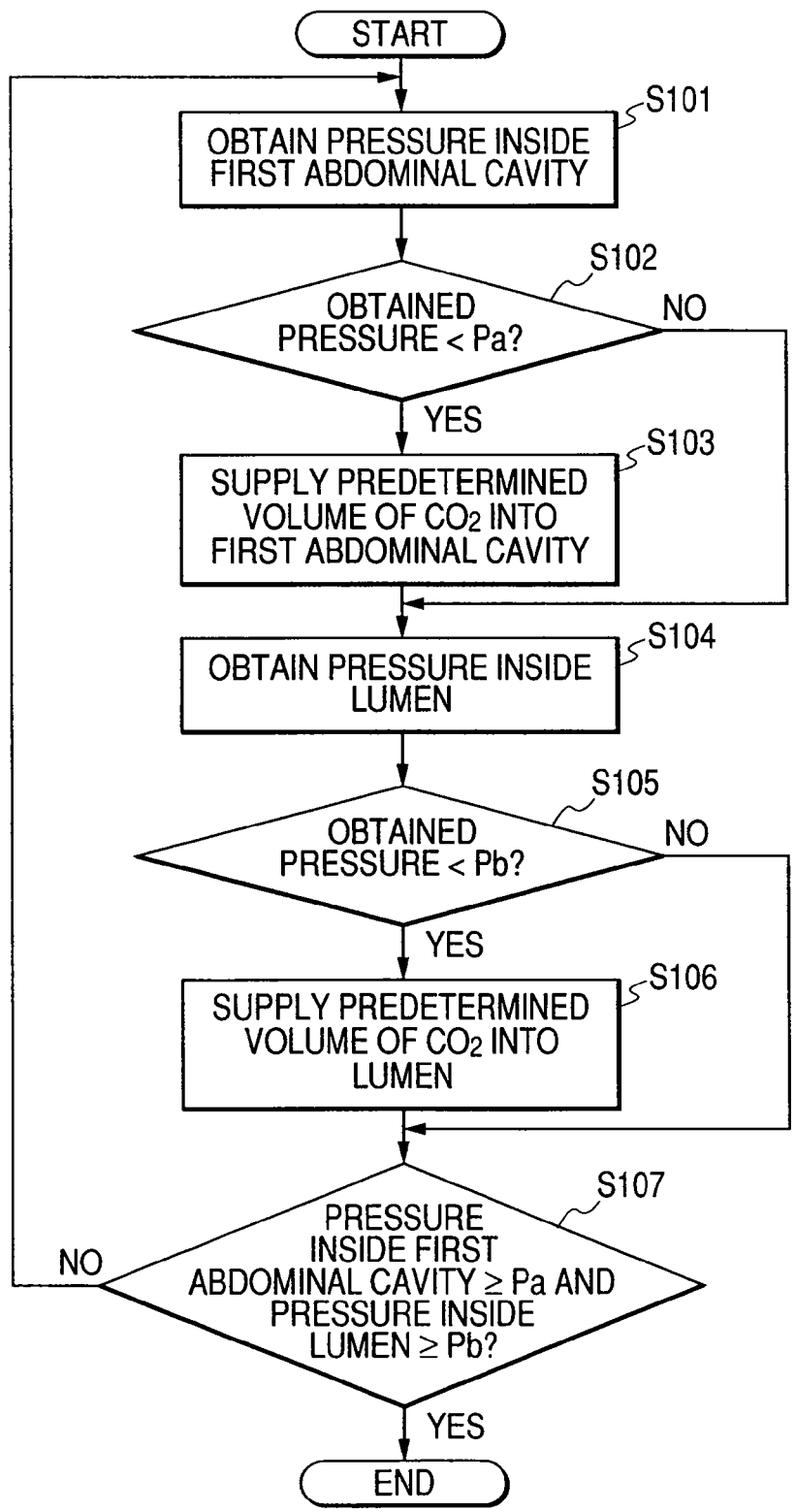
FIG. 29 is a flowchart schematically illustrating an example of control operations of a controller illustrated in FIG. 28.

In step S113, the controller 198 executes the operations similar in step S103 of FIG. 29 to regulate the pressure and the flow-rate of the carbon dioxide gas discharged from the electropneumatic proportional valve 93 and to control the first solenoid valve 94A to open it. This allows a predetermine volume of the carbon dioxide gas with the regulated pressure and flow-rate to be supplied into the first abdominal cavity AC1.

In step S114, the controller 198 obtains an actual (current) pressure inside the second abdominal cavity AC2 based on the pressure value that is measured by the third pressure sensor 95C with the third solenoid valve 94C closed.

Next, the controller 198 determines whether the obtained pressure reaches the second pressure setting, as a second abdominal cavity target pressure Pc, set on the front panel FP10 and displayed on the pressure display 85b in step S115.

When it is determined that the obtained pressure does not reach the second abdominal cavity target pressure Pc (the obtained pressure<Pc), the determination in step S115 is YES so that the controller 198 shifts to step S116. In contrast, when it is determined that the obtained pressure reaches the second abdominal cavity target pressure Pc (the obtained pressure Pc), the determination in step S115 is NO so that the controller 198 shifts to step S117.

In step S116, the controller 198 calculates the difference between the obtained pressure and the second abdominal cavity target pressure Pc to control the opening of the electropneumatic proportional valve 93 based on the calculated difference. The control of the opening of the electropneumatic proportional valve 93 allows the pressure of the carbon dioxide gas flowing out of the valve 93 to be regulated within the corresponding appropriate range of, for example, 0 to 500 mmHg or thereabout.

In addition, in step S116, the controller 198 determines an opening period of the third solenoid valve 94C based on the calculated difference, and sends the control signal to the third solenoid valve 94C to open it during the determined opening period. This allows the flow-rate of the carbon dioxide gas flowing out of the third solenoid valve 94C to be regulated within the corresponding appropriate range of, for example, 0.1 to 35 L/min or thereabout.

Specifically, a predetermined volume of the carbon dioxide gas whose pressure and flow-rate are regulated is supplied through the tenth delivery channel C10, the third flow rate sensor 96C, the eleventh delivery channel C11, and the third adapter 41G. Thereafter, the carbon dioxide gas is delivered into the second abdominal cavity AC2 through the third tube 45c and the fourth trocar 117.

In step S117, the controller 198 determines whether the obtained pressure inside the first abdominal cavity AC1 is equal to or higher than the first abdominal cavity target pressure Pa and the obtained pressure inside the second abdominal cavity AC2 is equal to or higher than the second abdominal cavity target pressure Pc.

When it is determined that the obtained pressures inside the first and second abdominal cavities AC1 and AC2 are equal to or higher than the first and second abdominal cavity target pressures Pa and Pc, respectively, (the obtained pressures inside the first and second abdominal cavities≧Pa and Pc), the determination in step S117 is YES. In this affirmative determination, for example, the controller 198 controls the first and third solenoid valves 95A and 95C to close them, thereby interrupting the carbon dioxide gas insufflations of both the first and second abdominal cavities AC1 and AC2.

In contrast, when it is determined that at least one of the obtained pressures inside the first and second abdominal cavities AC1 and AC2 is lower than at least one of the first and second abdominal cavity target pressures Pa and Pc, the determination in step S117 is NO. In this negative determination, the controller 198 returns to step S111, and repeatedly executes the operations in steps S111 to S117. These operations in steps S111 to S117 allow the actual pressures inside the first and second abdominal cavities AC1 and AC2 to rise greater than the corresponding first and second abdominal cavity target pressures Pa and Pc, respectively.

That is, in the gas supply apparatus 141 according to the eighth embodiment, the controller 198 obtains an actual pressure inside the first abdominal cavity AC1 and that inside the second abdominal cavity AC2. Based on the obtained actual pressures, the controller 198 allows the carbon dioxide gas insufflations of the first and second abdominal cavities AC1 and AC2 while regulating the pressure and the flow-rate of the carbon dioxide gas within the appropriate ranges for the first and second abdominal cavities AC1 and AC2, respectively.

In addition, the controller 198 permits the alternative carbon dioxide gas insufflations of the first and second abdominal cavities AC1 and AC2 while checking whether the actual pressures inside the first and second abdominal cavities AC1 and AC2 are lower than the corresponding first and second abdominal cavity target pressures Pa and Pc, respectively. These alternative carbon dioxide gas insufflations of the first and second abdominal cavities AC1 and AC2 make it possible to set the actual pressures inside the first and second abdominal cavities AC1 and AC2 to be higher than the first and second abdominal cavity target pressures Pa and Pc, respectively.

As described above, in the eighth embodiment of the present invention, the gas supply apparatus 141 with the first and third $CO_2$ supply paths DC1 and DC3 is configured to supply the carbon dioxide gas into both the first and second abdominal cavities AC1 and AC2 through the first and third $CO_2$ supply paths DC1 and DC3.

Like each of the aforementioned embodiments, the configuration of the gas supply apparatus 141 allows expansion of the field of each of the rigidscopes 21 and 121 in each of the first and second abdominal cavities AC1 and AC2. In addition, the configuration of the gas supply apparatus 141 can provide a sufficient space for manipulating treatment tools in each of the first and second abdominal cavities AC1 and AC2, which are similar to each of the aforementioned embodiments.

In addition, in the eighth embodiment, it is possible to set the pressure of the carbon dioxide gas to be insufflated into alternatively the first and second abdominal cavities AC1 and AC2 based on the measurement results corresponding to the actual pressures inside the first and second abdominal cavities AC1 and AC2, respectively. This can prevent the pressure inside each of the first and second abdominal cavities AC1 and AC2 from rapidly increasing.

Note that, in the eighth embodiment, when insufflating the carbon dioxide gas into the lumen BC and another lumen, preparation of a plurality of endoscope systems having a plurality of flexiblescopes allows the carbon dioxide gas insufflations of the lumen BC and another lumen in the same manner as the carbon dioxide gas insufflations of the first and second abdominal cavities AC1 and AC2.

Thirdly, operations of the gas supply apparatus 141 in cases where the operator carries out surgical procedure to supply the carbon dioxide gas into the first and second abdominal cavities AC1 and AC2 and the lumen BC with the use of the gas supply apparatus 141 will be described hereinafter.

Figure 33:
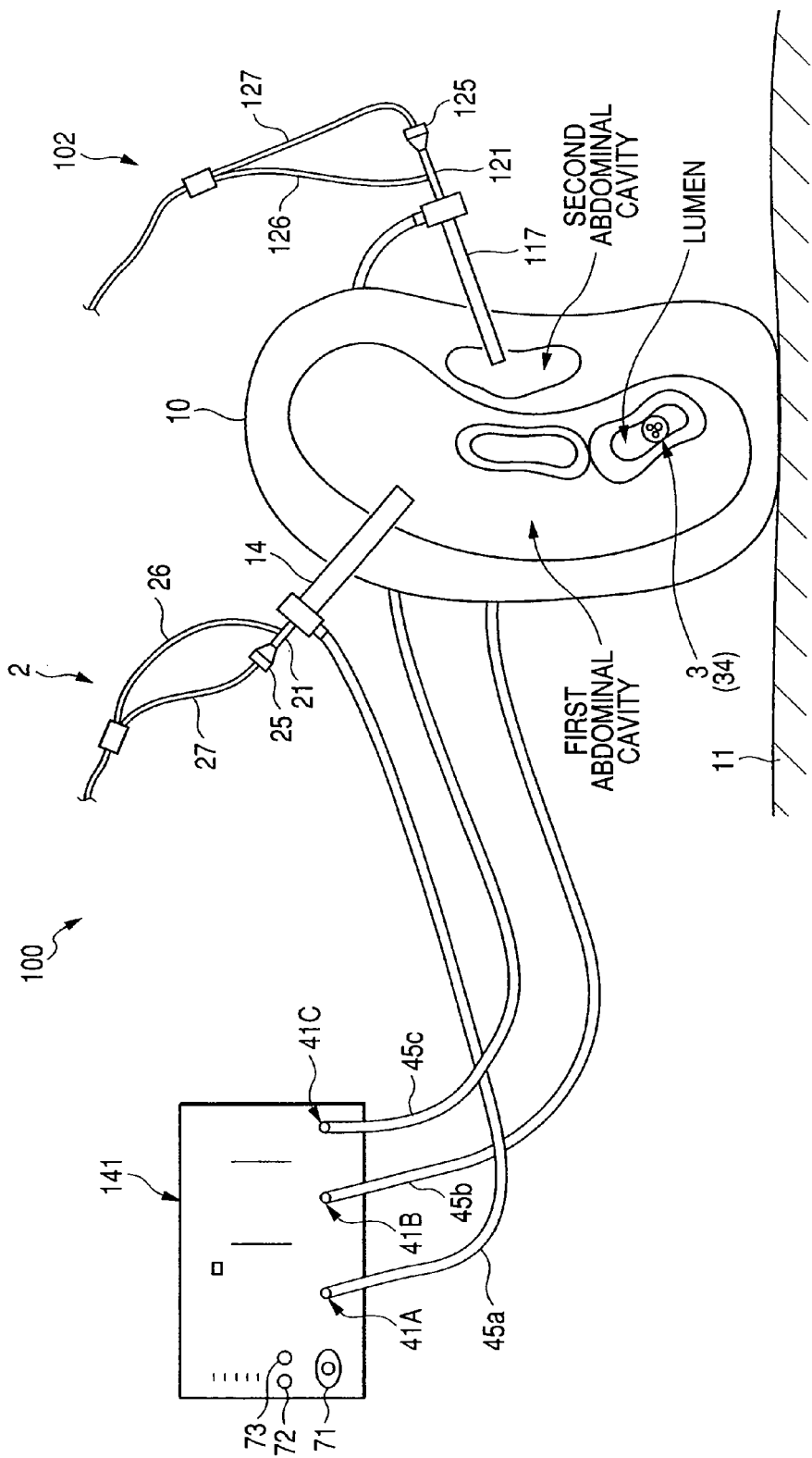
FIG. 33 is a view schematically illustrating service conditions of the gas supply apparatus according to the eighth embodiment when insufflating a carbon dioxide gas into a first abdominal cavity, a lumen, and a second abdominal cavity of a patient.

As illustrated in FIGS. 26 and 33, a health worker, such as an operator or a nurse, establishes, as an introduction step, the first, second, and third $CO_2$ supply paths DC1, DC2, and DC3 in order to supply the carbon dioxide gas into the first abdominal cavity AC1, the second abdominal cavity AC2, and the lumen BC, respectively. These establishment procedures of the paths DC1 to DC3 have been described hereinbefore.

When the power switch 71 is turned on by, for example, the operator as an operation step, the measured value by the first pressure sensor 95A is displayed on the pressure display 77a of the front panel FP10, and the measured value by the second pressure sensor 95B is displayed on the pressure display 80a thereof. In addition, the measured value by the third pressure sensor 95C is displayed on the pressure display 85a of the front panel FP10, and the foot switch 44 becomes a state that allows the operator to operate it.

On the pressure display 77b, the first pressure setting for the first abdominal cavity AC1, which has been previously set on, for example, the center operation panel 8, is displayed. Similarly, on the pressure display 78b, the flow-rate seting of the carbon dioxide gas to be insufflated into the first abdominal cavity AC1, which has been previously set on, for example, the center operation panel 8, is displayed.

Next, the health worker opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 141. The gas flowing into the apparatus 141 is introduced through the first delivery channel C1 to the pressure reducing unit 92.

The carbon dioxide gas is reduced in pressure by the pressure reducing unit 92 to have the predetermined pressure, thereby being guided via the second delivery channel C2 to the inlet of the electropneumatic proportional valve 93.

Under a state before surgery, the electropneumatic proportional valve 93 remains closed, which causes the carbon dioxide gas not to flow the downstream thereof.

At that time, the supply pressure sensor 91 measures the pressure supplied from the $CO_2$ bottle 42 to the pressure reducing unit 92 through the first delivery channel C1 to send the measured value to the controller 198. As a result, the controller 198 calculates the volume of the carbon dioxide gas remaining in the $CO_2$ bottle 42 to display it on the gas remaining volume indicators 76.

Under the operating state of the gas supply apparatus 141 set forth above, the operator, as an introduction step, inserts:

the rigidscope 21 into the first abdominal cavity AC1;
the flexiblescope 31 into the lumen BC; and
the rigidscope 121 into the second abdominal cavity AC2.

The operator specifies and treats at least one site to be treated in the first abdominal cavity AC1, the lumen BC, and/or the second abdominal cavity AC2 based on the first to third images picked up by the rigidscopes 21, the flexiblescope 31, and the rigidscope 121, respectively. After the identification of the at least one site to be treated, the operator treats the specified site as a treatment step.

Specifically, operations of the first and second abdominal cavity select buttons 82 and 87, and the gas-supply start button 72 allow the controller 198 to start the carbon dioxide gas insufflations of the first and second abdominal cavities AC1 and AC2 with the pressure of the carbon dioxide gas regulated suitable therefor. In addition, operations of the lumen select button 83 and the foot switch 44 allow the controller 198 to start the carbon dioxide gas insufflation of the lumen BC with the pressure of the carbon dioxide gas regulated suitable therefor.

Next, an example of control operations of the controller 198 of the gas supply apparatus 141 when insufflating the carbon dioxide gas into the first and second abdominal cavities AC1 and AC2, and the lumen BC will be described hereinafter with reference to FIG. 34.

If the first abdominal cavity select button 82, the lumen select button 83, the second abdominal cavity select button 87, and the gas-supply start button 72 are in on state, respectively, the controller 198 enters the first and second abdominal cavity and lumen insufflation mode. In the first and second abdominal cavity and lumen insufflation mode, the controller 198 obtains an actual (current) pressure inside the first abdominal cavity AC1 based on the pressure value that is measured by the first pressure sensor 95A with the first solenoid valve 94A closed in step S121 of FIG. 34.

Next, the controller 198 determines whether the obtained pressure reaches the first pressure setting (the first abdominal cavity target pressure Pa) set on the front panel FP10 and displayed on the pressure display 77b (step S122).

When it is determined that the obtained pressure does not reach the first abdominal cavity target pressure Pa, the determination in step S122 is YES so that the controller 198 shifts to step S123. In contrast, when it is determined that the obtained pressure reaches the first abdominal cavity target pressure Pa, the determination in step S122 is NO so that the controller 198 shifts to step S124.

In step S123, the controller 198 executes the operations similar in step S103 of FIG. 29 to regulate the pressure and the flow-rate of the carbon dioxide gas discharged from the electropneumatic proportional valve 93 and to control the first solenoid valve 94A to open it. This permits a predetermine volume of the carbon dioxide gas with the regulated pressure and flow-rate to be supplied into the first abdominal cavity AC1.

In step S124, the controller 198 obtains an actual (current) pressure inside the lumen BC based on the pressure value that is measured by the second pressure sensor 95B with the second solenoid valve 94B closed.

Next, the controller 198 determines whether the obtained pressure reaches the luminal pressure setting (the luminal target pressure Pb) set on the front panel FP10 and displayed on the pressure display 80b in step S125.

When it is determined that the obtained pressure does not reach the luminal target pressure Pb (the obtained pressure<Pb), the determination in step S125 is YES so that the controller 198 shifts to step S126. In contrast, when it is determined that the obtained pressure reaches the luminal target pressure Pb (the obtained pressure≧Pb), the determination in step S125 is NO so that the controller 198 shifts to step S127.

In step S126, the controller 198 executes the operations similar in step S106 of FIG. 29 to regulate the pressure and the flow-rate of the carbon dioxide gas discharged from the electropneumatic proportional valve 93 and to control the second solenoid valve 94B to open it. This causes a predetermine volume of the carbon dioxide gas with the regulated pressure and flow-rate to be supplied into the lumen BC.

Subsequently, the controller 198 obtains an actual (current) pressure inside the second abdominal cavity AC2 based on the pressure value that is measured by the third pressure sensor 95C with the third solenoid valve 94C closed.

Next, the controller 198 determines whether the obtained pressure reaches the second pressure setting (the second abdominal cavity target pressure Pc) set on the front panel FP10 and displayed on the pressure display 85b in step S128.

When it is determined that the obtained pressure does not reach the second abdominal cavity target pressure Pc (the obtained pressure<Pc), the determination in step S128 is YES so that the controller 198 shifts to step S129. In contrast, when it is determined that the obtained pressure reaches the second abdominal cavity target pressure Pc (the obtained pressure Pc), the determination in step S128 is NO so that the controller 198 shifts to step S129.

Figure 32:
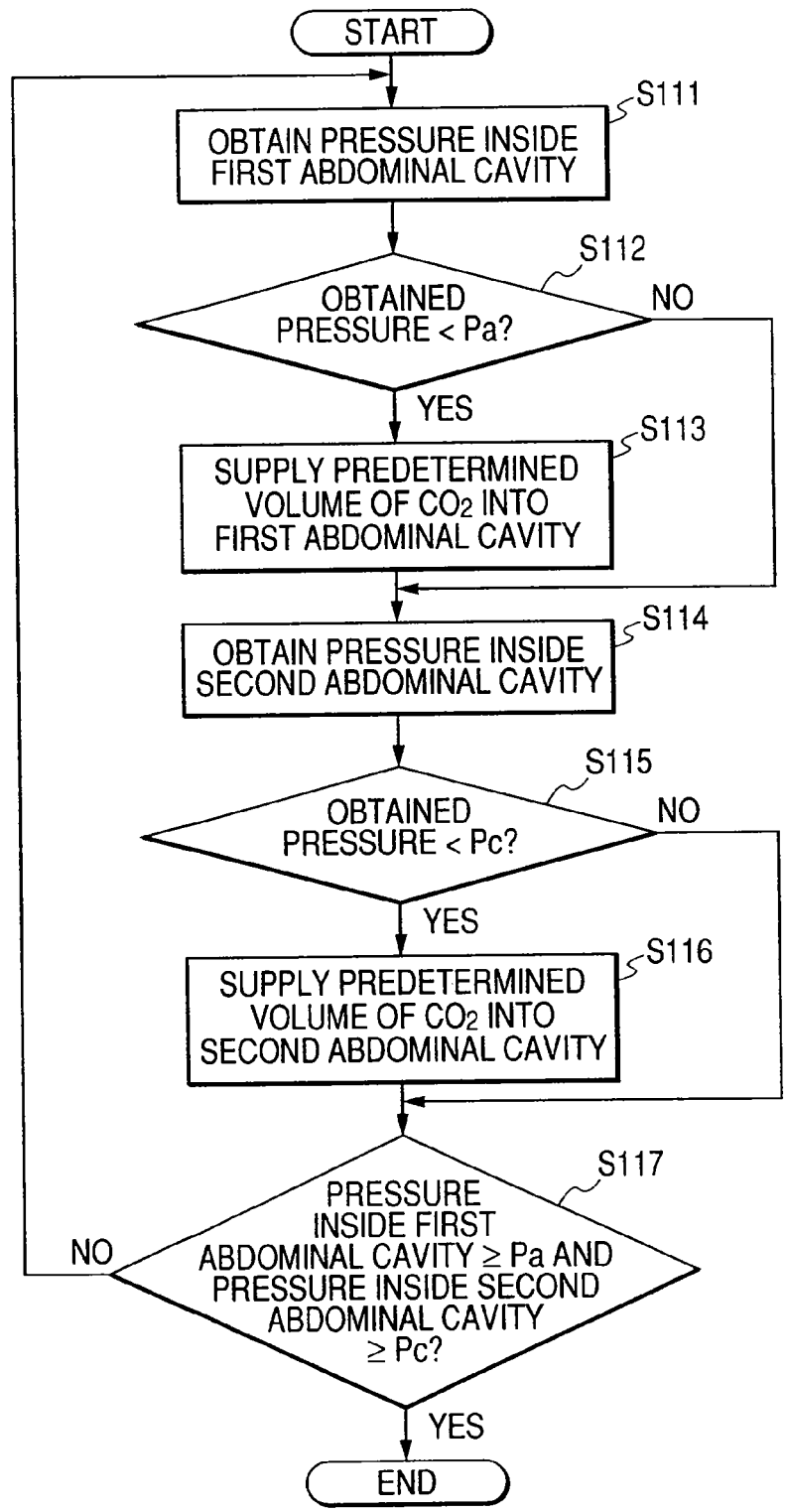
FIG. 32 is a flowchart schematically illustrating an example of control operations of the controller of the gas supply apparatus illustrated in FIG. 31.

In step S128, the controller 198 executes the operations similar in step S116 of FIG. 32 to regulate the pressure and the flow-rate of the carbon dioxide gas discharged from the electropneumatic proportional valve 93 and to control the third solenoid valve 94C to open it. This allows a predetermine volume of the carbon dioxide gas with the regulated pressure and flow-rate to be supplied into the second abdominal cavity AC2.

In step S130, the controller 198 determines whether the obtained pressures inside the first abdominal cavity AC1, the lumen BC, and the second abdominal cavity AC2 are equal to or higher than the first abdominal cavity target pressure Pa, the lumen target pressure Pb, and the second abdominal cavity target pressure Pc, respectively.

When it is determined that the obtained pressures inside the first abdominal cavity AC1, the lumen BC, and the second abdominal cavity AC2 are equal to or higher than the first abdominal cavity target pressure Pa, the lumen target pressure Pb, and the second abdominal cavity target pressure Pc, respectively, (the obtained pressures inside the first abdominal cavity, the lumen, and the second abdominal cavities≧Pa, Pb, and Pc), the determination in step S130 is YES. In this affirmative determination, for example, the controller 198 controls the first, second and third solenoid valves 95A, 95B, and 95C to close them, thereby interrupting the carbon dioxide gas insufflations of the first abdominal cavity AC1, the lumen BC, and the second abdominal cavity AC2.

In contrast, when it is determined that at least one of the obtained pressures inside the first abdominal cavity AC1, the lumen BC, and the second abdominal cavity AC2 is lower than corresponding at least one of the target pressures Pa, Pb, and Pc, the determination in step S130 is NO. In this negative determination, the controller 198 returns to step S121, and repeatedly executes the operations in steps S121 to S130. These operations in steps S121 to S130 allow the actual pressures inside the first abdominal cavity AC1, the lumen BC, and the second abdominal cavity AC2 to rise greater than the corresponding target pressures Pa, PB, and Pc, respectively.

As set forth above, in the gas supply apparatus 141 according to the eighth embodiment, the controller 198 obtains actual pressures inside the first abdominal cavity AC1, the lumen BC, and the second abdominal cavity AC2. Based on the obtained actual pressures, the controller 198 allows the carbon dioxide gas insufflations of the first abdominal cavity AC1, the lumen BC, and the second abdominal cavity AC2 while regulating the pressure and the flow-rate of the carbon dioxide gas within the appropriate ranges for the first abdominal cavity AC1, the lumen BC, and the second abdominal cavity AC2, respectively.

In addition, the controller 198 permits the alternative carbon dioxide gas insufflations of the first abdominal cavity AC1, the lumen BC, and the second abdominal cavity AC2 while checking whether the actual pressures inside the first abdominal cavity AC1, the lumen BC, and the second abdominal cavity AC2 are lower than the corresponding target pressures Pa, Pb, and Pc, respectively. These alternative carbon dioxide gas insufflations of the first abdominal cavity AC1, the lumen BC, and the second abdominal cavity AC2 make it possible to set the actual pressures inside the first abdominal cavity AC1, the lumen BC, and the second abdominal cavity AC2 to be higher than the corresponding target pressures Pa, PB, and Pc, respectively.

As described above, in the eighth embodiment of the present invention, the gas supply apparatus 141 with the first to third $CO_2$ supply paths DC1 to DC3 is configured to supply the carbon dioxide gas into the first abdominal cavity AC1, the lumen BC, and the second abdominal cavity AC2 through the first, second, and third $CO_2$ supply paths DC1, DC2, and DC3, respectively.

Like each of the aforementioned embodiments, the configuration of the gas supply apparatus 141 allows expansion of the field of each of the rigidscope 21, flexiblescope 31, and the rigidscope 121 in each of the first abdominal cavity AC1, the lumen BC, and the second abdominal cavity AC2 without using a plurality of insufflators and/or ECRs. In addition, the configuration of the gas supply apparatus 141 can provide a sufficient space for manipulating treatment tools in each of the first abdominal cavity AC1, the lumen BC, and the second abdominal cavity AC2 without using a plurality of insufflators and/or ECRs, which are similar to each of the aforementioned embodiments.

In addition, in the eighth embodiment, it is possible to set the pressure of the carbon dioxide gas to be insufflated into alternatively the first abdominal cavity AC1, the lumen BC, and the second abdominal cavity AC2 based on the measurement results corresponding to the actual pressures inside the body cavities (AC1, BC, and AC2), respectively. This can prevent the pressure inside each of the body cavities (AC1, BC, and AC2) from rapidly increasing.

Note that, in the eighth embodiment, the gas supply apparatus 141 is provided with the first adapter 41A, the second adapter 41B, and the third adapter 41G, but the present invention is not limited to the structure.

Specifically, in the eighth embodiment, the gas supply apparatus can be provided with two adapters and a switch. The switch allow selective connections of the adapters with any two of the delivery channels C6, C8, and C11 corresponding to the first, second, and third $CO_2$ supply paths DC1, DC2, and DC3. The selection of the switch can be controlled by the controller 198.

For example, when supplying the carbon dioxide gas into the first and second abdominal cavities AC1 and AC2, the first trocar 14 is connected to one of the adapters through the first tube 45a, and the fourth trocar 17 is connected to the other of the adapters through the third tube 45c.

In addition, the controller 198 controls the switch to connect the sixth delivery channel C6 to one of the adapters, and the eleventh delivery channel C11 to the other of the adapters. This connection allows the carbon dioxide gas to be supplied into the first and second abdominal cavities AC1 and AC2.

Moreover, when supplying the carbon dioxide gas into the first abdominal cavity AC1 and the lumen BC, the first trocar 14 is connected to one of the adapters through the first tube 45a, and the flexiblescope 31 is connected to the other of the adapters through the second tube 45b.

In addition, the controller 198 controls the switch to connect the sixth delivery channel C6 to one of the adapters, and the eighth delivery channel C8 to the other of the adapters. This connection allows the carbon dioxide gas to be supplied into the first abdominal cavity AC1 and the lumen BC.

The gas supply apparatus with two adapters set forth above can obtain the effects obtained by the gas supply apparatus 141 according to the eighth embodiment.

In the eighth embodiment, the gas supply apparatus 141 is provided with the first adapter 41A, the second adapter 41B, and the third adapter 41G, but the present invention is not limited to the structure.

Figure 35:
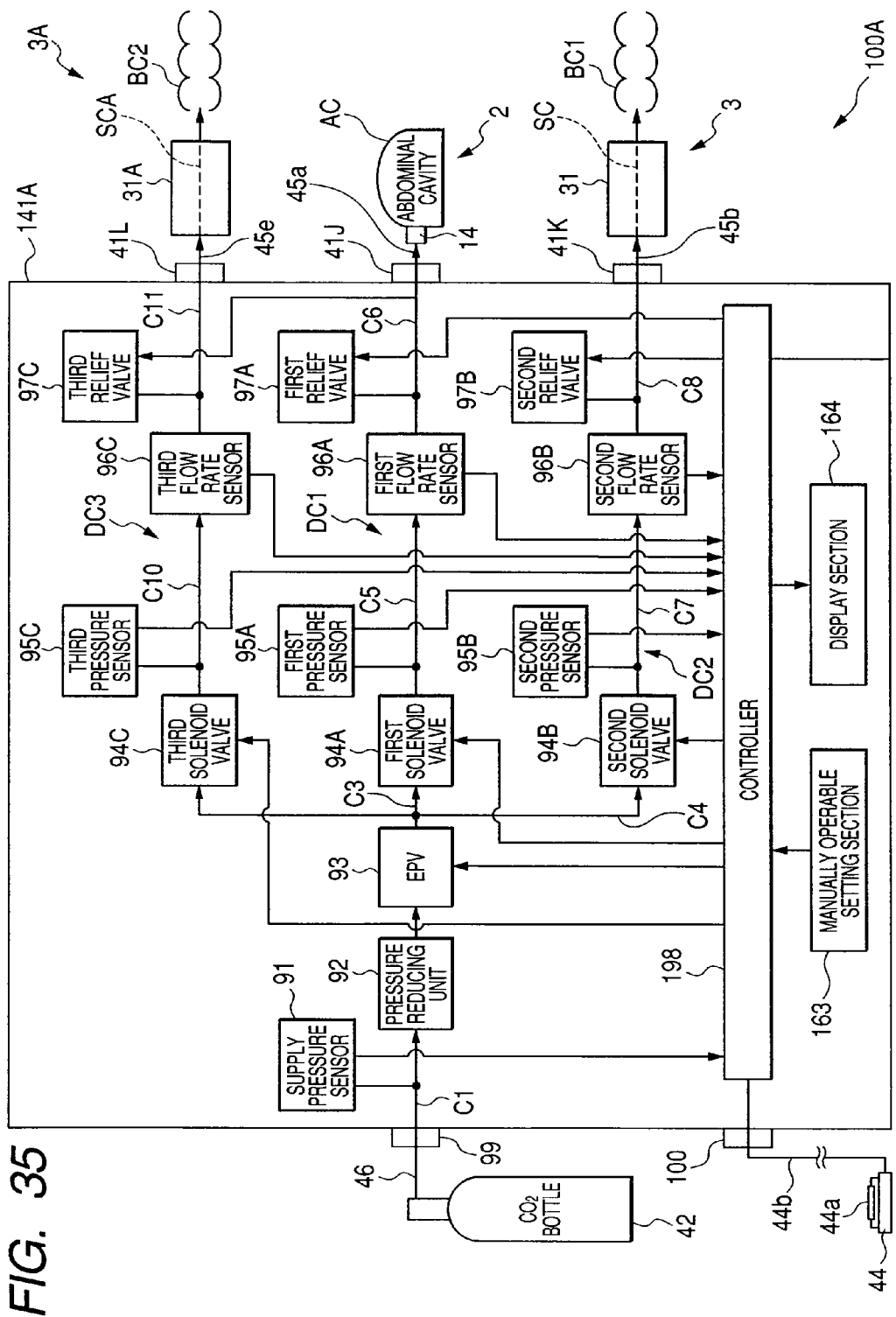
FIG. 35 is a block diagram illustrating a schematic structure of a surgical system with a gas supply apparatus according to a first modification of the eighth embodiment of the present invention.

FIG. 35 is a block diagram illustrating a schematic structure of a surgical system 100A with a gas supply apparatus 141A according to a first modification of the eighth embodiment of the present invention.

As illustrated in FIG. 35, the surgical system 100A according to the first modification of the eighth embodiment allows an operator to carry out surgical operations of at least one site to be treated of a patient 10 while the operator monitors at least one of the abdominal cavity AC, the first lumen BC1, and the second lumen BC2 of the patient 10.

Specifically, the surgical system 100A according to the first modification of the eighth embodiment includes the fourth endoscope system 3A for insufflation of the second lumen BC2 in addition to the first endoscope system 2 for insufflation of the abdominal cavity AC and the second endoscope system 3 for insufflation of the first lumen BC1.

The fourth endoscope system 3A has substantially the same structure as the second endoscope system 3. Specifically, a flexiblescope 31A of the fourth endoscope system 3A is optically coupled to the second light source 32, and the image pickup device provided in the flexiblescope 31A is electrically coupled to the second CCU 33.

In addition, the gas supply apparatus 141A is provided with a fourth adapter 41L for insufflation of the second lumen BC2 in addition to a first adapter 41J for insufflation of the abdominal cavity AC and a second adapter 41K for insufflation of the first lumen BC1.

Like each of the aforementioned embodiments, the first tube 45a is communicably coupled to the first adapter 41J, and the first tube 45a is communicably coupled to the first trocar 14 of the rigidscope 21. The second tube 45b is communicably coupled to the second adapter 41K, and the second tube 45b is communicably coupled to the gas delivery channel SC inside the flexiblescope 31.

Similarly, a fourth tube 45e is communicably coupled to the fourth adapter 41L, and the fourth tube 45e is communicably coupled to a gas delivery channel SCA inside the flexiblescope 31A.

In addition, the first, second, and fourth adapters 41J, 41K, and 41L are communicably connected to the delivery channels C6, C8, and C11, respectively.

In the structure of the gas supply apparatus 141A set fourth above, the controller 198 of the apparatus 141A can perform the control operations, which are the same as the eighth embodiment, making it possible to supply the carbon dioxide gas into the abdominal cavity AC, the first lumen BC1, and the second lumen BC2.

Figure 36:
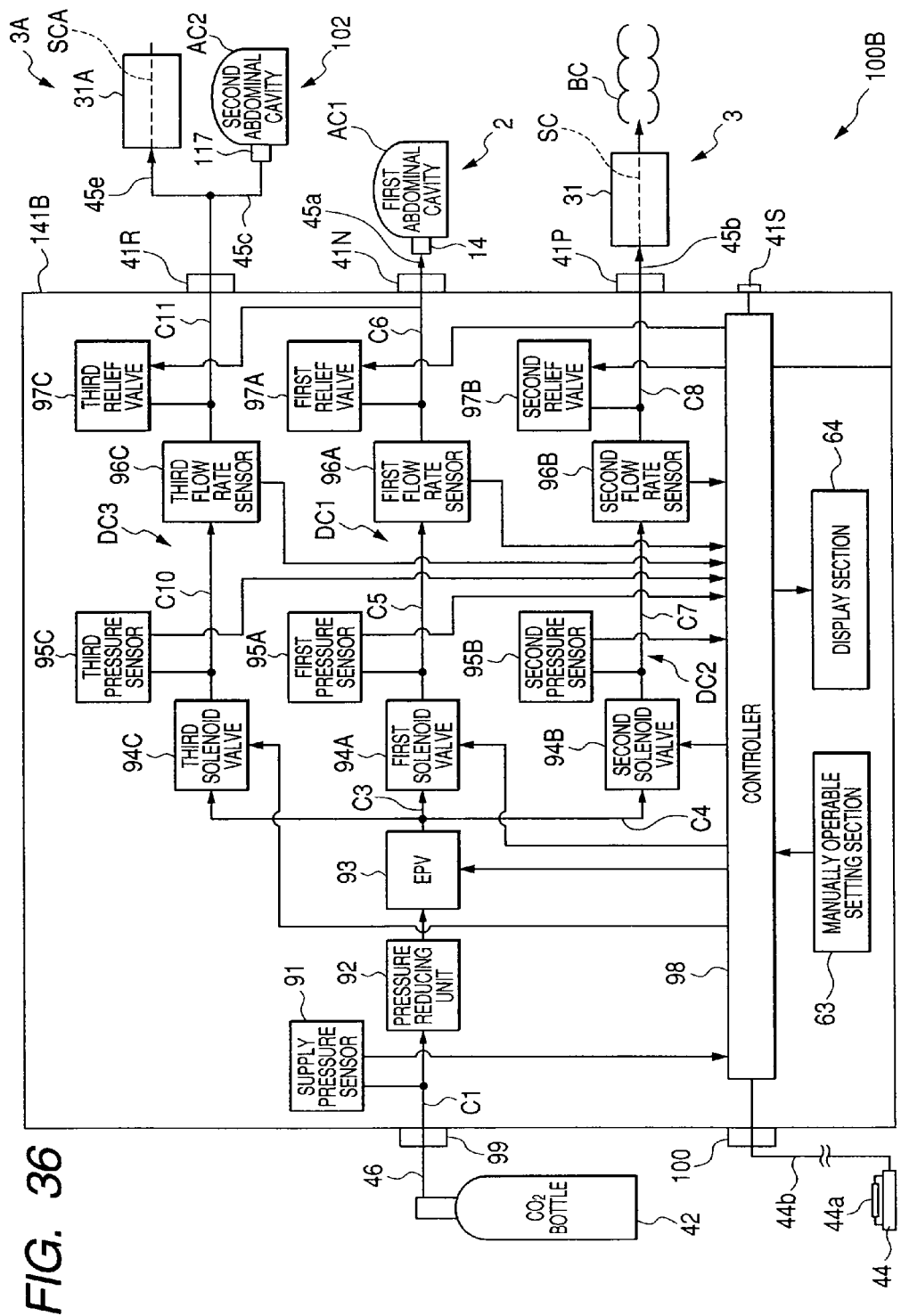
FIG. 36 is a block diagram illustrating a schematic structure of a gas supply apparatus according to a second modification of the eighth embodiment of the present invention.

FIG. 36 is a block diagram illustrating a schematic structure of a surgical system 100B with a gas supply apparatus 141B according to a second modification of the eighth embodiment of the present invention.

As illustrated in FIG. 36, the surgical system 100B according to the second modification of the eighth embodiment allows an operator to carry out surgical operations of at least one site to be treated of a patient 10 while the operator monitors at least one of the first abdominal cavity AC1, the second abdominal cavity AC2, the first lumen BC1, and the second lumen BC2 of the patient 10.

Specifically, the surgical system 100B according to the second modification of the eighth embodiment includes the first endoscope system 2 for insufflation of the first abdominal cavity AC1, and the second endoscope system 3 for insufflation of the first lumen BC1. In addition, the surgical system 100B includes the third endoscope system 102 for insufflation of the second abdominal cavity AC2, and the fourth endoscope system 3A for insufflation of the second lumen BC2.

In addition, the gas supply apparatus 141B is provided with a first adapter 41N for insufflation of the first abdominal cavity AC1, a second adapter 41P for insufflation of the first lumen BC1, and a switch adapter 41R for switching insufflation of the second abdominal cavity AC2 or the second lumen BC2.

As well as each of the aforementioned embodiments, the first tube 45a is communicably coupled to the first adapter 41N, and the first tube 45a is communicably coupled to the first trocar 14 of the rigidscope 21. The second tube 45b is communicably coupled to the second adapter 41P, and the second tube 45b is communicably coupled to the gas delivery channel SC inside the flexiblescope 31.

In addition, the switch adapter 41R is designed allow communicable connection with any one of the third tube 45c and the fourth tube 45e. The third tube 45c is communicably coupled to the fourth trocar 117 of the third endoscope system 102, and the fourth tube 45e is communicably coupled to the gas delivery channel SCA inside the flexiblescope 31A.

In addition, the first adapter 41N, the second adapter 41P, and the switch adapter 41R are communicably connected to the delivery channels C6, C8, and C11, respectively.

The gas supply apparatus 141B is provided with an adapter connection setting switch 41S electrically connected to the controller 198 thereof. The adapter connection setting switch 41S is operable by the operator and is configured to send, to the controller 198, information indicative of which one of the third and fourth tubes 45c and 45e is connected to the switch adapter 41R. In other words, the information is indicative of which one of a channel for the second abdominal cavity AC2 or that for the second lumen BC2 is connected to the switch adapter 41R.

For example, the adapter connection setting switch 41S includes at least first and second positions. Set of the switch 41S to the first position by the operator allows the adapter connection setting switch 41S to send, to the controller 198, identifying information representing that the channel (third tube 45c) for the second abdominal cavity AC2 is connected to the switch adapter 41R. In contrast, set of the switch 41S to the second position by the operator allows the switch 41S to send, to the controller 198, identifying information representing that the channel (fourth tube 45e) for the second lumen BC2 is connected to the switch adapter 41R.

Specifically, in the second modification of the eighth embodiment, when being desired to supply the carbon dioxide gas into the second abdominal cavity AC2 in addition to the first abdominal cavity AC1 and the first lumen BC1, the operator or the health worker connects the third tube 45c to the switch adapter 41R to be communicated therewith. Next, the operator or the health worker operates the adapter connection setting switch 41S to set to the first position.

The operation of the adapter connection setting switch 41S causes the switch 41S to send, to the controller 198, the identifying information representing that the channel (third tube 45c) for the second abdominal cavity AC2 is connected to the switch adapter 41R. The controller 198 receives the identifying information sent from the switch 41S to determine that the channel for the second abdominal cavity AC2 is connected to the switch adapter 41R based on the received identifying information. Then, the controller 198 performs the operations shown in FIG. 34. This results in that the carbon dioxide gas is supplied into the first abdominal cavity AC1, the first lumen BC1, and the second abdominal cavity AC2.

In contrast, when being desired to supply the carbon dioxide gas into the second lumen BC2 in addition to the first abdominal cavity AC1 and the first lumen BC1, the operator or the health worker connects the fourth tube 45e to the switch adapter 41R to be communicated therewith. Next, the operator or the health worker operates the adapter connection setting switch 41S to set to the second position.

The operation of the adapter connection setting switch 41S causes the switch 41S to send, to the controller 198, the identifying information representing that the channel (fourth tube 45e) for the second lumen BC2 is connected to the switch adapter 41R. The controller 198 receives the identifying information sent from the switch 41S to determine that the channel for the second lumen BC2 is connected to the switch adapter 41R based on the identifying information. Then, the controller 198 performs the operations shown in FIG. 34 by replacing the second abdominal cavity AC2 into the second lumen BC2.

This results in that the carbon dioxide gas is supplied into the first abdominal cavity AC1, the first lumen BC1, and the second lumen BC2.

As set forth above, in the second modification of the eighth embodiment, operations of the switch 41S to select any one of the first and second positions allow carbon dioxide gas insufflation of selectively one of the first group of the body cavities (AC1, AC2 and BC1), and the second group of the body cavities (AC1, BC1, and BC2).

Note that the gas supply apparatus according to the second medication of the eighth embodiment can be provided with four or more adapters, and a plurality of channels for a plurality of abdominal cavities and those for a plurality of lumens can be connected to the four or more adapters, respectively. This structure allows carbon dioxide gas insufflations of the plurality of abdominal cavities and the plurality of lumens.

Figure 34:
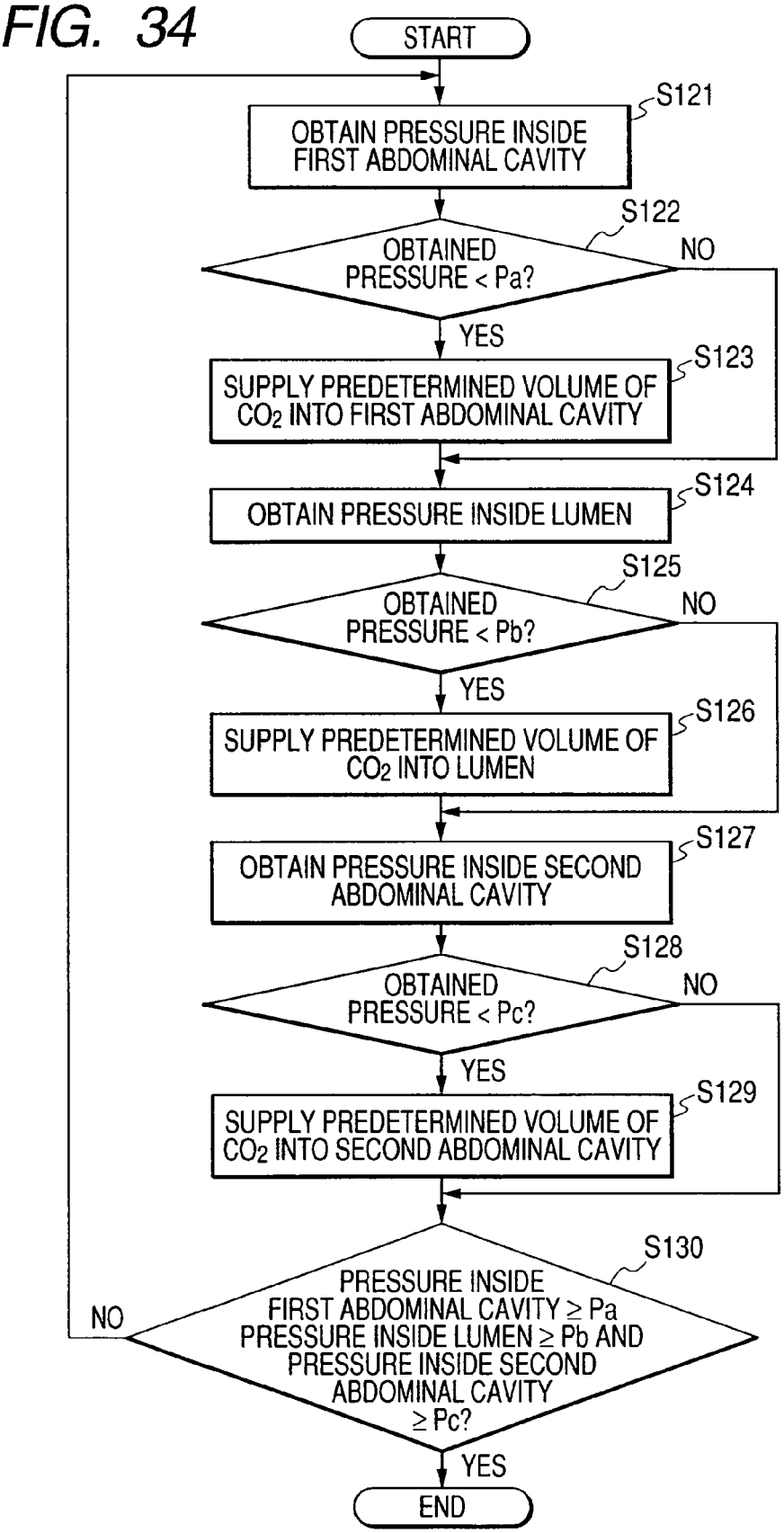
FIG. 34 is a flowchart schematically illustrating an example of control operations of the controller of the gas supply apparatus illustrated in FIG. 33.

Note that, in the eighth embodiment, controller's control operations of carbon dioxide gas insufflations in the predetermined order of the first abdominal cavity AC1, the lumen BC, and the second abdominal cavity AC2 have been described with the use of FIG. 34, but the present invention is not limited to the structure.

For example, the controller 198 can perform control operations of carbon dioxide gas insufflations in any order. For example, the controller 198 can perform control operations of carbon dioxide gas insufflations in the order of the lumen BC, the first abdominal cavity AC1, and the second abdominal cavity AC2.

In addition, determining means for allowing an operator to determine an order of carbon dioxide gas insufflations of the plurality of cavities and lumen(s), such as a selection switch, can be provided on, for example, the front panel FP10. The controller 198 can perform control operations of carbon dioxide gas insufflations of the plurality of cavities and lumen(s) in the order determined by operations of the determining means by the operator.

Moreover, the controller 198 can perform control operations of carbon dioxide gas insufflations of the plurality of cavities and lumen(s) in descending order of target pressure. In this modification, it can expect to shorten time until each of the pressures inside of each of the cavities and lumen(s) reaches a corresponding target pressure. Moreover, the controller 198 can perform control operations of carbon dioxide gas insufflations of the body cavities (AC1, BC, AC2) in descending order of difference between each pressure inside each of the body cavities (AC1, BC, AC2) and each target pressure therefor.

Furthermore, in the ninth embodiment and its modifications, the first CCU 23A and the first light source 22A are used in common for the first and third endoscope systems 2 and 102, but a plurality of CCUs and a plurality of light sources can be prepared for a plurality of endoscope systems for insufflations of a plurality of body cavities.

Ninth Embodiment

Figure 37:
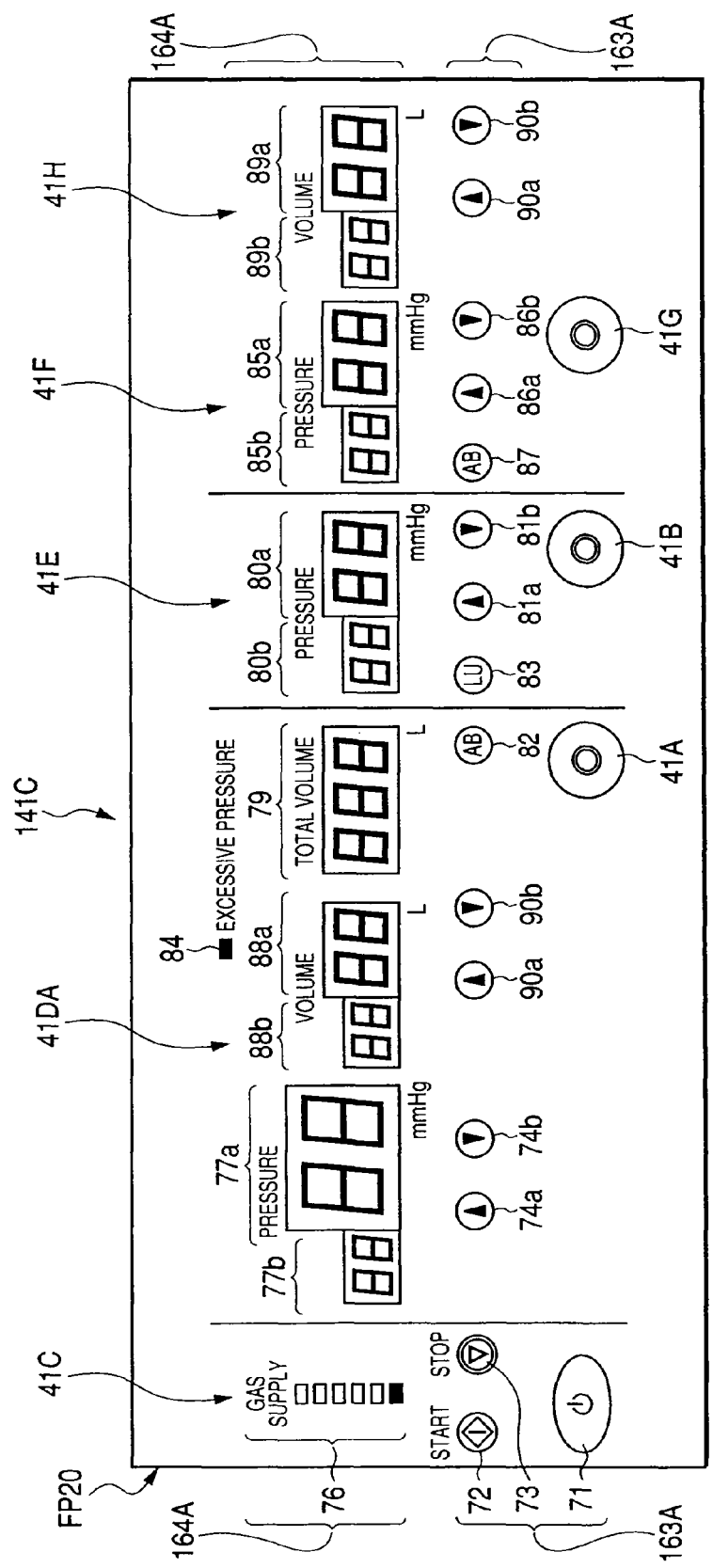
FIG. 37 is a view schematically illustrating a configuration example of a manually operable setting section and a display section provided on a front panel of a gas supply apparatus according to a ninth embodiment of the present invention.

A configuration example of a manually operable setting section 163A and a display section 164A provided on a front panel FP20 of a gas supply apparatus 141C of a surgical system according to a ninth embodiment of the present invention is illustrated in FIG. 37. In the ninth embodiment, the manually operable setting section 163A and the display section 64 are, for example, graphically displayed on the front panel FP of the gas supply apparatus 41.

The manually operable setting section 163A and display section 164A are divided in, for instance, five graphical setting and display sections 41C, 41DA, 41E, 41F, and 41H. Because the setting and display sections 41C, 41E, and 41F are substantially identical to those of the gas supply apparatus 141, the descriptions of which are omitted.

The setting and display section 41DA includes volume displays 88a and 88b for insufflation of the first abdominal cavity AC1 as the display section 164A in place of the flow-rate displays 78a and 78b. In addition, the setting and display section 41DA includes volume setting buttons 90a and 90b for insufflation of the first abdominal cavity AC1 as the manually operable setting section 163A in place of the flow-rate setting buttons 75a and 75b.

The setting and display section 41H includes volume displays 89a and 89b as the display section 164A. The setting and display section 41H also includes volume setting buttons 90c and 90d as the manually operable setting section 163A.

Click of each of the volume setting buttons 90a and 90c allows an instruction to be sent to the controller 198. The instruction is indicative of incrementing a corresponding parameter, such as a first volume setting for the first abdominal cavity AC1 and a second volume setting for the second abdominal cavity AC2, by, for example, 1 mmHg.

Click of each of the volume setting buttons 90b and 90d permits an instruction to be sent to the controller 198. The instruction is indicative of decrementing a corresponding parameter, such as the first volume setting or the second volume setting, by, for example, 1 mmHg.

The volume display 88a is configured to display a flow volume of the carbon dioxide gas in the first abdominal cavity AC1; this flow volume is accumulated by the controller 198 based on measured values of the first flow-rate sensor 96A. The volume display 88b is configured to display the first volume setting determined based on operations of the volume setting buttons 90a and 90b.

Similarly, the volume display 89a is configured to display a flow volume of the carbon dioxide gas in the second abdominal cavity AC2; this flow volume is accumulated by the controller 198 based on measured values of the third flow-rate sensor 96C. The volume display 88b is configured to display the second volume setting determined based on operations of the volume setting buttons 90c and 90d.

Note that other elements of the gas supply apparatus 141C and the surgical system according to the ninth embodiment are represented by the same reference characters as in the gas supply apparatus 141 and the surgical system 100 according to the eighth embodiment. The descriptions of the other elements of the gas supply apparatus 141C and the surgical system according to the ninth embodiment are therefore omitted.

Figure 38:
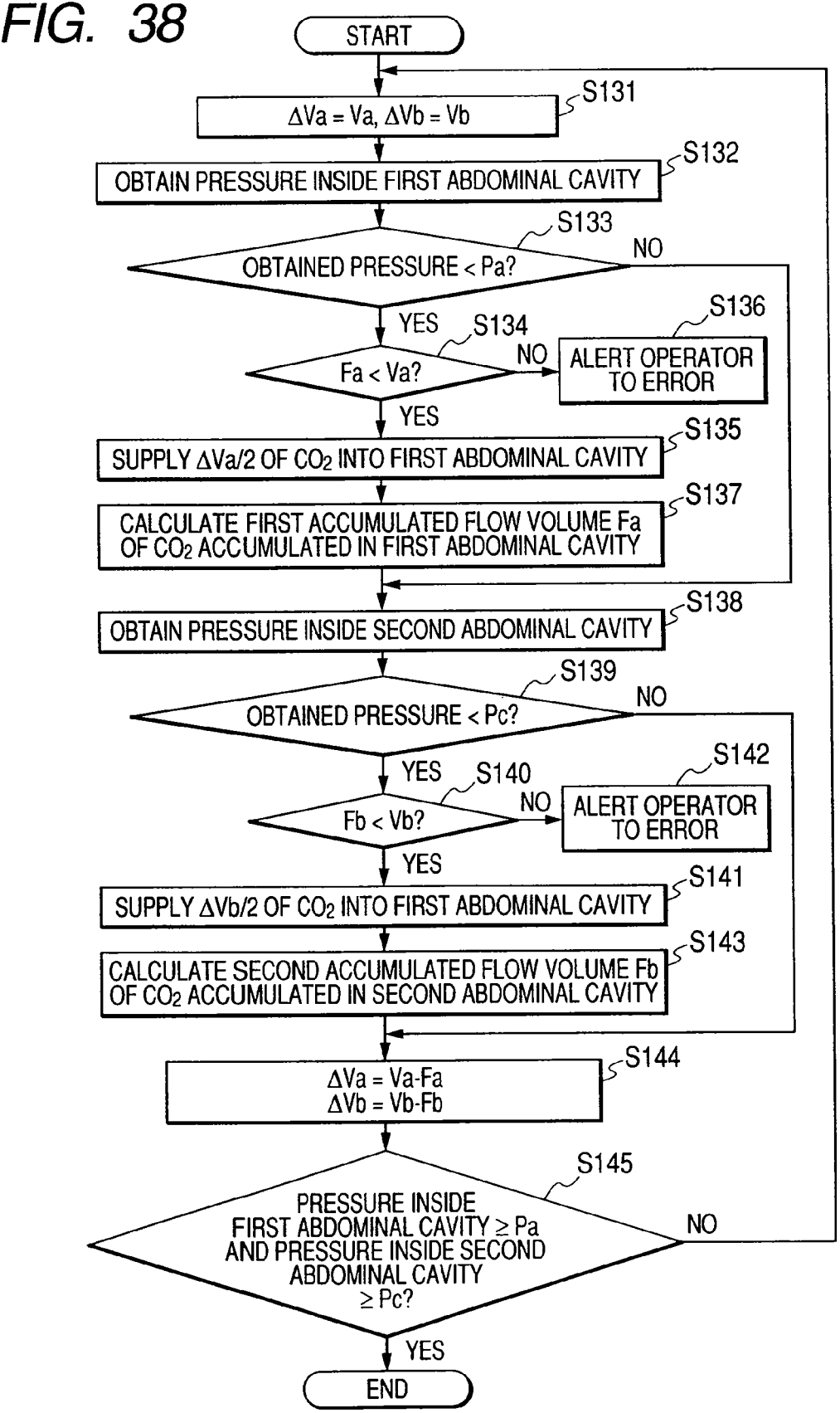
FIG. 38 is a flowchart schematically illustrating an example of control operations of the controller of the gas supply apparatus according to the ninth embodiment of the present invention.

Next, an example of control operations of the controller 198 of the gas supply apparatus 141C when insufflating the carbon dioxide gas into both the first abdominal cavity AC1 and the second abdominal cavity AC2 will be described hereinafter with reference to FIG. 38.

When the first abdominal cavity select button 82, the second abdominal cavity select button 87, and the gas-supply start button 72 are in on state, respectively, the controller 198 enters the first and second abdominal cavity insufflation mode.

In the first and second abdominal cavity insufflation mode, the controller 198, as an operation step, defines the first volume setting (Va) displayed on the volume display 88b as a first maximum acceptable volume ($\Delta$Va) of the carbon dioxide gas in the first abdominal cavity AC1. Similarly, the controller 198, as the operation step, defines the second volume setting (Vb) displayed on the volume display 89b as a second maximum acceptable volume ($\Delta$Vb) of the carbon dioxide gas in the second abdominal cavity AC2 in step S131 of FIG. 38.

Next, the controller 198 obtains an actual pressure inside the first abdominal cavity AC1 based on the pressure value that is measured by the first pressure sensor 95A with the first solenoid valve 94A closed in step S132.

Thereafter, the controller 198 determines whether the obtained pressure reaches the first abdominal cavity target pressure Pa set on the front panel FP10 and displayed on the pressure display 77b in step S133.

When it is determined that the obtained pressure does not reach the first abdominal cavity target pressure Pa (the obtained pressure<Pa), the determination in step S133 is YES so that the controller 198 shifts to step S134. In contrast, when it is determined that the obtained pressure reaches the first abdominal cavity target pressure Pa (the obtained pressure≦Pa), the determination in step S133 is NO so that the controller 198 shifts to step S138.

In step S134, the controller 198 determines whether a first accumulated flow volume Fa of the carbon dioxide gas in the first abdominal cavity AC1, which has been calculated by the operation of the controller 198 based on the measured values by the first flow-rate sensor 96A in step S137 described hereinafter, reaches the first volume setting Va.

The first accumulated flow volume Fa represents a total volume of the carbon dioxide gas accumulated in the first abdominal cavity AC1 from the start of carbon dioxide gas insufflation of the first abdominal cavity AC1 in the first and second abdominal cavity insufflation mode.

Note that, after the start of carbon dioxide gas insufflation of the first abdominal cavity AC1 in the first and second abdominal cavity insufflation mode, when the controller 198 is first to perform the operation in step S134, the first accumulated flow volume Fa is set to an initial value of zero.

When it is determined that the first accumulated flow volume Fa does not reach the first volume setting Va (the first accumulated flow volume Fa<Va), the determination in step S134 is YES so that the controller 198 shifts to step S135. In contrast, when it is determined that the first accumulated flow volume Fa reaches the first volume setting Va (the first accumulated flow volume Fa≧Va), the determination in step S134 is NO so that the controller 198 shifts to step S136.

In step S135, the controller 198 controls the opening of the electropneumatic proportional valve 93 and controls to open the first solenoid valve 94A during a predetermined period. The controls of the valves 93 and 94A allow a predetermined volume of the carbon dioxide gas to be supplied through the first $CO_2$ supply path DC1 into the first abdominal cavity AC1 at a time, shifting to step S137. The predetermined volume of the carbon dioxide gas is equivalent to a predetermined percentage of the first maximum acceptable volume ΔVa of the carbon dioxide gas. For example, in the ninth embodiment, the predetermined percentage is set to 50%, so that the predetermined volume corresponds to ΔVa/2.

In contrast, in step S136, the controller 198 determines that the first accumulated flow volume Fa is larger than the first volume setting Va so that the controller 198 performs a predetermined operation required to alert the operator to an error. As the error alert operation, for example, the controller 198 generates an alarm or causes the excessive pressure indicator 84 to turn on or flash on and off.

In step S137, the controller 198 has calculated the first accumulated flow volume Fa representing the total volume of the carbon dioxide gas accumulated in the first abdominal cavity AC1 since the start of carbon dioxide gas insufflation thereof in the first and second abdominal cavity insufflation mode based on the measured values by the first flow-rate sensor 96A.

Subsequently, in step S138, the controller 198 obtains an actual pressure inside the second abdominal cavity AC2 based on the pressure value that is measured by the third pressure sensor 95C with the third solenoid valve 94C closed.

Thereafter, the controller 198 determines whether the obtained pressure reaches the second abdominal cavity target pressure Pc set on the front panel FP10 and displayed on the pressure display 77b in step S139.

When it is determined that the obtained pressure does not reach the second abdominal cavity target pressure Pc (the obtained pressure<Pc), the determination in step S139 is YES so that the controller 198 shifts to step S140. In contrast, when it is determined that the obtained pressure reaches the second abdominal cavity target pressure Pc (the obtained pressure≧Pc), the determination in step S140 is NO so that the controller 198 shifts to step S145.

In step S140, the controller 198 determines whether a second accumulated flow volume Fb of the carbon dioxide gas in the second abdominal cavity AC2, which has been calculated by the operation of the controller 198 based on the measured values by the third flow-rate sensor 96C in step S143 described hereinafter, reaches the second volume setting Vb.

The second accumulated flow volume Fb represents a total volume of the carbon dioxide gas accumulated in the second abdominal cavity AC2 from the start of carbon dioxide gas insufflation of the second abdominal cavity AC2 in the first and second abdominal cavity insufflation mode.

Note that, after the start of carbon dioxide gas insufflation of the second abdominal cavity AC2 in the first and second abdominal cavity insufflation mode, when the controller 198 is first to perform the operation in step S140, the second accumulated flow volume Fb is set to an initial value of zero.

When it is determined that the second accumulated flow volume Fb does not reach the second volume setting Vb (the second accumulated flow volume Fb<Vb), the determination in step S140 is YES so that the controller 198 shifts to step S141. In contrast, when it is determined that the second accumulated flow volume Fb reaches the second volume setting Vb (the second accumulated flow volume Fb≧Vb), the determination in step S140 is NO so that the controller 198 shifts to step S142.

In step S141, the controller 198 controls the opening of the electropneumatic proportional valve 93 and controls to open the third solenoid valve 94C during a predetermined period. The controls of the valves 93 and 94C allow a predetermined volume of the carbon dioxide gas to be supplied through the third $CO_2$ supply path DC3 into the second abdominal cavity AC2 at a time, shifting to step S143. The predetermined volume of the carbon dioxide gas is equivalent to a predetermined percentage of the second maximum acceptable volume ΔVb of the carbon dioxide gas. For example, in the ninth embodiment, the predetermined percentage is set to 50%, so that the predetermined volume corresponds to ΔVb/2.

In contrast, in step S142, the controller 198 determines that the second accumulated flow volume Fb is larger than the second volume setting Vb so that the controller 198 performs a predetermined operation required to alert the operator to an error. The error alert operation is similar to that described in step S136.

In step S143, the controller 198 has calculated the second accumulated flow volume Fb representing the total volume of the carbon dioxide gas accumulated in the second abdominal cavity AC2 since the start of carbon dioxide gas insufflation thereof in the first and second abdominal cavity insufflation mode based on the measured values by the third flow-rate sensor 96C.

Subsequently, in step S144, the controller 198 calculates the difference between the first volume setting Va and the first accumulated flow volume Fa obtained in step S137, and redefines the calculated difference as the first maximum acceptable volume ΔVa. Similarly, in step S144, the controller 198 calculates the difference between the second volume setting Vb and the second accumulated flow volume Fb obtained in step S143, and redefines the calculated difference as the second maximum acceptable volume ΔVb, shifting to step S145.

In step S145, the controller 198 determines whether the obtained pressure inside the first abdominal cavity AC1 is equal to or higher than the first abdominal cavity target pressure Pa and the obtained pressure inside the second abdominal cavity AC2 is equal to or higher than the second abdominal cavity target pressure Pc.

When it is determined that the obtained pressures inside the first and second abdominal cavities AC1 and AC2 are equal to or higher than the first and second abdominal cavity target pressures Pa and Pc, respectively, (the obtained pressures inside the first and second abdominal cavities≧Pa and Pc), the determination in step S145 is YES. In this affirmative determination, for example, the controller 198 controls the first and third solenoid valves 95A and 95C to close them, thereby interrupting the carbon dioxide gas insufflations of both the first and second abdominal cavities AC1 and AC2.

In contrast, when it is determined that at least one of the obtained pressures inside the first and second abdominal cavities AC1 and AC2 is lower than at least one of the first and second abdominal cavity target pressures Pa and Pc, the determination in step S145 is NO. In this negative determination, the controller 198 returns to step S132, and repeatedly executes the operations in steps S132 to S145. These operations in steps S132 to S145 allow the actual pressures inside the first and second abdominal cavities AC1 and AC2 to rise greater than the corresponding first and second abdominal cavity target pressures Pa and Pc, respectively.

That is, in the ninth embodiment, the controller 198 obtains an actual pressure inside the first abdominal cavity AC1, and that inside the second abdominal cavity AC2. In addition, the controller 198 obtains total volumes of the carbon dioxide gas accumulated in the first and second abdominal cavities AC1 and AC2 since the start of carbon dioxide gas insufflation thereof in the first and second abdominal cavity insufflation mode.

Based on the obtained actual pressures, the controller 198 allows the carbon dioxide gas insufflations of the first and second abdominal cavities AC1 and AC2 while regulating the pressure and flow-rate of the carbon dioxide gas within the appropriate ranges for the first and second abdominal cavities AC1 and AC2, respectively.

In addition, the controller 198 permits the alternative carbon dioxide gas insufflations of the first and second abdominal cavities AC1 and AC2 while monitoring the obtained total volumes therein and checking whether the actual pressures inside the first and second abdominal cavities AC1 and AC2 are lower than the corresponding first and second abdominal cavity target pressures Pa and Pc, respectively, These alternative carbon dioxide gas insufflations of the first and second abdominal cavities AC1 and AC2 make it possible to set the actual pressures inside the first and second abdominal cavities AC1 and AC2 to be higher than the first and second abdominal cavity target pressures Pa and Pc, respectively.

As described above, in the ninth embodiment of the present invention, the gas supply apparatus 141C with the first and third $CO_2$ supply paths DC1 and DC3 is configured to supply the carbon dioxide gas into both the first and second abdominal cavities AC1 and AC2 through the first and third $CO_2$ supply paths DC1 and DC3.

Similar to each of the aforementioned embodiments, the configuration of the gas supply apparatus 141C allows expansion of the field of each of the rigidscopes 21 and 121 in each of the first and second abdominal cavities AC1 and AC2. In addition, the configuration of the gas supply apparatus 141C can provide a sufficient space for manipulating treatment tools in each of the first and second abdominal cavities AC1 and AC2, which are similar to each of the aforementioned embodiments.

In addition, in the ninth embodiment of the present invention, constant comparison of the total volumes of the carbon dioxide gas supplied in the first and second abdominal cavities AC1 and AC2 with corresponding first and second volume settings therefor can prevent the carbon dioxide gas from excessively being supplied into the first and second abdominal cavities AC1 and AC2, respectively.

Other operations and effects obtained by the gas supply apparatus 141C according to the ninth embodiment are substantially identical with those of the gas supply apparatus 141 according to the eighth embodiment.

Note that, in the ninth embodiment, control operations of the controller 198 when the gas supply apparatus 141C supplies the carbon dioxide gas into both the first and second abdominal cavities AC1 and AC2 have been described, but the present invention is not limited to the structure. Specifically, the controller 198 can perform substantially the same operations as those illustrated in FIG. 38 in cases where the gas supply apparatus 141C supplies the carbon dioxide gas into at least one abdominal cavity and at least one lumen.

In the first to ninth embodiments and their modifications, the controller 98 or 198 carries out the insufflation control operations shown in FIGS. 6, 13A, 13B, 15, 17-21, 25, 29, 32, 34, and 38, but the system controller 5 can execute them.

In the first to ninth embodiments and their modifications, the second tube 45b communicably coupled to the second adapter 41B is communicably coupled to the adapter 43 of the manipulator 35 of the flexiblescope 31, but the present invention is not limited to the structure. Specifically, the second tube 45b can be attached to the manipulator at a position thereof to be airtightly communicated with the gas delivery channel SC inside the manipulator 35; this position is located to the manipulator 35 at upstream of the gas and water supply switch 35a through which a through hole is formed. In this structure, operator's open and close of the through hole of the gas and water supply switch 35a allows the carbon dioxide gas to be supplied through the second tube 45b and the flexiblescope 31 (gas delivery channel SC) into lumen BC without operating the foot switch 44.

In the first to ninth embodiments and their modifications, the rigidscope and the flexiblescope are used as observation devices for observing the inside of a patient, but the present invention is not limited to the structure. Specifically, other types of endoscopes, such as a wireless capsule endoscope or the like, or other observation devices except for endoscopes, each of which is configured to be inserted into the inside of a patient, can be used for observing the inside of the patient.

In the first to ninth embodiments and their modifications, the flexiblescope 31 or 31A constitutes part of an insufflation-gas delivery path from the gas supply apparatus, but the present invention is not limited to the structure. Specifically, an insufflation-gas delivery path independent of the flexiblescope 31 or 31A can be provided in each of the gas supply systems according to the first to ninth embodiments and their modifications.

Furthermore, it should be noted that the term "body cavity" means not only a cavity that originally exists in the body of a patient, but also a cavity (space) to be artificially formed in the body of a patient with medical instruments.

For example, the term "body cavity" according to the specification includes, as the former means, an abdominal cavity, a retroperitoneal cavity, and lumens including upper alimentary tracts (esophagus, stomach, or the like), lower alimentary tracts (large intestine, small intestine, or the like), a bladder, and a uterus.

In addition, the term "body cavity" according to the specification includes, as the later means, a cavity to secure the field of an endoscope during surgery, such as subcutaneous cavity and the like.

While there has been described what is at present considered to be the embodiment and modifications of the invention, it will be understood that various modifications which are not described yet may be made therein, and it is intended to cover in the appended claims all such modifications as fall within the true spirit and scope of the invention.

The structures shown in the first to ninth embodiments and their modifications can be applied therebetween within the scope of the present invention.

What is claimed is:

1. A gas supply apparatus comprising:
   a gas supply source that supplies predetermined gas;
   a first delivery channel that delivers the predetermined gas supplied from the gas supply source into a lumen of a patient;
   a second delivery channel that delivers the predetermined gas supplied from the gas supply source into a lumen of the patient;
   a pressure regulator that regulates a pressure of the predetermined gas supplied from the gas supply source including:
      a first pressure value suitable for the abdominal cavity when the predetermined gas is delivered by the first delivery channel, and
      a second pressure value suitable for the lumen when the predetermined gas is delivered by the second delivery channel;
   a first pressure measuring unit that measures a pressure of gas in the first delivery channel;
   a second pressure measuring unit that measures a pressure of gas in the second delivery channel;
   an input unit that inputs a first instructed value as a first pressure setting for the abdominal cavity and a second instructed value as a second pressure setting for the lumen;
   a setting unit that, when at least one of the first and second instructed values are inputted by the input unit, forcibly sets, based on the at least one of the first and second instructed values, the second pressure setting to be greater than the first pressure setting; and
   a controller that controls the pressure regulator based on a result of the measurement of the first measuring unit, a result of the measurement of the second measuring unit, the at least one of the first and second instructed values inputted by the input unit, and a result of the second pressure setting of the setting unit.

2. The gas supply apparatus according to claim 1, wherein the setting unit is configured to, when the at least one of the first and second instructed values is inputted by the input unit, forcibly sets the second pressure setting to the sum of the first instructed value and the second instructed value.

3. The gas supply apparatus according to claim 1, wherein the setting unit is configured to, when the at least one of the first and second instructed values is inputted by the input unit, forcibly sets the second pressure setting to the sum of the first instructed value and a predetermined value, the predetermined value being selectable between a plurality of values.

4. The gas supply apparatus according to claim 1, wherein the first and second instructed values are inputted by the input unit, and the setting unit is configured to:
   set the first setting value based on the first instructed value;
   add a preset value to the first setting value to calculate a lower limit value for the second pressure setting;
   determine whether the second instructed value is higher than the lower limit value;
   forcibly set the second pressure setting to the lower limit value when it is determined that the second instructed value is equal to or lower than the lower limit value; and
   forcibly set the second pressure setting to the second instructed value when it is determined that the second instructed value is higher than the lower limit value.

5. The gas supply apparatus according to claim 1, wherein the first and second instructed values are inputted by the input unit, and the setting unit is configured to:
   set the second setting value based on the second instructed value;
   subtract a preset value from the second setting value to calculate a higher limit value for the first pressure setting;
   determine whether the first instructed value is equal to or higher than the higher limit value;
   set the first pressure setting to the higher limit value when it is determined that the first instructed value is higher than the higher limit value; and
   forcibly set the first pressure setting to the first instructed value when it is determined that the first instructed value is equal to or lower than the higher limit value.

* * * * *

UNITED STATES PATENT AND TRADEMARK OFFICE
CERTIFICATE OF CORRECTION

PATENT NO. : 7,981,072 B2  
APPLICATION NO. : 12/650861  
DATED : July 19, 2011  
INVENTOR(S) : Takefumi Uesugi Page 1 of 1

It is certified that error appears in the above-identified patent and that said Letters Patent is hereby corrected as shown below:

Title page, items (63) and (30) should read as follows:

(63) Continuation of application No. 11/265,687, filed on November 2, 2005, now abandoned, which is a CIP of application No. 11/093,389, filed on March 30, 2005

(30) Nov. 2, 2004 (JP)....................2004-319747  
      Nov. 5, 2004 (JP)....................2004-322640  
      Mar. 31, 2004 (JP)....................2004-108364

Signed and Sealed this  
Nineteenth Day of June, 2012

David J. Kappos  
*Director of the United States Patent and Trademark Office*